(12) United States Patent
Zagar et al.

(10) Patent No.: US 6,232,470 B1
(45) Date of Patent: May 15, 2001

(54) SUBSTITUTED PYRAZOL-3-YLBENZAZOLES, THEIR USE AS HERBICIDES OR DESICCANTS/DEFOLIANTS, AND THEIR PREPARATION

(75) Inventors: Cyrill Zagar, Ludwigshafen; Gerhard Hamprecht, Weinheim; Markus Menges, Mannheim; Olaf Menke, Altleiningen; Peter Schäfer, Ottersheim; Karl-Otto Westphalen, Speyer; Ulf Misslitz, Neustadt; Helmut Walter, Obrigheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/331,065
(22) PCT Filed: Dec. 1, 1997
(86) PCT No.: PCT/EP97/06715
§ 371 Date: Jun. 16, 1999
§ 102(e) Date: Jun. 16, 1999
(87) PCT Pub. No.: WO98/27090
PCT Pub. Date: Jun. 25, 1998

(30) Foreign Application Priority Data
Dec. 16, 1996 (DE) ................................. 196 52 240

(51) Int. Cl.[7] ............... C07D 417/04; C07D 417/10; C07D 413/10; C07D 413/04; A01N 43/56
(52) U.S. Cl. ................ 548/217; 504/243; 504/246; 504/262; 504/263; 504/265; 504/266; 548/120; 548/152; 548/159; 548/162; 548/161; 548/164; 548/222; 548/173
(58) Field of Search ............... 548/159, 120, 548/162, 217, 222, 161, 164, 173; 504/246, 262, 263, 265, 266, 243

(56) References Cited

U.S. PATENT DOCUMENTS

| | | | |
|---|---|---|---|
| 4,376,122 | 3/1983 | Dusza et al. | 424/270 |
| 5,424,443 | 6/1995 | Ganzer et al. | 548/159 |
| 5,675,017 | 10/1997 | Hamper et al. | 548/377 |
| 5,888,940 | 3/1999 | Heistracher et al. | 504/243 |

FOREIGN PATENT DOCUMENTS

| | | |
|---|---|---|
| 3705933 | 9/1988 | (DE) . |
| 3705935 | 9/1988 | (DE) . |
| 4241658 | 6/1994 | (DE) . |
| 155523 | 9/1985 | (EP) . |
| 235567 | 9/1987 | (EP) . |
| 3047180 | 4/1990 | (JP) . |
| 03081275 | 5/1990 | (JP) . |
| 92/02509 | 2/1992 | (WO) . |
| 92/06962 | 4/1992 | (WO) . |
| 92/20675 | 11/1992 | (WO) . |
| 96/01254 | 1/1996 | (WO) . |
| 96/01255 | 1/1996 | (WO) . |
| 96/11516 | 5/1996 | (WO) . |
| 96/15115 | 5/1996 | (WO) . |
| 96/40643 | 12/1996 | (WO) . |
| 97/08171 | 3/1997 | (WO) . |

Primary Examiner—Floyd D. Higel
(74) Attorney, Agent, or Firm—Keil & Weinkauf

(57) ABSTRACT

Substituted Pyrazol-3-ylbenzazoles I

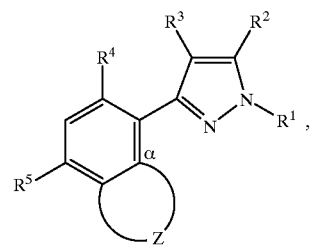

I salts thereof, and their use as herbicides or for the desiccation/defoliation of plants.

27 Claims, No Drawings

SUBSTITUTED PYRAZOL-3-YLBENZAZOLES, THEIR USE AS HERBICIDES OR DESICCANTS/DEFOLIANTS, AND THEIR PREPARATION

This application is a 371 of PCT/EP97/06715 filed Dec. 1, 1997.

The present invention relates to novel substituted pyrazol-3-ylbenzazoles of the formula I

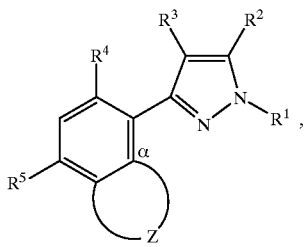

where:

$R^1$ is hydrogen, $C_1$–$C_4$-alkyl or $C_1$–$C_4$-haloalkyl;

$R^2$ is cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfinyl, $C_1$–$C_4$-haloalkylsulfinyl, $C_1$–$C_4$-alkylsulfonyl or $C_1$–$C_4$-haloalkylsulfonyl;

$R^3$ is hydrogen, halogen, cyano, nitro, $C_1$–$C_4$-alkyl or $C_1$–$C_4$-haloalkyl;

$R^4$ is hydrogen or halogen; $R^5$ is hydrogen, halogen, cyano, $C_1$–$C_4$-alkyl, $C_1$–$C_4$-haloalkyl, $C_1$–$C_4$-alkoxy or $C_1$–$C_4$-haloalkoxy;

Z is a group —NC=C($XR^6$)—O— or —N=C($XR^6$)—S— which may be bonded to α via the nitrogen, oxygen or sulfur;

X is a chemical bond, oxygen, sulfur, —S(O)—, —SO$_2$—, —NH— or —NC$_1$($R^7$)—;

$R^6$ and $R^7$ independently of one another are each $C_1$–$C_6$-alkyl, $C_1$–$C_6$-haloalkyl, cyano-$C_1$–$C_4$-alkyl, hydroxy-$C_1$–$C_4$-alkyl, $C_3$–$C_6$-alkenyl, cyano-$C_3$–$C_6$-alkenyl, $C_3$–$C_6$-haloalkenyl, $C_3$–$C_6$-alkynyl, cyano-$C_3$–$C_6$-alkynyl, $C_3$–$C_6$-haloalkynyl, $C_1$–$C_4$-alkoxy-$C_1$–$C_4$-alkyl, $C_1$–$C_4$-haloalkoxy-$C_1$–$C_4$-alkyl, $C_3$–$C_4$-alkenyloxy-$C_1$–$C_4$-alkyl, $C_3$–$C_4$-alkynyloxy-$C_1$–$C_4$-alkyl, $C_3$–$C_8$-cycloalkyloxy-$C_1$–$C_4$-alkyl, amino-$C_1$–$C_4$-alkyl, $C_1$–$C_4$-alkylamino-$C_1$–$C_4$-alkyl, di($C_1$–$C_4$-alkyl)amino-$C_1$–$C_4$-alkyl, $C_1$–$C_4$-alkylthio-$C_1$–$C_4$-alkyl, $C_1$–$C_4$-haloalkylthio-$C_1$–$C_4$-alkyl, $C_3$–$C_4$-alkenylthio-$C_1$–$C_4$-alkyl, $C_3$–$C_4$-alkynylthio-$C_1$–$C_4$-alkyl, $C_1$–$C_4$-alkylsulfinyl-$C_1$–$C_4$-alkyl, $C_1$–$C_4$-haloalkylsulfinyl-$C_1$–$C_4$-alkyl, $C_3$–$C_4$-alkenylsulfinyl-$C_1$–$C_4$-alkyl, $C_3$–$C_4$-alkynylsulfinyl-$C_1$–$C_4$-alkyl, $C_1$–$C_4$-alkyl-sulfonyl-$C_1$–$C_4$-alkyl, $C_1$–$C_4$-haloalkylsulfonyl-$C_1$–$C_4$-alkyl, $C_3$–$C_4$-alkenylsulfonyl-$C_1$–$C_4$-alkyl, $C_3$–$C_4$-alkynylsulfonyl-$C_1$–$C_4$-alkyl, hydroxycarbonyl-$C_1$–$C_4$-alkyl, ($C_1$–$C_4$-alkoxy)-carbonyl-$C_1$–$C_4$-alkyl which may carry a cyano or ($C_1$–$C_4$-alkoxy)carbonyl group, ($C_1$–$C_4$-alkylthio)carbonyl-$C_1$–$C_4$-alkyl, aminocarbonyl-$C_1$–$C_4$-alkyl, $C_1$–$C_4$-alkylaminocarbonyl-$C_1$–$C_4$-alkyl, di($C_1$–$C_4$-alkyl)aminocarbonyl-$C_1$–$C_4$-alkyl, di($C_1$–$C_4$-alkyl) phosphonyl-$C_1$–$C_4$-alkyl, ($C_1$–$C_4$-alkoxy)imino-$C_1$–$C_4$-alkyl, ($C_3$–$C_4$-alkenyloxy)imino-$C_1$–$C_4$-alkyl, $C_3$–$C_8$-cycloalkyl, $C_3$–$C_8$-cycloalkyl-$C_1$–$C_4$-alkyl, phenyl, phenyl-$C_1$–$C_4$-alkyl, 3- to 7-membered heterocyclyl or heterocyclyl-$C_1$–$C_4$-alkyl, where each cycloalkyl and each heterocyclyl ring may contain a carbonyl or thiocarbonyl ring member, and where each cycloalkyl, phenyl and heterocyclyl ring may be unsubstituted or carry one to four substituents selected in each case from the group consisting of cyano, nitro, amino, hydroxyl, carboxyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, ($C_1$–$C_4$-alkoxy)carbonyl, ($C_1$–$C_4$-alkyl)carbonyl, ($C_1$–$C_4$-haloalkyl)carbonyl, ($C_1$–$C_4$-alkyl)carbonyloxy, ($C_1$–$C_4$-haloalkyl)carbonyloxy and di($C_1$–$C_4$-alkyl)amino;

if x is a chemical bond, oxygen, sulfur, —NH— or —N($R^7$)—, $R^6$ may also be ($C_1$–$C_4$-alkyl)carbonyl, ($C_1$–$C_4$-haloalkyl)carbonyl, ($C_1$–$C_4$-alkoxy)carbonyl, $C_1$–$C_4$-alkylsulfonyl or $C_1$–$C_4$-haloalkylsulfonyl;

if X is a chemical bond, $R^6$ may furthermore be hydrogen, cyano, mercapto, amino, halogen, —CH$_2$—CH(halogen)-$R_8$, —CH=CH—$R^8$ or —CH=C(halogen)-$R^8$, where $R^8$ is hydroxycarbonyl, ($C_1$–$C_4$-alkoxy)carbonyl, ($C_1$–$C_4$-alkylthio)carbonyl, aminocarbonyl, $C_1$–$C_4$-alkylaminocarbonyl, di($C_1$–$C_4$-alkyl)-aminocarbonyl or di($C_1$–$C_4$-alkyl)phosphonyl, or $R^6$ and $R^7$ together are a 1,3-propylene, tetramethylene, pentamethylene or ethyleneoxyethylene chain which may in each case be unsubstituted or carry one to four $C_1$–$C_4$-alkyl groups or one or two ($C_1$–$C_4$-alkoxy)carbonyl groups, and the agriculturally useful salts of these compounds I.

The invention further relates to the use of compounds I as herbicides and/or for the desiccation/defoliation of plants, herbicidal compositions and compositions for the desiccation and/or defoliation of plants which comprise the compounds I as active compounds, processes for preparing the compounds I and herbicidal compositions and compositions for the desiccation/defoliation of plants using the compounds I, and methods for controlling undesirable vegetation and for the desiccation/defoliation of plants using the compounds I.

Certain aryl pyrazoles, where, in addition to phenyl, various benzoheterocyclyl radicals are also mentioned in principle as aryl radicals, are already described as herbicides in patent applications WO 92/02509, WO 92/06962, WO 86/01255, WO 96/15115, WO 96/15116 and WO 96/40643.

Furthermore, the general formula of WO 96/01254 embraces, when the substituents are chosen appropriately, inter alia compounds of the formula II

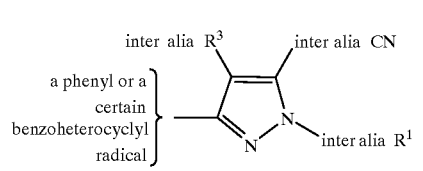

who are also said to have herbicidal activity.

It is an object of the present invention to provide novel herbicidally active pyrazole compounds which allow better selective control of undesirable plants than known compounds. It is a further object to provide novel compounds which have a desiccant/defoliant action.

We have found that these objects are achieved by the present substituted pyrazol-3-ylbenzazoles of the formula I.

Furthermore, we have found herbicidal compositions which comprise the compounds I and have a very good herbicidal activity. Moreover, we have found processes for preparing these compositions and methods for controlling undesirable vegetation using the compounds I.

Furthermore, we have found that the compounds I are also suitable for the desiccation/defoliation of parts of plants, suitable plants being crop plants such as cotton, potatoes, oilseed rape, sunflower, soybean or field beans, in particular cotton. In this regard, we have found compositions for the desiccation and/or defoliation of plants, processes for preparing these compositions and methods for the desiccation and/or defoliation of plants using the compounds I.

Depending on the substitution pattern, the compounds of the formula I can contain one or more chiral centers, in which case they exist in the form of enantiomer or diastereomer mixtures. The invention relates to the pure enantiomers or diastereomers and also to mixtures thereof.

The organic moieties mentioned in the definition of the substituents $R^1$ to $R^3$ and $R^5$ to $R_8$ or as radicals on cycloalkyl, phenyl or heterocyclic rings are—like the term halogen—collective terms for individual listings of the individual group members. All carbon chains, ie. all the alkyl, haloalkyl, cyanoalkyl, oxyalkyl, aminoalkyl, oxycarbonylalkyl, aminocarbonylalkyl, phosphonylalkyl, oxyaminoalkyl, phenylalkyl, heterocyclylalkyl, alkenyl, haloalkenyl, cyanoalkenyl, alkynyl, haloalkynyl and cyanoalkynyl moieties, can be straight-chain or branched. Halogenated substituents preferably carry one to five identical or different halogens. The term halogen represents in each case fluorine, chlorine, bromine or iodine.

Other examples of meanings are:

$C_1$–$C_4$-alkyl: $CH_3$, $C_2H_5$, n-propyl, $CH(CH_3)_2$, n-butyl, 1-methylpropyl, 2-methylpropyl and $C(CH_3)_3$;

$C_1$–$C_4$-haloalkyl: a $C_1$–$C_4$-alkyl radical as mentioned above which is partially or fully substituted by fluorine, chlorine, bromine and/or iodine, ie. for example $CH_2F$, $CHF_2$, $CF_3$, $CH_2Cl$, $CH(Cl)_2$, $C(Cl)_3$, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, $C_2F_5$, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, 1-fluoromethyl-2-fluoroethyl, 1-chloromethyl-2-chloroethyl, 1-bromomethyl-2-bromoethyl, 4-fluorobutyl, 4-chlorobutyl, 4-bromobutyl or nonafluorobutyl;

$C_1$–$C_6$-alkyl: $C_1$–$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably $CH_3$, $C_2H_5$, $CH_2$–$C_2H_5$, $CH(CH_3)_2$, n-butyl, $C(CH_3)_3$, n-pentyl or n-hexyl;

$C_1$–$C_6$-haloalkyl: a $C_1$–$C_6$-alkyl radical as mentioned above which is partially or fully substituted by fluorine, chlorine, bromine and/or iodine, ie. for example one of the radicals mentioned under $C_1$–$C_4$-haloalkyl, and also 5-fluoro-1-pentyl, 5-chloro-1-pentyl, 5-bromo-1-pentyl, 5-iodo-1-pentyl, 5,5,5-trichloro-1-pentyl, undecafluoropentyl, 6-fluoro-1-hexyl, 6-chloro-1-hexyl, 6-bromo-1-hexyl, 6-iodo-1-hexyl, 6,6,6-trichloro-1-hexyl or dodecafluorohexyl;

cyano-$C_1$–$C_4$-alkyl: $CH_2CN$, 1-cyanoethyl, 2-cyanoethyl, 1-cyanoprop-1-yl, 2-cyanoprop-1-yl, 3-cyanoprop-1-yl, 1-cyanobut-1-yl, 2-cyanobut-1-yl, 3-cyanobut-1-yl, 4-cyanobut-1-yl, 1-cyanobut-2-yl, 2-cyanobut-2-yl, 3-cyanobut-2-yl, 4-cyanobut-2-yl, 1-($CH_2CN$)eth-1-yl, 1-($CH_2CN$)-1-($CH_3$)eth-1-yl or 1-($CH_2CN$)prop-1-yl;

hydroxy-$C_1$–$C_4$-alkyl: $CH_2OH$, 1-hydroxyethyl, 2-hydroxyethyl, 1-hydroxyprop-1-yl, 2-hydroxyprop-1-yl, 3-hydroxyprop-1-yl, 1-hydroxybut-1-yl, 2-hydroxybut-1-yl, 3-hydroxybut-1-yl, 4-hydroxybut-1-yl, 1-hydroxybut-2-yl, 2-hydroxybut-2-yl, 3-hydroxybut-2-yl, 4-hydroxybut-2-yl, 1-($CH_2OH$)eth-1-yl, 1-($CH_2OH$)-$C_1$-($CH_3$)eth-1-yl or $C_1$-($CH_2OH$)prop-1-yl;

amino-$C_1$–$C_4$-alkyl: $CH_2NH_2$, 1-aminoethyl, 2-aminoethyl, 1-aminoprop-1-yl, 2-aminoprop-1-yl, 3-aminoprop-1-yl, 1-aminobut-1-yl, 2-aminobut-1-yl, 3-aminobut-1-yl, 4-aminobut-1-yl, 1-aminobut-2-yl, 2-aminobut-2-yl, 3-aminobut-2-yl, 4-aminobut-2-yl, 1-($CH_2NH_2$)eth-1-yl, 1-($CH_2NH_2$)-1-($CH_3$)eth-1-yl or $C_1$I-($CH_2NH_2$)prop-1-yl;

hydroxycarbonyl-$C_1$–$C_4$-alkyl: $CH_2COOH$, 1-(COOH)ethyl, 2-(COOH)ethyl, 1-(COOH)prop-1-yl, 2-(COOH)prop-1-yl, 3-(COOH)-prop-1-yl, 1-(COOH)but-1-yl, 2-(COOH)but-1-yl, 3-(COOH)but-1-yl, 4-(COOH)but-1-yl, 1-(COOH)but-2-yl, 2-(COOH)but-2-yl, 3-(COOH)but-2-yl, 4-(COOH)but-2-yl, 1-($CH_2COOH$)eth-1-yl, 1-($CH_2COOH$)-1-($CH_3$)eth-1-yl or 1-($CH_2COOH$)prop-1-yl;

aminocarbonyl-$C_1$–$C_4$-alkyl: $CH_2CONH_2$, 1-($CONH_2$)ethyl, 2-($CONH_2$)ethyl, 1-($CONH_2$)prop-1-yl, 2-($CONH_2$)prop-1-yl, 3-($CONH_2$)prop-1-yl, 1-($CONH_2$)but-1-yl, 2-($CONH_2$)but-1-yl, 3-($CONH_2$)but-1-yl, 4-($CONH_2$)but-1-yl, 1-($CONH_2$)but-2-yl, 2-($CONH_2$)but-2-yl, 3-($CONH_2$)but-2-yl, 4-($CONH_2$)but-2-yl, 1-($CH_2CONH_2$)eth-1-yl, 1-($CH_2CONH_2$)-1-(CH3)eth-1-yl or 1-($CH_2CONH_2$) prop-1-yl;

phenyl-$C_1$–$C_4$-alkyl: benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 2-phenylbut-2-yl, 2-phenylbut-2-yl, 3-phenylbut-2-yl, 4-phenylbut-2-yl, 1-benzyleth-1-yl, 1-benzyl-1-methyleth-1-yl or 1-benzylprop-1-yl, preferably benzyl or 2-phenylethyl;

heterocyclyl-$C_1$–$C_4$-alkyl: heterocyclylmethyl, 1-heterocyclylethyl, 2-heterocyclylethyl, 1-heterocyclylprop-1-yl, 2-heterocyclylprop-1-yl, 3-heterocyclylprop-1-yl, 1-heterocyclylbut-1-yl, 2-heterocyclylbut-1-yl, 3-heterocyclylbut-1-yl, 4-heterocyclylbut-1-yl, 1-heterocyclylbut-2-yl, 2-heterocyclylbut-2-yl, 3-heterocyclylbut-2-yl, 3-heterocyclylbut-2-yl [sic], 4-heterocyclylbut-2-yl, 1-(heterocyclylmethyl)eth-1-yl, 1-(heterocyclylmethyl)-1-(methyl)eth-1-yl or 1-(heterocyclylmethyl)prop-1-yl, preferably heterocyclylmethyl or 2-heterocyclylethyl;

$C_1$–$C_4$-alkoxy: $OCH_3$, $OC_2H_5$, $OCH_2$—$C_2H_5$, $OCH(CH_3)_2$, n-butoxy, $OCH(CH_3)$—$C_2H_5$, $OCH_2$—$CH(CH_3)_2$ or $C(CH_3)_3$, preferably $OCH_3$, $OC_2H_5$ or $OCH(CH_3)_2$;

$C_1$–$C_4$-haloalkoxy: a $C_1$–$C_4$-alkoxy radical as mentioned above which is partially or fully substituted by fluorine, chlorine, bromine and/or iodine, ie. for example $OCH_2F$, $OCHF_2$, $OCF_3$, $OCH_2Cl$, $OCH(Cl)_2$, $OC(Cl)_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2- fluoro- ethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy, preferably $OCHF_2$, $OCF_3$, dichlorofluoromethoxy, chlorodifluoromethoxy or 2,2,2-trifluoroethoxy;

$C_1$–$C_4$-alkylthio: $SCH_3$, $SC_2H_5$, $SCH_2$—$C_2H_5$, SCH$(CH_3)_2$, n-butylthio, 1-methylpropylthio, $SCH_2$—$CH(CH_3)_2$ or $SC(CH_3)_3$, preferably $SCH_3$ or $SC_2H_5$;

$C_1$–$C_4$-haloalkylthio: a $C_1$–$C_4$-alkylthio radical as mentioned above which is partially or fully substituted by fluorine, chlorine, bromine and/or iodine, ie. for example $SCH_2F$, $SCHF_2$, $SCF_3$, $SCH_2Cl$, $SCH(Cl)_2$, $SC(Cl)_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, $SC_2F_5$, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio, 1-($CH_2Br$)-2-bromoethylthio, 4-fluorobutylthio, 4-chlorobutylthio, 4-bromobutylthio or $SCF_2$—$CF_2$—$C_2F_5$, preferably $SCHF_2$, $SCF_3$, dichlorofluoromethylthio, chlorodifluoromethylthio or 2,2,2-trifluoroethylthio;

$C_1$–$C_4$-alkoxy-$C_1$–$C_4$-alkyl: $C_1$–$C_4$-alkyl which is substituted by $C_1$–$C_4$-alkoxy as mentioned above, ie. for example $CH_2$—$OCH_3$, $CH_2$-$OC_2H_5$, n-propoxymethyl, $CH_2$-$OCH(CH_3)_2$, n-butoxymethyl, (1-methylpropoxy)methyl, (2-methylpropoxy)methyl, $CH_2$-$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(Cl-methylethoxy)butyl, 4-(n-butoxy)butyl, 4-(1-methylpropoxy)butyl, 4-(2-methylpropoxy)butyl or 4-(1,1-dimethylethoxy)butyl, preferably $CH_2$—$OCH_3$, $CH_2$—$OC_2H_5$, 2-($OCH_3$)ethyl or 2-($OC_2ClH_5$)ethyl;

$C_1$–$C_4$-haloalkoxy-$C_1$–$C_4$-alkyl: $C_1$–$C_4$-alkyl which is substituted by $C_1$–$C_4$-haloalkoxy as mentioned above, ie. for example 2-($OCHF_2$)ethyl, 2-($OCF_3$)ethyl or 2-($OC_2F_5$)ethyl;

$C_1$–$C_4$-alkylthio-$C_1$–$C_4$-alkyl: $C_1$–$C_4$-alkyl which is substituted by $C_1$–$C_4$-alkylthio as mentioned above, ie. for example $CH_2$—$SCH_3$, $CH_2$—$SC_2H_5$, n-propylthiomethyl, $CH_2$—$SCH(CH_3)_2$, n-butylthiomethyl, (1-methylpropylthio)methyl, (2-methylpropylthio)methyl, $CH_2$—$SC(CH_3)_3$, 2-(methylthio)ethyl, 2-(ethylthio)ethyl, 2-(n-propylthio)ethyl, 2-(1-methylethylthio)ethyl, 2-(n-butylthio)ethyl, 2-(1-methylpropylthio)ethyl, 2-(2-methylpropylthio)ethyl, 2-(1,1-dimethylethylthio)ethyl, 2-(methylthio)propyl, 2-(ethylthio)propyl, 2-(n-propylthio)propyl, 2-(1-methylethylthio)propyl, 2-(n-butylthio)propyl, 2-(1-methylpropylthio)propyl, 2-(2-methylpropylthio)propyl, 2-(1,1-dimethylethylthio)propyl, 3-(methylthio)propyl, 3-(ethylthio)propyl, 3-(n-propylthio)propyl, 3-(1-methylethylthio)propyl, 3-(n-butylthio)propyl, 3-(1-methylpropylthio)propyl, 3-(2-methylpropylthio)propyl, 3-(1,1-dimethylethylthio)propyl, 2-(methylthio)butyl, 2-(ethylthio)butyl, 2-(n-propylthio)butyl, 2-(1-methylethylthio)butyl, 2-(n-butylthio)butyl, 2-(1-methylpropylthio)butyl, 2-(2-methylpropylthio)butyl, 2-(1,1-dimethylethylthio)butyl, 3-(methylthio)butyl, 3-(ethylthio)butyl, 3-(n-propylthio)butyl, 3-(1-methylethylthio)butyl, 3-(n-butylthio)butyl, 3-(1-methylpropylthio)butyl, 3-(2-methylpropylthio)butyl, 3-(1,1-dimethylethylthio)butyl, 4-(methylthio)butyl, 4-(ethylthio)butyl, 4-(n-propylthio)butyl, 4-(1-methylethylthio)butyl, 4-(n-butylthio)butyl, 4-(1-methylpropylthio)butyl, 4-(2-methylpropylthio)butyl or 4-(1,1-dimethylethylthio)butyl, preferably $CH_2$—$SCH_3$, $CH_2$—$SC_2H_5$, 2-($SCH_3$)ethyl or 2-($SC_2H_5$)ethyl;

$C_1$–$C_4$-haloalkylthio-$C_1$–$C_4$-alkyl: $C_1$–$C_4$-alkyl which is substituted by $C_1$–$C_4$-haloalkylthio as mentioned above, ie. for example 2-($SCHF_2$)ethyl, 2-($SCF_3$)ethyl or 2-($SC_2F_5$)ethyl;

($C_1$–$C_4$-alkoxy)imino-$C_1$–$C_4$-alkyl: $C_1$–$C_4$-alkyl which is substituted by ($C_1$–$C_4$-alkoxy)imino such as =N—$CH_3$, =N—$C_2H_5$, =$NCH_2$—$C_2H_5$, =N—$CH(CH_3)_2$, =$NCH_2$—$CH_2$—$C_2H_5$, =$NCH(CH_3)$—$C_2H_5$, =$NCH_2$—$CH(CH_3)_2$ or =N—$C(CH_3)_3$ ie. for example CH=N—$CH_3$, CH=N—$C_2H_5$, $CH_2$—CH=N—$CH_3$ or $CH_2$—CH=N—$C_2H_5$;

($C_1$–$C_4$-alkyl)carbonyl: CO—$CH_3$, CO—$C_2H_5$, CO—$CH_2$—$C_2H_5$, CO—$CHC_1(CH_3)_2$, n-butylcarbonyl, CO—$CH(CH_3)$—$C_2H_5$, CO—$CH_2$—$CH(CH_3)_2$ or CO—C$(CH_3)_3$, preferably CO—$CH_3$ or CO—$C_2H_5$;

($C_1$–$C_4$-haloalkyl)carbonyl: a ($C_1$–$C_4$-alkyl)carbonyl radical as mentioned above which is partially or fully substituted by fluorine, chlorine, bromine and/or iodine, ie. for example CO—$CH_2F$, CO—$C_1HF_2$, CO—$CF_3$, CO—$CH_2C_1$, CO—$CH(C_1)_2$, CO—$C(C_1)_3$, chlorofluoromethylcarbonyl, dichlorofluoromethylcarbonyl, chlorodifluoromethylcarbonyl, 2-fluoroethylcarbonyl, 2-chloroethylcarbonyl, 2-bromoethylcarbonyl, 2-iodoethylcarbonyl, 2,2-difluoroethylcarbonyl, 2,2,2-trifluoroethylcarbonyl, 2-chloro-2-fluoroethylcarbonyl, 2-chloro-2,2-difluoroethylcarbonyl, 2,2-dichloro-2-fluoroethylcarbonyl, 2,2,2-trichloroethylcarbonyl, CO—$C_2F_5$, 2-fluoropropylcarbonyl, 3-fluoropropylcarbonyl, 2,2-difluoropropylcarbonyl, 2,3-difluoropropylcarbonyl, 2-chloropropylcarbonyl, 3-chloropropylcarbonyl, 2,3-dichloropropylcarbonyl, 2-bromopropylcarbonyl, 3-bromopropylcarbonyl, 3,3,3-trifluoropropylcarbonyl, 3,3,3-trichloropropylcarbonyl, CO—$CH_2$—$C_2F_5$, CO—$CF_2$—$C_2F_5$, 1-($CH_2F$)-2-fluoroethylcarbonyl, 1-($CH_2Cl$)-2-chloroethylcarbonyl, 1-($CH_2Br$)-2-bromoethylcarbonyl, 4-fluorobutylcarbonyl, 4-chlorobutylcarbonyl, 4-bromobutylcarbonyl or nonafluorobutylcarbonyl, preferably CO—$CF_3$, CO—$CH_2C_1$or 2,2,2-trifluoroethylcarbonyl;

($C_1$–$C_4$ -alkyl)carbonyloxy: O—CO—$CH_3$, O—CO—$C_2H_5$, O—CO—$CH_2$—$C_2H_5$, O—CO—$CH(CH_3)_2$, O—CO—$CH_2$—$CH_2$—$C_2H_5$, O—CO—$CH(CH_3)$—$C_2H_5$, O—CO—$CH_2$—$CH(CH_3)_2$ or O—CO—$C(CH_3)_3$, preferably O—CO—$CH_3$ or O—CO—$C_2H_5$;

($C_1$–$C_4$-haloalkyl)carbonyloxy: a ($C_1$–$C_4$-alkyl)carbonyl radical as mentioned above which is partially or fully substituted by fluorine, chlorine, bromine and/or iodine, ie. for example O—CO—$CH_2$F, O—CO—$CHF_2$, O—CO—$CF_3$, O—CO—$CH_2C_1$, O—CO—$CH(C_1)_2$, O—CO—C$(C_1)_3$, chlorofluoromethylcarbonyloxy, dichlorofluoromethylcarbonyloxy, chlorodifluoromethylcarbonyloxy, 2-fluoroethylcarbonyloxy, 2-chloroethylcarbonyloxy, 2-bromoethylcarbonyloxy, 2-iodoethylcarbonyloxy, 2,2-difluoroethylcarbonyloxy, 2,2,2-trifluoroethylcarbonyloxy, 2-chloro-2-fluoroethylcarbonyloxy, 2-chloro-2,2-difluoroethylcarbonyloxy, 2,2-dichloro-2-fluoroethylcarbonyloxy, 2,2,2-trichloroethylcarbonyloxy, O—CO—$C_2F_5$, 2-fluoropropylcarbonyloxy, 3-fluoropropylcarbonyloxy, 2,2-difluoropropylcarbonyloxy, 2,3-difluoropropylcarbonyloxy, 2-chloropropylcarbonyloxy, 3-chloropropylcarbonyloxy, 2,3-dichloropropylcarbonyloxy, 2-bromopropylcarbonyloxy, 3-bromopropylcarbonyloxy, 3,3,3-trifluoropropylcarbonyloxy, 3,3,3-trichloropropylcarbonyloxy, O—CO—$CH_2$—$C_2F_5$, O—CO—$CF_2$—$C_2F_5$, 1-($CH_2$F)-2-fluoroethylcarbonyloxy, 1-($CH_2$Cl)-2-chloroethylcarbonyloxy, 1-($CH_2$Br)-2-bromoethylcarbonyloxy, 4-fluorobutylcarbonyloxy, 4-chlorobutylcarbonyloxy, 4-bromobutylcarbonyloxy or nonafluorobutylcarbonyloxy, preferably O—CO—$CF_3$, O—CO—$CH_2$Cl or 2,2,2-trifluoroethylcarbonyloxy;

($C_1$–$C_4$-alkoxy)carbonyl: CO—$OCH_3$, CO—$OC_2H_5$, n-propoxycarbonyl, CO—$OCH(CH_3)_2$, n-butoxycarbonyl, CO—$OCH(CH_3)$—$C_2H_5$, CO—$OCH_2$—$CH(CH_3)_2$ or CO—$OC(CH_3)_3$, preferably CO—$OCH_3$ or CO—$OC_2H_5$;

($C_1$–$C_4$-alkoxy)carbonyl-$C_1$–$C_4$-alkyl: $C_1$–$C_4$-alkyl which is substituted by ($C_1$–$C_4$-alkoxy)carbonyl as mentioned above, ie. for example $CH_2$—CO—$OCH_3$, $CH_2$—CO—$OC_2H_5$, n-propoxycarbonylmethyl, $CH_2$—CO—$OCH(CH_3)_2$, n-butoxycarbonylmethyl, $CH_2$—CO—$OCH(CH_3)$—$C_2H_5$, $CH_2$—CO—$OCH_2$—$CH(CH_3)_2$, $CH_2$—CO—$OC(CH_3)_3$, 1-(methoxycarbonyl)ethyl, 1-(ethoxycarbonyl)ethyl, 1-(n-propoxycarbonyl)ethyl, 1-(1-methylethoxycarbonyl)ethyl, 1-(n-butoxycarbonyl)ethyl, 2-(methoxycarbonyl)ethyl, 2-(ethoxycarbonyl)ethyl, 2-(n-propoxycarbonyl)ethyl, 2-(1-methylethoxycarbonyl)ethyl, 2-(n-butoxycarbonyl)ethyl, 2-(l-methylpropoxycarbonyl)ethyl, 2-(2-methylpropoxycarbonyl)ethyl, 2-(1,1-dimethylethoxycarbonyl)ethyl, 2-(methoxycarbonyl)propyl, 2-(ethoxycarbonyl)propyl, 2-(n-propoxycarbonyl)propyl, 2-(1-methylethoxycarbonyl)propyl, 2-(n-butoxycarbonyl)propyl, 2-(1-methylpropoxycarbonyl)propyl, 2-(2-methylpropoxycarbonyl)propyl, 2-(1,1-dimethylethoxycarbonyl)propyl, 3-(methoxycarbonyl)propyl, 3-(ethoxycarbonyl)propyl, 3-(n-propoxycarbonyl)propyl, 3-(1-methylethoxycarbonyl)propyl, 3-(n-butoxycarbonyl)propyl, 3-(1-methylpropoxycarbonyl)propyl, 3-(2-methylpropoxycarbonyl)propyl, 3-(1,1-dimethylethoxycarbonyl)propyl, 2-(methoxycarbonyl)butyl, 2-(ethoxycarbonyl)butyl, 2-(n-propoxycarbonyl)butyl, 2-(1-methylethoxycarbonyl)butyl, 2-(n-butoxycarbonyl)butyl, 2-(1-methylpropoxycarbonyl)butyl, 2-(2-methylpropoxycarbonyl)butyl, 2-(1,1-dimethylethoxycarbonyl)butyl, 3-(methoxycarbonyl)butyl, 3-(ethoxycarbonyl)butyl, 3-(n-propoxycarbonyl)butyl, 3-(1-methylethoxycarbonyl)butyl, 3-(n-butoxycarbonyl)butyl, 3-(1-methylpropoxycarbonyl)butyl, 3-(2-methylpropoxycarbonyl)butyl, 3-(1,1-dimethylethoxycarbonyl)butyl, 4-(methoxycarbonyl)butyl, 4-(ethoxycarbonyl)butyl, 4-(n-propoxycarbonyl)butyl, 4-(1-methylethoxycarbonyl)butyl, 4-(n-butoxycarbonyl)butyl, 4-(1-methylpropoxycarbonyl)butyl, 4-(2-methylpropoxycarbonyl)butyl or 4-(1,1-dimethylethoxycarbonyl)butyl, preferably $CH_2$—CO—$OCH_3$, $CH_2$—CO—$OC_2H_5$, 1-(methoxycarbonyl)ethyl or 1-(ethoxycarbonyl)ethyl;

($C_1$–$C_4$-alkylthio)carbonyl: CO—$SCH_3$, CO—$SC_2H_5$, CO—$SCH_2$—$C_2H_5$, CO—$SCH(CH_3)_2$, CO—$SCH_2CH_2$—$C_2$HS, CO—$SCH(CH_3)$—$C_2H_5$, CO—$SCH_2$—$CH(CH_3)_2$ or CO—$SC(CH_3)_3$, preferably CO—$SCH_3$ or CO—$SC_2H_5$;

($C_1$–$C_4$-alkylthio)carbonyl-$C_1$–$C_4$-alkyl: $C_1$–$C_4$-alkyl which is substituted by ($C_1$–$C_4$-alkylthio)carbonyl as mentioned above, ie. for example $CH_2$—CO—$SCH_3$, $CH_2$—CO—$SC_2H_5$, $CH_2$—CO—$SCHS$—$C_2H_5$ [sic], $CH_2$—CO—$SCH(CH_3)_2$, $CH_2$—CO—$SCH_2CH_2$—$C_2H_5$, $CH_2$—CO—$SCH(CH_3)$—$C_2H_5$, $CH_2$—CO—$SCH_2$—$CH(CH_3)_2$, $CH_2$—CO—$SC(CH_3)_3$, 1-(CO—$SCH_3$)ethyl, 1-(CO—$SC_2H_5$)ethyl, 1-(CO—$SCH_2$—$C_2H_5$)ethyl, 1-[CO—$SCH(CH_3)_2$]ethyl, 1-(CO—$SCH_2CH_2$—$C_2H_5$)ethyl, 1-[CO—SCH$(CH_3)$—$C_2H_5$]ethyl, 1-[CO—$SCH_2$—$CH(CH_3)_2$]ethyl, 1-[CO—$SC(CH_3)_3$]ethyl, 2-(CO—$SCH_3$)ethyl, 2-(CO—$SC_2H_5$)ethyl, 2-(CO—$SCH_2$—$C_2$Cl $H_5$)ethyl, 2-CO—SCH$(CH_3)_2$]ethyl, 2-(CO—$SCH_2CH_2$—$C_2H_5$)ethyl, 2-[CO—$SCH(CH_3)$—$C_2H_5$]ethyl, 2-[CO—$SCH_2$—$CH(CH_3)_2$]ethyl, 2-[CO—$SC(CH_3)_3$]ethyl, 2-(CO—$SCH_3$)-propyl, 2-(CO—$SC_2H_5$)propyl, 2-(CO—$SCH_2$—$C_2H_5$)propyl, 2-[CO—$SCH(CH_3)_2$]propyl, 2-(CO—$SCH_2CH_2$—$C_2H_5$) propyl, 2-[CO—$SCH(CH_3)$—$C_2H_5$]propyl, 2-[CO—$SCH_2$—$CH(CH_3)_2$]propyl, 2-[CO—$SC(CH_3)_3$]propyl, 3-(CO—$SCH_3$)propyl, 3-(CO—$SC_2H_5$)propyl, 3-(CO—$SCH_2$—$C_2H_5$)propyl, 3-[CO—$SCH(CH_3)_2$]propyl, 3-(CO—$SCH_2CH_2$—$C_2H_5$)propyl, 3-[CO—$SCH(CH_3)$—$C_2H_5$]propyl, 3-[CO—$SCH_2$—$CH(CH_3)_2$]propyl, 3-[CO—$SC(CH_3)_3$]propyl, 2-(CO—$SCH_3$)butyl, 2-(CO—$SC_2H_5$) butyl, 2-(CO—$SCH_2$—$C_2H_5$)butyl, 2-[CO—$SCH(CH_3)_2$] butyl, 2-(CO—$SCH_2CH_2$—$C_2H_5$)butyl, 2-[CO—SCH$(CH_3)$—$C_2H_5$]butyl, 2-[CO—$SCH_2$—$CH(CH_3)_2$]butyl, 2-[CO—$SC(CH_3)_3$]butyl, 3-(CO—$SCH_3$)butyl, 3-(CO—$SC_2H_5$)butyl, 3-(CO—$SCH_2$—$C_2H_5$)butyl, 3-[CO—SCH$(CH_3)_2$]butyl, 3-(CO—$SCH_2CH_2$—$C_2H_5$)butyl, 3-[CO—SCH$(CH_3)$—$C_2H_5$]butyl, 3-[CO—$SCH_2$—$CH(CH_3)_2$] butyl, 3-[CO—$SC(CH_3)_3$]butyl, 4-(CO—$SCH_3$)- butyl, 4-(CO—$SC_2H_5$)butyl, 4-(CO—$SCH_2$—$C_2H_5$)butyl, 4-[CO—$SCH(CH_3)_2$]butyl, 4-(CO—$SCH_2CH_2$—$C_2H_5$)butyl, 4-[CO—$SCH(CH_3)$—$C_2H_5$]butyl, 4-[CO—$SCH_2$—CH$(CH_3)_2$]butyl or 4-[CO—$SC(CH_3)_3$]butyl, preferably $CH_2$—CO—$SCH_3$, $CH_2$—CO—$SC_2H_5$, 1-(CO—$SCH_3$)ethyl or 1-(CO—$SC_2H_5$)ethyl;

$C_1$–$C_4$-alkylsulfinyl: SO—$CH_3$, SO—$C_2H_5$, SO—$CH_2$—$C_2$HS, SO—$CH(CH_3)$2, n-butylsulfinyl, SO—$CH(CH_3)$—$C_2H_5$, SO—$CH_2$—$CH(CH_3)_2$ or SO—$C(CH_3)_3$, preferably SO—$CH_3$ or SO—$C_2H_5$;

$C_1$–$C_4$-haloalkylsulfinyl: a $C_1$–$C_4$-alkylsulfinyl radical as mentioned above which is partially or fully substituted by fluorine, chlorine, bromine and/or iodine, ie. for example SO—$CH_2$F, SO—$CHF_2$, SO—$CF_3$, SO—$CH_2$Cl, SO—CH$(C_1)_2$, SO—C$(C_1)_3$, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl, SO—$C_2F_5$, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, SO—$CH_2$—$C_2F_5$, SO—$CF_2$—$C_2F_5$, 1-($CH_2F$)-2-fluoroethylsulfinyl, 1-($CH_2Cl$)-2-chloroethylsulfinyl, 1-($CH_2Br$)-2-bromoethylsulfinyl, 4-fluorobutylsulfinyl, 4-chlorobutylsulfinyl, 4-bromobutylsulfinyl or nonafluorobutylsulfinyl, preferably SO—$CF_3$, SO—$CH_2Cl$ or 2,2,2-trifluoroethylsulfinyl;

$C_1$–$C_4$-alkylsulfinyl-$C_1$–$C_4$-alkyl: $C_1$–$C_4$-alkyl which is substituted by $C_1$–$C_4$-alkylsulfinyl as mentioned above, ie. for example $CH_2SOCH_3$, $CH_2SOC_2H_5$, n-propylsulfinylmethyl, $CH_2SOCH(CH_3)_2$, n-butylsulfinylmethyl, (1-methylpropylsulfinyl)methyl, (2-methylpropylsulfinyl)methyl, (1,1-dimethylethylsulfinyl)methyl, 2-methylsulfinylethyl, 2-ethylsulfinylethyl, 2-(n-propylsulfinyl)ethyl, 2-(1-methylethylsulfinyl)-ethyl, 2-(n-butylsulfinyl)ethyl, 2-(1-methylpropylsulfinyl)ethyl, 2-(2-methylpropylsulfinyl)-ethyl, 2-(1,1-dimethylethylsulfinyl)ethyl, 2-($SOCH_3$)propyl, 3-($SOCH_3$)propyl, 2-($SOC_2H_5$)-propyl, 3-($SOC_2H_5$)propyl, 3-(propylsulfinyl)propyl, 3-(butylsulfinyl)propyl, 4-($SOCH_3$)butyl, 4-($SOC_2H_5$)butyl, 4-(n-propylsulfinyl)butyl or 4-(n-butylsulfinyl)butyl, in particular 2-($SOCH_3$)ethyl;

$C_1$–$C_4$-haloalkylsulfinyl-$C_1$–$C_4$-alkyl: $C_1$–$C_4$-alkyl which is substituted by $C_1$–$C_4$-haloalkylsulfinyl as mentioned above, ie. for example 2-(2,2,2-trifluoroethylsulfinyl)ethyl;

$C_1$–$C_4$-alkylsulfonyl: $SO_2$—$CH_3$, $SO_2$—$C_2H_5$, $SO_2$—$CH_2$—$C_2H_5$, $SO_2$—$CH(CH_3)_2$, n-butylsulfonyl, $SO_2$—CH($CH_3$)—$C_2H_5$, $SO_2$—$CH_2$—$CH(CH_3)_2$ or $SO_2$—$C(CH_3)_3$, preferably $SO_2$—$CH_3$ or $SO_2$—$C_2H_5$; $C_1$–$C_4$-haloalkylsulfonyl: a $C_1$–$C_4$-alkylsulfonyl radical as mentioned above which is partially or fully substituted by fluorine, chlorine, bromine and/or iodine, ie. for example $SO_2$—$CH_2F$, $SO_2$—$CHF_2$, $SO_2$—$CF_3$, $SO_2$—$CH_2Cl$, $SO_2$—$CH(Cl)_2$, $SO_2$—$C(Cl)_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, $SO_2$—$C_2F_5$, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, $SO_2$—$CH_2$—$C_2F_5$, $SO_2$—$CF_2$—$C_2F_5$, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl or nonafluorobutylsulfonyl, preferably $SO_2$—$CH_2Cl$, $SO_2$—$CF_3$ or 2,2,2-trifluoroethylsulfonyl;

$C_1$–$C_4$-alkylsulfonyl-$C_1$–$C_4$-alkyl: $C_1$–$C_4$-alkyl which is substituted by $C_1$–$C_4$-alkylsulfonyl as mentioned above, ie. for example $CH_2SO_2$—$CH_3$, $CH_2SO_2$—$C_2H_5$, $CH_2SO_2$—$CH_2$—$C_2H_5$, $CH_2SO_2$—$CH(CH_3)_2$, $CH_2SO_2$—$CH_2CH_2$—$C_2H_5$, (1-methylpropylsulfonyl)methyl, (2-methylpropylsulfonyl)methyl, $CH_2SO_2$—$C(CH_3)3$, $CH(CH_3)SO_2$—$CH_3$, $CH(CH_3)SO_2$—$C_2H_5$, $CH_2CH_2SO_2$—$CH_3$, $CH_2CH_2SO_2$—$C_2H_5$, $CH_2CH_2SO_2$—$CH_2$—$C_2H_5$, $CH_2CH_2SO_2$—$CH(CH_3)_2$, $CH_2CH_2SO_2$—$CH_2CH_2$—$C_2H_5$, 2-(1-methylpropylsulfonyl)ethyl, 2-(2-methylpropylsulfonyl)ethyl, $CH_2CH_2SO_2$—$C(CH_3)_3$, 2-($SO_2$—$CH_3$)propyl, 2-($SO_2C_2H_5$)propyl, 2-($SO_2$—$CH_2$—$C_2H_5$)propyl, 2-[($SO_2$—$CH(CH_3)_2$ ]propyl, 2-($SO_2$—$CH_2CH_2$—$C_2H_5$)propyl, 2-(1-methylpropylsulfonyl)propyl, 2-(2-methylpropylsulfonyl)propyl, 2-[$SO_2$—$C(CH_3)_3$]propyl, 3-($SO_2$—$CH_3$)propyl, 3-($SO_2$—$C_2H_5$)propyl, 3-($SO_2$—$CH_2$—$C_2H_5$)propyl, 3-[$SO_2$—$CH(CH_3)_2$]propyl, 3-($SO_2$—$CH_2CH_2$—$C_2H_5$) propyl, 3-(1-methylpropylsulfonyl)propyl, 3-(2-methylpropylsulfonyl)propyl, 3-[$SO_2$—$C(CH_3)_3$]propyl, 2-($SO_2$—$CH_3$)butyl, 2-($SO_2$—$C_2H_5$)butyl, 2-($SO_2$—$CH_2$—$C_2H_5$)butyl, 2-[$SO_2$—$CH(CH_3)_2$]butyl, 2-($SO_2$—$CH_2CH_2$—$C_2H_5$)butyl, 2-(1-methylpropylsulfonyl)butyl, 2-(2-methylpropylsulfonyl)butyl, 2-[$SO_2$—$C(CH_3)_3$]butyl, 3-($SO_2$—$CH_3$)butyl, 3-($SO_2$—$C_2H_5$)butyl, 3-($SO_2$—$CH_2$—$C_2H_5$)butyl, 3-[$SO_2$—$CH(CH_3)_2$]butyl, 3-($SO_2$—$CH_2CH_2$—$C_2H_5$)butyl, 3-(1-methylpropylsulfonyl)butyl, 3-(2-methylpropylsulfonyl)butyl, 3-[$SO_2$—$C(CH_3)_3$ ]butyl, 4-($SO_2$—$CH_3$)butyl, 4-($SO_2$—$C_2H_5$)butyl, 4-($SO_2$—$CH_2$—$C_2H_5$)butyl, 4-[$SO_2$—$CH(CH_3)_2$]butyl, 4-($SO_2$—$CH_2CH_2$—$C_2H_5$)butyl, 4-(1-methylpropylsulfonyl)butyl, 4-(2-methylpropylsulfonyl)butyl or 4-[$SO_2$—$C(CH_3)_3$] butyl, in particular $CH_2CH_2SO_2$—$CH_3$ or $CH_2CH_2SO_2$—$C_2H_5$;

$C_1$–$C_4$-haloalkylsulfonyl-$C_1$–$C_4$-alkyl: $C_1$–$C_4$-alkyl which is substituted by $C_1$–$C_4$-haloalkylsulfonyl as mentioned above, ie. for example 2-(2,2,2-trifluoroethylsulfonyl)ethyl;

$C_1$–$C_4$-alkylamino-$C_1$–$C_4$-alkyl: $C_1$–$C_4$-alkyl which is substituted by $C_1$–$C_4$-alkylamino such as $H_3C$—NH—, $H_5C_2$—NH—, n-propyl-NH—, 1-methylethyl-NH—, n-butyl-NH—, 1-methylpropyl-NH—, 2-methylpropyl-NH— and 1,1-dimethylethyl-NH—, preferably $H_3C$-NH— or $H_3C_2$—NH— [sic], ie. for example $CH_2CH_2$—NH—$CH_3$, $CH_2CH_2$—N($CH_3$)$_2$, $CH_2CH_2$-NH—$C_2H_5$ or $CH_2CH_2$—N($C_2H_5$)$_2$;

$C_1$–$C_4$-alkylaminocarbonyl: CO—NH—$CH_3$, CO—NH—$C_2H_5$, n-propylamino, CO—NH—CH($CH_3$)$_2$, CO—NH—$CH_2CH_2$—$C_2H_5$, CO—NH—CH($CH_3$)—$C_2H_5$, CO—NH—$CH_2$—$CH(CH_3)_2$ or CO—NH—$C(CH_3)_3$, preferably CO—NH—$CH_3$ or CO—NH—$C_2H_5$;

$C_1$–$C_4$-alkylaminocarbonyl-$C_1$–$C_4$-alkyl: $C_1$–$C_4$-alkyl which is substituted by $C_1$–$C_4$-alkylaminocarbonyl as mentioned above, preferably by CO—NH—$CH_3$ or CO—NH—$C_2H_5$, as [sic] for example $CH_2$—CO—NH—$CH_3$, $CH_2$—CO—NH—$C_2H_5$, $CH_2$—CO—NH—$CH_2$—$C_2H_5$, $CH_2$—CO—NH—$CH(CH_3)_2$, $CH_2$—CO—NH—$CH_2CH_2$—$C_2H_5$, $CH_2$—CO—NH—CH($CH_3$)—$C_2H_5$, $CH_2$—CO—NH—$CH_2$—$CH(CH_3)_2$, $CH_2$—CO—NH—$C(CH_3)_3$, $CH(CH_3)$—CO—NH—$CH_3$, $CH(CH_3)$—CO—NH—$C_2H_5$, 2-(CO—NH—$CH_3$)ethyl, 2-(CO—NH—$C_2H_5$)ethyl, 2-(CO—NH—$CH_2$—$C_2H_5$)-ethyl, 2-[$CH_2$—CO—NH—$CH(CH_3)_2$]ethyl, 2-(CO—NH—$CH_2CH_2$—$C_2H_5$)ethyl, 2-[CO—NH—CH($CH_3$)—$C_2H_5$]ethyl, 2-[CO—NH—$CH_2$—$CH(CH_3)_2$]ethyl, 2-[CO—NH—$C(CH_3)_3$]ethyl, 2-(CO—NH—$CH_3$)propyl, 2-(CO—NH—$C_2H_5$)propyl, 2-(CO—NH—$CH_2$—$C_2H_5$)propyl, 2-[$CH_2$—CO—NH—$CH(CH_3)_2$]propyl, 2-(CO—NH—$CH_2CH_2$—$C_2H_5$)propyl, 2-[CO—NH—CH($CH_3$)—$C_2H_5$]propyl, 2-[CO—NH—$CH_2$—$CH(CH_3)_2$]propyl, 2-[CO—NH—$C(CH_3)_3$]propyl, 3-(CO—NH—$CH_3$)propyl, 3-(CO—NH—$C_2H_5$)propyl, 3-(CO—NH—$CH_2$—$C_2H_5$)propyl, 3-[$CH_2$—CO—NH—$CH(CH_3)_2$]propyl, 3-(CO—NH—$CH_2CH_2$—$C_2H_5$)propyl, 3-[CO—NH—CH($CH_3$)—$C_2H_5$]propyl, 3-[CO—NH—$CH_2$—$CH(CH_3)_2$]propyl, 3-[CO—NH—$C(CH_3)_3$]propyl, 2-(CO—NH—$CH_3$)butyl, 2-(CO—NH—$C_2H_5$)-butyl, 2-(CO—NH—$CH_2$—$C_2H_5$)butyl, 2-[$CH_2$—CO—NH—CH($CH_3$)$_2$]butyl, 2-(CO—NH—$CH_2CH_2$—$CH_5$)butyl, 2-[CO—NH—CH($CH_3$)—$C_2H_5$]butyl, 2-[$C_1$(CO—NH—$CH_2$—CH($CH_3$)$_2$]butyl, 2-[CO—NH—C($CH_3$)$_3$]butyl, 3-(CO—NH—$CH_3$)butyl, 3-(CO—NH—$C_2H_5$)butyl, 3-(CO—NH—$CH_2$—$C_2H_5$)-butyl, 3-[$CH_2$—CO—NH—CH($CH_3$)$_2$]butyl, 3-(CO—NH—$CH_2CH_2$—$C_2H_5$)butyl, 3-[CO—NH—CH($CH_3$)—$C_2H_5$]butyl, 3-[CO—NH—$CH_2$—CH($CH_3$)$_2$]butyl, 3-[CO—NH—C($CH_3$)$_3$]butyl, 4-(CO—NH—$CH_3$)butyl, 4-(CO—NH—$C_2H_5$)butyl, 4-(CO—NH—$CH_2$—$C_2H_5$)butyl, 4-[$CH_2$—CO—NH—CH($CH_3$)$_2$ ]butyl, 4-(CO—NH—$CH_2CH_2$—$C_2H_5$)butyl, 4-[CO-N$C_1$R—CH($CH_3$)—$C_2H_5$]butyl, 4-[CO—NH—$CH_2$—CH($CH_3$)$_2$]butyl or 4—$C_1$[CO—NH—C($CH_3$)$_3$] butyl, preferably $CH_2$—CO—NH—$CH_3$, $CH_2$—CO—NH—$C_2H_5$, CH($CH_3$)—CO—NH—$CH_3$ or CH($CH_3$)—CO—NH—$C_2H_5$;

di($C_1$–$C_4$-alkyl)amino: N($CH_3$)$_2$, N($C_2H_5$)$_2$, N,N-dipropylamino, N,N-di(1-methylethyl)amino, N,N-dibutylamino, N,N-di(1-methylpropyl)amino, N,N-di(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-($C_1$-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)-amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino, preferably N($CH_3$)$_2$ or N($C_2H_5$)$_2$;

di($C_1$–$C_4$-alkyl)amino-$C_1$–$C_4$-alkyl: $C_1$–$C_4$-alkyl which is substituted by di($C_1$–$C_4$-alkyl)amino as mentioned above, ie. for example $CH_2$N($CH_3$)$_2$, $CH_2$N($C_2H_5$)$_2$, N,N-dipropylaminomethyl, N,N-di[CH($CH_3$)$_2$]aminomethyl, N,N-dibutylaminomethyl, N,N-di(1-methylpropyl) aminomethyl, N,N-di(2-methylpropyl)-aminomethyl, N,N-di[C($CH_3$)$_3$ ]aminomethyl, N-ethyl-N-methylaminomethyl, N-methyl-N-propylaminomethyl, N-methyl-N-[CH($CH_3$)$_2$] aminomethyl, N-butyl-N-methylaminomethyl, N-methyl-N-(1-methylpropyl)aminomethyl, N-methyl-N-(2-methylpropyl)aminomethyl, N-[C($CH_3$)$_3$]-N-methylaminomethyl, N-ethyl-N-propylaminomethyl, N-ethyl-N-[(CH($CH_3$)$_2$]aminomethyl, N-butyl-N-ethylaminomethyl, N-ethyl-N-(1-methylpropyl)-aminomethyl, N-ethyl-N-(2-methylpropyl)aminomethyl, N-ethyl-N-[C($CH_3$)$_3$]aminomethyl, N-[CH($CH_3$)$_2$]-N-propylaminomethyl, N-butyl-N-propylaminomethyl, N-(1-methylpropyl)-N-propylaminomethyl, N-(2-methylpropyl)-N-propylaminomethyl, N-[C($CH_3$)$_3$]-N-propylaminomethyl, N-butyl-N-(1-methylethyl) aminomethyl, N-[CH($CH_3$)$_2$]-N-(1-methylpropyl) aminomethyl, N—$C_1$[CH($CH_3$)$_2$]-N-(2-methylpropyl) aminomethyl, N-[C($CH_3$)$_3$]-N-[CH($CH_3$)$_2$]aminomethyl, N-butyl-N-(1-methylpropyl)aminomethyl, N-butyl-N-(2-methylpropyl)aminomethyl, N-butyl-N-[C($CH_3$)$_3$] aminomethyl, N-(1-methylpropyl)-N-(2-methylpropyl) aminomethyl, N-[C($CH_3$)$_3$]-N-(1-methylpropyl) aminomethyl, N-[C($CH_3$)$_3$]-N-(2-methylpropyl) aminomethyl, N,N-dimethylaminoethyl, N,N-diethylaminoethyl, N,N-di(n-propyl)aminoethyl, N,N-di [CH($CH_3$)$_2$ ]aminoethyl, N,N-dibutylaminoethyl, N,N-di(1-methylpropyl)aminoethyl, N,N-di(2-methylpropyl) aminoethyl, N, N-di-[C ($CH_3$)$_3$]aminoethyl, N-ethyl-N-methylaminoethyl, N-methyl-N-propylaminoethyl, N-methyl-N-[CH($CH_3$)$_2$ ]aminoethyl, N-butyl-N-methylaminoethyl, N-methyl-N-(1-methylpropyl) aminoethyl, N-methyl-N-(2-methylpropyl)aminoethyl, N-[C($CH_3$)$_3$]-N-methylaminoethyl, N-ethyl-N-propylaminoethyl, N-ethyl-N-[CH($CH_3$)$_2$]aminoethyl, N-butyl-N-ethylaminoethyl, N-ethyl-N-($C_1$-methylpropyl) aminoethyl, N-ethyl-N-(2-methylpropyl)aminoethyl, N-ethyl-N-[C($CH_3$)$_3$]aminoethyl, N—$C_1$[CH($CH_3$)$_2$]-N-propylaminoethyl, N-butyl-N-propylaminoethyl, N-(1-methylpropyl)-N-propylaminoethyl, N-(2-methylpropyl)-N-propylaminoethyl, N-[C($CH_3$)$_3$]-N-propylaminoethyl, N-butyl-N-[CH($CH_3$)$_2$]aminoethyl, N-[CH($CH_3$)$_2$ ]-N-(1-methylpropyl)aminoethyl, N-[CH($CH_3$)$_2$]-N-(2-methylpropyl)aminoethyl, N-[C($CH_3$)$_3$]-N-[CH($CH_3$)$_2$] aminoethyl, N-butyl-N-(1-methylpropyl)aminoethyl, N-butyl-N-(2-methylpropyl)aminoethyl, N-butyl-N-[C ($CH_3$)$_3$ ]aminoethyl, N-(1-methylpropyl)-N-(2-methylpropyl)-aminoethyl, N-[C($CH_3$)$_3$]-N-(1-methylpropyl)aminoethyl or N-[C($CH_3$)$_3$]-N-(2-methylpropyl)aminoethyl, in particular N,N-dimethylaminoethyl or N,N-diethylaminoethyl;

di($C_1$–$C_4$-alkyl)aminocarbonyl: CO—N($CH_3$)$_2$, CO—N($C_2H_5$) [sic], CO—N($CH_2$—$C_2H_5$)$_2$, CO—N[CH($CH_3$)$_2$]$_2$, N,N-dibutylaminocarbonyl, CO—N-[CH($CH_3$)—$C_2H_5$]$_2$, CO—N[$CH_2$—CH($CH_3$)$_2$]$_2$, CO—N[(C($CH_3$)$_3$]$_2$, N-ethyl-N-methylaminocarbonyl, N-methyl-N-propylaminocarbonyl, N-methyl-N-[C(CH($CH_3$)$_2$ ]aminocarbonyl, N-butyl-N-methylaminocarbonyl, N-methyl-N-(1-methylpropyl)aminocarbonyl, N-methyl-N-(2-methylpropyl)aminocarbonyl, N-[C($CH_3$)$_3$]-N-methylaminocarbonyl, N-ethyl-N-propylaminocarbonyl, N-ethyl-N-[CH($C_1H_3$)$_2$ ]aminocarbonyl, N-butyl-N-ethylaminocarbonyl, N-ethyl-N-(1-methylpropyl) aminocarbonyl, N-ethyl-N-(2-methylpropyl) aminocarbonyl, N-ethyl-N-aminocarbonyl, N-[CH($CH_3$)$_2$-N-propylaminocarbonyl, N-butyl-N-propylaminocarbonyl, N-(1-methylpropyl)-N-propylaminocarbonyl, N-(2-methylpropyl)-N-propylaminocarbonyl, N-[C($CH_3$)$_3$]-N-propylaminocarbonyl, N-butyl-N-[CH($CH_3$)$_2$ ]aminocarbonyl, N-[CH($CH_3$ )$_2$]-N-(1-methylpropyl) aminocarbonyl, N-[CH($CH_3$)$_2$]-N-(2-methylpropyl) aminocarbonyl, N-[C($CH_3$)$_3$]-N—$C_1$(CH($CH_3$)$_2$] aminocarbonyl, N-butyl-N-(1-methylpropyl) aminocarbonyl, N-butyl-N-(2-methylpropyl)-aminocarbonyl, N-butyl-N-[C($CH_3$)$_3$]aminocarbonyl, N-(1-methylpropyl)-N-(2-methylpropyl)aminocarbonyl, N-[C($CH_3$)$_3$]-N-(1-methylpropyl)aminocarbonyl or N-[C($CH_3$)$_3$]-N-(2-methylpropyl)aminocarbonyl, preferably CO—N($CH_3$)$_2$ or CO—N($C_2H_5$)$_2$;

di($C_1$–$C_4$-alkyl)aminocarbonyl-$C_1$–$C_4$-alkyl: $C_1$–$C_4$-alkyl which is substituted by di($C_1$–$C_4$-alkyl)aminocarbonyl as mentioned above, preferably by CO—N($CH_3$)$_2$ or CO—N($C_2H_5$), ie. for example $CH_2$—CO—N($CH_3$)$_2$, $CH_2$—CO—N($C_2H_5$)$_2$, CH($CH_3$)—CO—N($CH_3$)$_2$ or CH($CH_3$)—CO—N($C_2H_5$)$_2$, preferably $CH_2$—CO—N($CH_3$)$_2$ or CH($CH_3$)—CO—N($CH_3$)$_2$;

di($C_1$–$C_4$-alkyl)phosphonyl: —PO(O$CH_3$)$_2$, —PO(O$C_2H_5$)$_2$, N,N-dipropylphosphonyl, N,N-di(1-methylethyl)phosphonyl, N,N-dibutylphosphonyl, N,N-di(1-methylpropyl)phosphonyl, N,N-di(2-methylpropyl) phosphonyl, N,N-di(1,1-dimethylethyl)phosphonyl, N-ethyl-N-methylphosphonyl, N-methyl-N-propylphosphonyl, N-methyl-N-(1-methylethyl)phosphonyl, N-butyl-N-methylphosphonyl, N-methyl-N-(1-methylpropyl)-phosphonyl, N-methyl-N-(2-methylpropyl)phosphonyl, N-(1,1-dimethylethyl)-N-methylphosphonyl, N-ethyl-N-propylphosphonyl, N-ethyl-N-(1-methylethyl)phosphonyl, N-butyl-N-ethylphosphonyl, N-ethyl-N-(1-methylpropyl)phosphonyl, N-ethyl-N-(2-methylpropyl)phosphonyl, N-ethyl-N-(1,1-dimethylethyl)phosphonyl, N-(1-methylethyl)-N-propylphosphonyl, N-butyl-N-propylphosphonyl, N-(1-methylpropyl)-N-propylphosphonyl, N-(2-methylpropyl)-N-propylphosphonyl, N-(1,1-dimethylethyl)-N-propylphosphonyl, N-butyl-N-(1-methylethyl)phosphonyl, N-(1-methylethyl)-N-(1-methylpropyl)phosphonyl, N-(1-methylethyl)-N-(2-methylpropyl)phosphonyl, N-(1,1-dimethylethyl)-N-(1-methylethyl)phosphonyl, N-butyl-N-(1-methylpropyl)phosphonyl, N-butyl-N-(2-methylpropyl)phosphonyl, N-butyl-N-(1,1-dimethylethyl)phosphonyl, N-(1-methylpropyl)-N-(2-methylpropyl)phosphonyl, N-(1,1-dimethylethyl)-N-(1-methylpropyl)phosphonyl or N-(1,1-dimethylethyl)-N-(2-methylpropyl)phosphonyl, preferably —PO(OCH$_3$)$_2$ or —PO(OC$_2$H$_5$)$_2$;

di(C$_1$–C$_4$-alkyl)phosphonyl-C$_1$–C$_4$-alkyl: C$_1$–C$_4$-alkyl which is substituted by di(C$_1$–C$_4$-alkyl)phosphonyl as mentioned above, preferably by —PO(OCH$_3$)$_2$ or —PO(OC$_2$H$_5$)$_2$, i.e. for example CH$_2$—PO(OCH$_3$)$_2$, CH$_2$—PO(OC$_2$H$_5$)$_2$, CH(CH$_3$)—PO(OCH$_3$)$_2$ or CH(CH$_3$)—PO(OC$_2$H$_5$)$_2$;

C$_3$–C$_6$-alkenyl: prop-1-en-1-yl, allyl, 1-methylethenyl, 1-buten-1-yl, 1-buten-2-yl, 1-buten-3-yl, 2-buten-1-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

C$_3$–C$_6$-haloalkenyl: C$_3$–C$_6$-alkenyl as mentioned above which is partially or fully substituted by fluorine, chlorine, bromine and/or iodine. ie. for example 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl;

cyano-C$_3$—C$_6$-alkenyl: for example 2-cyanoallyl, 3-cyanoallyl, 4-cyanobut-2-enyl, 4-cyanobut-3-enyl or 5-cyanopent-4-enyl;

C$_3$–C$_6$-alkynyl: prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl, preferably prop-2-yn-1-yl;

C$_3$–C$_6$-haloalkynyl: C$_3$–C$_6$-alkynyl as mentioned above which is partially or fully substituted by fluorine, chlorine, bromine and/or iodine, ie. for example 1,1-difluoroprop-2-yn-1-yl, 4-fluorobut-2-yn-1-yl, 4-chlorobut-2-yn-1-yl, 1,1-difluorobut-2-yn-1-yl, 5-fluoropent-3-yn-1-yl or 6-fluorohex-4-yn-1-yl;

cyano-C$_3$–C$_6$-alkynyl: for example 3-cyanopropargyl, 4-cyanobut-2-yn-1-yl, 5-cyanopent-3-yn-1-yl and 6-cyanohex-4-yn-1-yl; C$_3$–C$_4$-alkenyloxy-C$_1$–C$_4$-alkyl: C$_1$–C$_4$-alkyl which is substituted by C$_3$–C$_4$-alkenyloxy such as allyloxy, but-1-en-3-yloxy, but-1-en-4-yloxy, but-2-en-1-yloxy, 1-methylprop-2-enyloxy or 2-methylprop-2-enyloxy, ie. for example allyloxymethyl, 2-allyloxyethyl or but-1-en-4-yloxymethyl, in particular 2-allyloxyethyl; po C$_3$–C$_4$-alkynyloxy-C$_1$–C$_4$-alkyl: C$_1$–C$_4$-alkyl which is substituted by C$_3$–C$_4$-alkynyloxy such as propargyloxy, but-1-yn-3-yloxy, but-1-yn-4-yloxy, but-2-yn-1-yloxy, 1-methylprop-2-ynyloxy or 2-methylprop-2-ynyloxy, preferably propargyloxy, ie. for example propargyloxymethyl or 2-propargyloxyethyl, in particular 2-propargyloxyethyl;

(C$_3$–C$_4$-alkenyloxy)imino-C$_1$–C$_4$-alkyl: C$_1$–C$_4$-alkyl which is substituted by (C$_3$–C$_4$-alkenyloxy)imino such as allyloxyimino, but-1-en-3-yloxyimino, but-1-en-4-yloxyimino, but-2-en-1-yloxyimino, 1-methylprop-2-enyloxyimino or 2-methylprop-2-enyloxyimino, ie. for example allyloxy-N=CH—CH$_2$ or but-1-en-4-yloxy-N=CH, in particular allyloxy-N=CH—CH$_2$; 2-alkenylthio-C$_1$–C$_4$-alkyl: C$_1$–C$_4$-alkyl which is substituted by C$_3$–C$_4$-alkenylthio such as allylthio, but-1-en-3-ylthio, but-1-en-4-ylthio, but-2-en-1-ylthio, 1-methylprop-2-enylthio or 2-methylprop-2-enylthio, ie. for example allylthiomethyl, 2-allylthioethyl or but-1-en-4-ylthiomethyl, in particular 2-allylthioethyl;

C$_3$–C$_4$-alkynylthio-C$_1$–C$_4$-alkyl: C$_1$–C$_4$-alkyl which is substituted by C$_3$–C$_4$-alkynylthio such as propargylthio, but-1-yn-3-ylthio, but-1-yn-4-ylthio, but-2-yn-1-ylthio, 1-methylprop-2-ynylthio or 2-methylprop-2-ynylthio, preferably propargylthio, ie. for example propargylthiomethyl or 2-propargylthioethyl, in particular 2-propargylthioethyl;

C$_3$–C$_4$-alkenylsulfinyl-C$_1$–C$_4$-alkyl: C$_1$–C$_4$-alkyl which is substituted by C$_3$–C$_4$-alkenylsulfinyl such as allylsulfinyl, but-1-en-3-ylsulfinyl, but-1-en-4-ylsulfinyl, but-2-en-1-ylsulfinyl, 1-methylprop-2-enylsulfinyl or 2-methylprop-2-enylsulfinyl, ie. for example allylsulfinylmethyl, 2-allylsulfinylethyl or but-1-en-4-ylsulfinylmethyl, in particular 2-allylsulfinylethyl;

C$_3$–C$_4$-alkynylsulfinyl-C$_1$–C$_4$-alkyl: C$_1$–C$_4$-alkyl which is substituted by C$_3$–C$_4$-alkynylsulfinyl such as propargylsulfinyl, but-1-yn-3-ylsulfinyl, but-1-yn-4-ylsulfinyl, but-2-yn-1-ylsulfinyl, 1-methylprop-2-ynylsulfinyl or 2-methylprop-2-ynylsulfinyl, preferably propargylsulfinyl, ie. for example propargylsulfinylmethyl or 2-propargylsulfinylethyl, in particular 2-propargylsulfinylethyl;

$C_3$–$C_4$-alkenylsulfonyl-$C_1$–$C_4$-alkyl: $C_1$–$C_4$-alkyl which is substituted by $C_3$–$C_4$-alkenylsulfonyl such as allylsulfonyl, but-1-en-3-ylsulfonyl, but-1-en-4-ylsulfonyl, but-2-en-1-ylsulfonyl, 1-methylprop-2-enylsulfonyl or 2-methylprop-2-enylsulfonyl, ie. for example allylsulfonylmethyl, 2-allylsulfonylethyl or but-1-en-4-ylsulfonylmethyl, in particular 2-allylsulfonylethyl;

$C_3$–$C_4$-alkynylsulfonyl-$C_1$–$C_4$-alkyl: $C_1$–$C_4$-alkyl which is substituted by $C_3$–$C_4$-alkynylsulfonyl such as propargylsulfonyl, but-1-yn-3-ylsulfonyl, but-1-yn-4-ylsulfonyl, but-2-yn-1-ylsulfonyl, 1-methylprop-2-ynylsulfonyl or 2-methylprop-2-ynylsulfonyl, preferably propargylsulfonyl, ie. for example propargylsulfonylmethyl or 2-propargylsulfonylethyl, in particular 2-propargylsulfonylethyl;

$C_3$–$C_8$-cycloalkyl: cyclopropyl, cyclobutyl, cyclopentyl, cyclohexyl, cycloheptyl or cyclooctyl;

$C_3$–$C_8$-cycloalkyl-$C_1$–$C_6$-alkyl: for example cyclopropylmethyl, cyclobutylmethyl, cyclopentylmethyl, cyclohexylmethyl, cycloheptylmethyl, cyclooctylmethyl, 2-(cyclopropyl)ethyl, 2-(cyclobutyl)ethyl, 2-(cyclopentyl)ethyl, 2-(cyclohexyl)ethyl, 2-(cycloheptyl)ethyl, 2-(cyclooctyl)ethyl, 3-(cyclopropyl)propyl, 3-(cyclobutyl)propyl, 3-(cyclopentyl)propyl, 3-(cyclohexyl)propyl, 3-(cycloheptyl)propyl, 3-(cyclooctyl)propyl, 4-(cyclopropyl)butyl, 4-(cyclobutyl)butyl, 4-(cyclopentyl)butyl, 4-(cyclohexyl)butyl, 4-(cycloheptyl)butyl, 4-(cyclooctyl)butyl, 5-(cyclopropyl)pentyl, 5-(cyclobutyl)pentyl, 5-(cyclopentyl)pentyl, 5-(cyclohexyl)pentyl, 5-(cycloheptyl)pentyl, 5-(cyclooctyl)pentyl, 6-(cyclopropyl)hexyl, 6-(cyclobutyl)hexyl, 6-(cyclopentyl)hexyl, 6-(cyclohexyl)hexyl, 6-(cycloheptyl)hexyl or 6-(cyclooctyl)hexyl;

$C_3$–$C_8$-cycloalkyl containing a carbonyl or thiocarbonyl ring member: for example cyclobutanon-2-yl, cyclobutanon-3-yl, cyclopentanon-2-yl, cyclopentanon-3-yl, cyclohexanon-2-yl, cyclohexanon-4-yl, cycloheptanon-2-yl, cyclooctanon-2-yl, cyclobutanethion-2-yl, cyclobutanethion-3-yl, cyclopentanethion-2-yl, cyclopentanethion-3-yl, cyclohexanethion-2-yl, cyclohexanethion-4-yl, cycloheptanethion-2-yl or cyclooctanethion-2-yl, preferably cyclopentanon-2-yl or cyclohexanon-2-yl;

$C_3$–$C_8$-cycloalkyl-$C_1$–$C_4$-alkyl containing a carbonyl or thiocarbonyl ring member: for example cyclobutanon-2-ylmethyl, cyclobutanon-3-ylmethyl, cyclopentanon-2-ylmethyl, cyclopentanon-3-ylmethyl, cyclohexanon-2-ylmethyl, cyclohexanon-4-ylmethyl, cycloheptanon-2-ylmethyl, cyclooctanon-2-ylmethyl, cyclobutanethion-2-ylmethyl, cyclobutanethion-3-ylmethyl, cyclopentanethion-2-ylmethyl, cyclopentanethion-3-ylmethyl, cyclohexanethion-2-ylmethyl, cyclohexanethion-4-ylmethyl, cycloheptanethion-2-ylmethyl, cyclooctanethion-2-ylmethyl, 1-(cyclobutanon-2-yl)ethyl, 1-(cyclobutanon-3-yl)ethyl, 1-(cyclopentanon-2-yl)-ethyl, 1-(cyclopentanon-3-yl)ethyl, 1-(cyclohexanon-2-yl)ethyl, 1-(cyclohexanon-4-yl)ethyl, 1-(cycloheptanon-2-yl)ethyl, 1-(cyclooctanon-2-yl)ethyl, 1-(cyclobutanethion-2-yl)ethyl, 1-(cyclobutanethion-3-yl)ethyl, 1-(cyclopentanethion-2-yl)ethyl, 1-(cyclopentanethion-3-yl)ethyl, 1-(cyclohexanethion-2-yl)ethyl, 1-(cyclohexanethion-4-yl) ethyl, 1-(cycloheptanethion-2-yl)ethyl, 1-(cyclooctanethion-2-yl)ethyl, 2-(cyclobutanon-2-yl)ethyl, 2-(cyclobutanon-3-yl)ethyl, 2-(cyclopentanon-2-yl)ethyl, 2-(cyclopentanon-3-yl)ethyl, 2-(cyclohexanon-2-yl)ethyl, 2-(cyclohexanon-4-yl)ethyl, 2-(cycloheptanon-2-yl)ethyl, 2-(cyclooctanon-2-yl)ethyl, 2-(cyclobutanethion-2-yl)ethyl, 2-(cyclobutanethion-3-yl)ethyl, 2-(cyclopentanethion-2-yl)-ethyl, 2-(cyclopentanethion-3-yl)ethyl, 2-(cyclohexanethion-2-yl) ethyl, 2-(cyclohexanethion-4-yl) ethyl, 2-(cycloheptanethion-2-yl)ethyl, 2-(cyclooctanethion-2-yl)ethyl, 3-(cyclobutanon-2-yl)propyl, 3-(cyclobutanon-3-yl)propyl, 3-(cyclopentanon-2-yl)propyl, 3-(cyclopentanon-3-yl)propyl, 3-(cyclohexanon-2-yl)propyl, 3-(cyclohexanon-4-yl)propyl, 3-(cycloheptanon-2-yl)propyl, 3-(cyclooctanon-2-yl)propyl, 3-(cyclobutanethion-2-yl)propyl, 3-(cyclobutanethion-3-yl)propyl, 3-(cyclopentanethion-2-yl)-propyl, 3-(cyclopentanethion-3-yl)propyl, 3-(cyclohexanethion-2-yl)propyl, 3-(cyclohexanethion-4-yl)propyl, 3-(cycloheptanethion-2-yl)propyl, 3-(cyclooctanethion-2-yl)propyl, 4-(cyclobutanon-2-yl)butyl, 4-(cyclobutanon-3-yl)butyl, 4-(cyclopentanon-2-yl)butyl, 4-(cyclopentanon-3-yl)butyl, 4-(cyclohexanon-2-yl)butyl, 4-(cyclohexanon-4-yl)butyl, 4-(cycloheptanon-2-yl)butyl, 4-(cyclooctanon-2-yl)butyl, 4-(cyclobutanethion-2-yl)butyl, 4-(cyclobutanethion-3-yl)butyl, 4-(cyclopentanethion-2-yl)-butyl, 4-(cyclopentanethion-3-yl)butyl, 4-(cyclohexanethion-2-yl)butyl, 4-(cyclohexanethion-4-yl)butyl, 4-(cycloheptanethion-2-yl)butyl or 4-(cyclooctanethion-2-yl)butyl;

$C_3$–$C_8$-cycloalkyloxy-$C_1$–$C_4$-alkyl: cyclopropyloxymethyl, 1-cyclopropyloxyethyl, 2-cyclopropyloxyethyl, 1-cyclopropyloxyprop-1-yl, 2-cyclopropyloxyprop-1-yl, 3-cyclopropyloxyprop-1-yl, 1-cyclopropyloxybut-1-yl, 2-cyclopropyloxybut-1-yl, 3-cyclopropyloxybut-1-yl, 4-cyclopropyloxybut-1-yl, 1-cyclopropyloxybut-2-yl, 2-cyclopropyloxybut-2-yl, 3-cyclopropyloxybut-2-yl, 3-cyclopropyloxybut-2-yl, 4-cyclopropyloxybut-2-yl, 1-(cyclopropyloxymethyl)eth-1-yl, 1-(cyclopropyloxymethyl)-1-($CH_3$)eth-1-yl, 1-(cyclopropylmethyloxy)-prop-1-yl, cyclobutyloxymethyl, 1-cyclobutyloxyethyl, 2-cyclobutyloxyethyl, 1-cyclobutyloxyprop-1-yl, 2-cyclobutyloxyprop-1-yl, 3-cyclobutyloxyprop-1-yl, 1-cyclobutyloxybut-1-yl, 2-cyclobutyloxybut-1-yl, 3-cyclobutyloxybut-1-yl, 4-cyclobutyloxybut-1-yl, 1-cyclobutyloxybut-2-yl, 2-cyclobutyloxybut-2-yl, 3-cyclobutyloxybut-2-yl, 3-cyclobutyloxybut-2-yl, 4-cyclobutyloxybut-2-yl, 1-(cyclobutyloxymethyl)eth-1-yl, 1-(cyclobutyloxymethyl)-1-($CH_3$)eth-1-yl, 1-(cyclobutyloxymethyl)prop-1-yl, cyclopentyloxymethyl, 1-cyclopentyloxyethyl, 2-cyclopentyloxyethyl, 1-cyclopentyloxyprop-1-yl, 2-cyclopentyloxyprop-1-yl, 3-cyclopentyloxyprop-1-yl, 1-cyclopentyloxybut-1-yl, 2-cyclopentyloxybut-1-yl, 3-cyclopentyloxybut-1-yl, 4-cyclopentyloxybut-1-yl, 1-cyclopentyloxybut-2-yl, 2-cyclopentyloxybut-2-yl, 3-cyclopentyloxybut-2-yl, 3-cyclopentyloxybut-2-yl, 4-cyclopentyloxybut-2-yl, 1-(cyclopentyloxymethyl)eth-1-yl, 1-(cyclopentyloxymethyl)-1-($CH_3$)eth-1-yl, 1-(cyclopentyloxymethyl)prop-1-yl, cyclohexyloxymethyl, 1-cyclohexyloxyethyl, 2-cyclohexyloxyethyl, 1-cyclohexyloxyprop-1-yl, 2-cyclohexyloxyprop-1-yl, 3-cyclohexyloxyprop-1-yl, 1-cyclohexyloxybut-1-yl, 2-cyclohexyloxybut-1-yl, 3-cyclohexyloxybut-1-yl, 4-cyclohexyloxybut-1-yl, 1-cyclohexyloxybut-2-yl, 2-cyclohexyloxybut-2-yl, 3-cyclohexyloxybut-2-yl, 3-cyclohexyloxybut-2-yl, 4-cyclohexyloxybut-2-yl, 1-(cyclohexyloxymethyl)eth-1-yl, 1-(cyclohexyloxymethyl)-1-($CH_3$)eth-1-yl, 1-(cyclohexyloxymethyl)prop-1-yl, cycloheptyloxymethyl, 1-cycloheptyloxyethyl, 2-cycloheptyloxyethyl, 1-cycloheptyloxyprop-1-yl, 2-cycloheptyloxyprop-1-yl, 3-cycloheptyloxyprop-1-yl, 1-cycloheptyloxybut-1-yl, 2-cycloheptyloxybut-1-yl, 3-cycloheptyloxybut-1-yl, 4-cycloheptyloxybut-1-yl, 1-cycloheptyloxybut-2-yl, 2-cycloheptyloxybut-2-yl, 3-cycloheptyloxybut-2-yl, 3-cycloheptyloxybut-2-yl, 4-cycloheptyloxybut-2-yl, 1-(cycloheptyloxymethyl)eth-1-yl, 1-(cycloheptyloxymethyl)-1-($CH_3$)eth-1-yl, 1-(cycloheptyloxymethyl)prop-1-yl, cyclooctyloxymethyl, 1-cyclooctyloxyethyl, 2-cyclooctyloxyethyl, 1-cyclooctyloxyprop-1-yl, 2-cyclooctyloxyprop-1-yl, 3-cyclooctyloxyprop-1-yl, 1-cyclooctyloxybut-1-yl, 2-cyclooctyloxybut-1-yl, 3-cyclooctyloxybut-1-yl, 4-cyclooctyloxybut-1-yl, 1-cyclooctyloxybut-2-yl, 2-cyclooctyloxybut-2-yl, 3-cyclooctyloxybut-2-yl, 3-cyclooctyloxybut-2-yl, 4-cyclooctyloxybut-2-yl, 1-(cyclooctyloxymethyl)eth-1-yl, 1-(cyclooctyloxymethyl)-1-($CH_3$)eth-1-yl or 1-(cyclooctyloxymethyl)prop-1-yl, in particular $C_3$–$C_6$-cycloalkoxymethyl or 2-($C_3$–$C_6$-cycloalkoxy)ethyl.

3- to 7-membered heterocyclyl is a saturated, partially or fully unsaturated or aromatic heterocycle having one to three hetero atoms selected from a group consisting of
  one to three nitrogens,
  one or two oxygens and
  one or two sulfur atoms.

Examples of saturated heterocycles which can contain a carbonyl or thiocarbonyl ring member are: oxiranyl, thiiranyl, aziridin-1-yl, aziridin-2-yl, diaziridin-1-yl, diaziridin-3-yl, oxetan-2-yl, oxetan-3-yl, thietan-2-yl, thietan-3-yl, azetidin-1-yl, azetidin-2-yl, azetidin-3-yl, tetrahydrofuran-2-yl, tetrahydrofuran-3-yl, tetrahydrothiophen-2-yl, tetrahydrothiophen-3-yl, pyrrolidin-1-yl, pyrrolidin-2-yl, pyrrolidin-3-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-oxazolidin-2-yl, 1,3-oxazolidin-3-yl, 1,3-oxazolidin-4-yl, 1,3-oxazolidin-5-yl, 1,2-oxazolidin-2-yl, 1,2-oxazolidin-3-yl, 1,2-oxazolidin-4-yl, 1,2-oxazolidin-5-yl, 1,3-dithiolan-2-yl, 1,3-dithiolan-4-yl, pyrrolidin-1-yl, pyrrolidin-2-yl, pyrrolidin-5-yl, tetrahydropyrazol-1-yl, tetrahydropyrazol-3-yl, tetrahydropyrazol-4-yl, tetrahydropyran-2-yl, tetrahydropyran-3-yl, tetrahydropyran-4-yl, tetrahydrothiopyran-2-yl, tetrahydrothiopyran-3-yl, tetrahydropyran-4-yl, piperidin-1-yl, piperidin-2-yl, piperidin-3-yl, piperidin-4-yl, 1,3-dioxan-2-yl, 1,3-dioxan-4-yl, 1,3-dioxan-5-yl, 1,4-dioxan-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, morpholin-2-yl, morpholin-3-yl, morpholin-4-yl, hexahydropyridazin-1-yl, hexahydropyridazin-3-yl, hexahydropyridazin-4-yl, hexahydropyrimidin-1-yl, hexahydropyrimidin-2-yl, hexahydropyrimidin-4-yl, hexahydropyrimidin-5-yl, piperazin-1-yl, piperazin-2-yl, piperazin-3-yl, hexahydro-1,3,5-triazin-1-yl, hexahydro-1,3,5-triazin-2-yl, oxepan-2-yl, oxepan-3-yl, oxepan-4-yl, thiepan-2-yl, thiepan-3-yl, thiepan-4-yl, 1,3-dioxepan-2-yl, 1,3-dioxepan-4-yl, 1,3-dioxepan-5-yl, 1,3-dioxepan-6-yl, 1,3-dithiepan-2-yl, 1,3-dithiepan-2-yl, 1,3-dithiepan-2-yl, 1,3-dithiepan-2-yl, 1,4-dioxepan-2-yl, 1,4-dioxepan-7-yl, hexahydroazepin-1-yl, hexahydroazepin-2-yl, hexahydroazepin-3-yl, hexahydroazepin-4-yl, hexahydro-1,3-diazepin-1-yl, hexahydro-1,3-diazepin-2-yl, hexahydro-1,3-diazepin-4-yl, hexahydro-1,4-diazepin-1-yl and hexahydro-1,4-diazepin-2-yl.

Examples of unsaturated heterocycles which can contain a carbonyl or thiocarbonyl ring member are: dihydrofuran-2-yl, 1,2-oxazolin-3-yl, 1,2-oxazolin-5-yl, 1,3-oxazolin-2-yl;

Preferred heteroaromatics are the 5- and 6-membered heteroaromatics, ie. for example: furyl, such as 2-furyl and 3-furyl, thienyl, such as 2-thienyl and 3-thienyl, pyrrolyl, such as 2-pyrrolyl and 3-pyrrolyl, isoxazolyl, such as 3-isoxazolyl, 4-isoxazolyl and 5-isoxazolyl, isothiazolyl such as 3-isothiazolyl, 4-isothiazolyl and 5-isothiazolyl, pyrazolyl, such as 3-pyrazolyl, 4-pyrazolyl and 5-pyrazolyl, oxazolyl, such as 2-oxazolyl, 4-oxazolyl and 5-oxazolyl, thiazolyl such as 2-thiazolyl, 4-thiazolyl and 5-thiazolyl, imidazolyl, such as 2-ir$C_1$midazolyl and 4-imidazolyl, oxadiazolyl, such as 1,2,4-oxadiazol-3-yl, 1,2,4-oxadiazol-5-yl and 1,3,4-oxadiazol-2-yl, thiadiazolyl, such as 1,2,4-thiadiazol-3-yl, 1,2,4-thiadiazol-5-yl and 1,3,4-thiadiazol-2-yl, triazolyl, such as 1,2,4-triazol-1-yl, 1,2,4-triazol-3-yl and 1,2,4-triazol-4-yl, pyridinyl, such as 2-pyridinyl, 3-pyridinyl and 4-pyridinyl, pyridazinyl, such as 3-pyridazinyl and 4-pyridazinyl, pyrimidinyl, such as 2-pyrimidinyl, 4-pyrimidinyl and 5-pyrimidinyl, and furthermore 2-pyrazinyl, 1,3,5-triazin-2-yl and 1,2,4-triazin-3-yl, in particular pyridyl, pyrimidyl, furanyl and thienyl.

All phenyl, carbocyclic and heterocyclic rings are preferably unsubstituted or carry one substituent.

Preferred with a view to the use of the substituted pyrazol-3-ylbenzazoles I as herbicides or desiccants/defoliants are those compounds I where the variables have the following meanings, in each case either on their own or in combination:

$R^1$ is $C_1$–$C_4$-alkyl, in particular methyl;

$R^2$ is $C_1$–$C_4$-haloalkyl, $C_1$–$C_4$-haloalkoxy or $C_1$–$C_4$-alkylsulfonyl, in particular trifluoromethyl, difluoromethoxy or methylsulfonyl, especially preferably difluoromethoxy;

$R^3$ is halogen, in particular chlorine;

$R^4$ is hydrogen, fluorine or chlorine, in particular fluorine or chlorine;

$R^5$ is cyano, halogen or trifluoromethyl, in particular halogen, especially preferably chlorine;

Z is a group —N═C($XR^6$)—O— or —N═C($XR^6$)—S— which is bonded to a via oxygen or sulfur, in particular —N═C($XR^6$)—S— which is bonded to a via the sulfur;

X is a chemical bond, oxygen, sulfur, —NH— or —N($R^7$)—;

$R^6$ and $R^7$ independently of one another are each $C_1$–$C_6$-alkyl, $C_1$–$C_6$-haloalkyl, cyano-$C_1$–$C_4$-alkyl, hydroxy-$C_1$–$C_4$-alkyl, $C_3$–$C_6$-alkenyl, $C_3$–$C_6$-alkynyl, $C_1$–$C_4$-alkoxy-$C_1$–$C_4$-alkyl, $C_1$–$C_4$-alkylthio-$C_1$–$C_4$-alkyl, $C_1$–$C_4$-alkylsulfonyl$C_1C_1C_1$–$C_4$-alkyl, ($C_1$–$C_4$-alkoxy)carbonyl-$C_1$–$C_4$-alkyl, di($C_1$–$C_4$-alkyl)aminocarbonyl-$C_1$–$C_4$-alkyl, $C_3$–$C_8$-cycloalkyl, $C_3$–$C_8$-cycloalkyl-$C_1$–$C_4$-alkyl, phenyl or phenyl-$C_1$–$C_4$-alkyl; if X is a chemical bond, oxygen, sulfur, —NH— or —N($R^7$)—, $R^6$ may furthermore be ($C_1$–$C_4$-alkyl)carbonyl or $C_1$–$C_4$-alkylsulfonyl; if X is a chemical bond, $R^6$ may furthermore be hydrogen, cyano, amino, halogen or —CH═CH—$R^8$;

$R^6$ and $R^7$ are each in particular $C_1$–$C_6$-alkyl, hydroxy-$C_1$–$C_4$-alkyl, $C_3$–$C_6$-alkenyl, $C_3$–$C_6$-alkynyl or ($C_1$–$C_4$-alkoxy)carbonyl-$C_1$–$C_4$-alkyl; if x is a chemical bond, $R^6$ may furthermore be in particular hydrogen or —CH═CH—$R^8$;

$R^8$ is ($C_1$–$C_4$-alkoxy)carbonyl.

Very particular preference is given to the substituted pyrazol-3-ylbenzazoles of formula Ia (= I where $R^1$=methyl, $R^2$=difluoromethoxy, $R^3$ and $R^5$=chlorine, $R^4$=hydrogen, Z=—N═C($XR^6$)—S— which is bonded to α via the sulfur), in particular to the compounds listed in Table 1 below:

TABLE 1

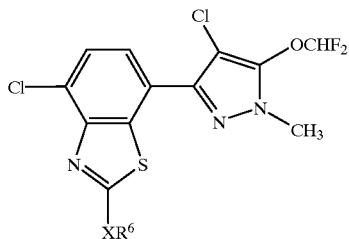

| No. | —XR⁶ |
|---|---|
| Ia.001 | —H |
| Ia.002 | —CH$_3$ |
| Ia.003 | —C$_2$H$_5$ |
| Ia.004 | —(n-C$_3$H$_7$) |
| Ia.005 | —CH(CH$_3$)$_2$ |
| Ia.006 | —(n-C$_4$H$_9$) |
| Ia.007 | —CH$_2$—CH(CH$_3$)$_2$ |
| Ia.008 | —CH(CH$_3$)—C$_2$H$_5$ |
| Ia.009 | —C(CH$_3$)$_3$ |
| Ia.010 | —CH$_2$—CH=CH$_2$ |
| Ia.011 | —CH$_2$—CH=CH—CH$_3$ |
| Ia.012 | —CH$_2$—CH$_2$—CH=CH$_2$ |
| Ia.013 | —CH$_2$—C≡CH |
| Ia.014 | —CH$_2$—OCH$_3$ |
| Ia.015 | —CH$_2$—CH$_2$—OCH$_3$ |
| Ia.016 | —CH$_2$—CN |
| Ia.017 | —CH$_2$—CH$_2$F |
| Ia.018 | —CH$_2$—CF$_3$ |
| Ia.019 | —CH$_2$—CH$_2$Cl |
| Ia.020 | —CH$_2$—CO—OCH$_3$ |
| Ia.021 | —CH$_2$—CO—OC$_2$H$_5$ |
| Ia.022 | —CH$_2$—CO—N(CH$_3$)$_2$ |
| Ia.023 | —CH$_2$—CH(=N—OCH$_3$) |
| Ia.024 | —CH$_2$—CH(=N—OC$_2$H$_5$) |
| Ia.025 | —CH$_2$—CH[=N—O(n-C$_3$H$_7$)] |
| Ia.026 | —CH$_2$—CH[=N—OCH(CH$_3$)$_2$] |
| Ia.027 | —CH$_2$—CH[=N—O(n-C$_4$H$_9$)] |
| Ia.028 | —CH$_2$—CH(=N—OCH$_2$—CH=CH$_2$) |
| Ia.029 | -cyclobutyl |
| Ia.030 | -cyclopentyl |
| Ia.031 | -cyclohexyl |
| Ia.032 | -phenyl |
| Ia.033 | —CH$_2$-cyclobutyl |
| Ia.034 | —CH$_2$-cyclopentyl |
| Ia.035 | —CH$_2$-cyclohexyl |
| Ia.036 | —CH$_2$-phenyl |
| Ia.037 | —NO$_2$ |
| Ia.038 | —CN |
| Ia.039 | —F |
| Ia.040 | —Cl |
| Ia.041 | —Br |
| Ia.042 | —OCH$_3$ |
| Ia.043 | —OC$_2$H$_5$ |
| Ia.044 | —O(n-C$_3$H$_7$) |
| Ia.045 | —OCH(CH$_3$)$_2$ |
| Ia.046 | —O(n-C$_4$H$_9$) |
| Ia.047 | —OCH$_2$—CH(CH$_3$)$_2$ |
| Ia.048 | —OCH(CH$_3$)—C$_2$H$_5$ |
| Ia.049 | —OC(CH$_3$)$_3$ |
| Ia.050 | —OCH$_2$—CH=CH$_2$ |
| Ia.051 | —OCH$_2$—CH=CH—CH$_3$ |
| Ia.052 | —OCH$_2$—CH$_2$—CH=CH$_2$ |
| Ia.053 | —OCH(CH$_3$)—CH=CH$_2$ |
| Ia.054 | —OCH$_2$—C≡CH |
| Ia.055 | —OCH(CH$_3$)—C≡CH |
| Ia.056 | —OCH$_2$—OCH$_3$ |
| Ia.057 | —OCH$_2$—CH$_2$—OCH$_3$ |
| Ia.058 | —OCH$_2$—CN |
| Ia.059 | —OCH$_2$—CH$_2$F |
| Ia.060 | —OCH$_2$—CF$_3$ |
| Ia.061 | —OCH$_2$—CO—OCH$_3$ |
| Ia.062 | —OCH$_2$—CO—OC$_2$H$_5$ |
| Ia.063 | —OCH$_2$—CO—N(CH$_3$)$_2$ |

TABLE 1-continued

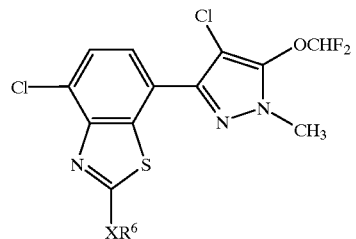

| No. | —XR⁶ |
|---|---|
| Ia.064 | —OCH$_2$—CH(=N—OCH$_3$) |
| Ia.065 | —OCH$_2$—CH(=N—OC$_2$H$_5$) |
| Ia.066 | —OCH$_2$—CH[=N—O(n-C$_3$H$_7$)] |
| Ia.067 | —OCH$_2$—CH[=N—OCH(CH$_3$)$_2$] |
| Ia.068 | —OCH$_2$—CH[=N—O(n-C$_4$H$_9$)] |
| Ia.069 | —OCH$_2$—CH(=N—OCH$_2$—CH=CH$_2$) |
| Ia.070 | —O-cyclobutyl |
| Ia.071 | —O-cyclopentyl |
| Ia.072 | —O-cyclohexyl |
| Ia.073 | —O-phenyl |
| Ia.074 | —OCH$_2$-cyclobutyl |
| Ia.075 | —OCH$_2$-cyclopentyl |
| Ia.076 | —OCH$_2$-cyclohexyl |
| Ia.077 | —OCH$_2$-phenyl |
| Ia.078 | —CH$_2$—OH |
| Ia.079 | —CH$_2$—OCH$_3$ |
| Ia.080 | —NH$_2$ |
| Ia.081 | —NH—CH$_3$ |
| Ia.082 | —N(CH$_3$)$_2$ |
| Ia.083 | —NH—C$_2$H$_5$ |
| Ia.084 | —N(C$_2$H$_5$)$_2$ |
| Ia.085 | —NH—(n-C$_3$H$_7$) |
| Ia.086 | —N(n-C$_3$H$_7$)$_2$ |
| Ia.087 | —NH—(n-C$_4$H$_9$) |
| Ia.088 | —N(n-C$_4$H$_9$)$_2$ |
| Ia.089 | —NH—CH(CH$_3$)$_2$ |
| Ia.090 | —N[CH(CH$_3$)$_2$]$_2$ |
| Ia.091 | —NH—CH$_2$—CH(CH$_3$)$_2$ |
| Ia.092 | —N[CH$_2$—CH(CH$_3$)$_2$]$_2$ |
| Ia.093 | —NH—CH$_2$—CH=CH$_2$ |
| Ia.094 | —N(CH$_2$—CH=CH$_2$)$_2$ |
| Ia.095 | —NH—CH$_2$—C≡CH |
| Ia.096 | —N(CH$_2$—C≡CH)$_2$ |
| Ia.097 | —CH$_2$—N(CH$_3$)$_2$ |
| Ia.098 | —SH |
| Ia.099 | —SCH$_3$ |
| Ia.100 | —SC$_2$H$_5$ |
| Ia.101 | —S(n-C$_3$H$_7$) |
| Ia.102 | —S(n-C$_4$H$_9$) |
| Ia.103 | —SCH(CH$_3$)$_2$ |
| Ia.104 | —SCH$_2$—CH(CH$_3$)$_2$ |
| Ia.105 | —SCH(CH$_3$)—C$_2$H$_5$ |
| Ia.106 | —SC(CH$_3$)$_3$ |
| Ia.107 | —SCH$_2$—CH=CH$_2$ |
| Ia.108 | —SCH$_2$—CH=CH—CH$_3$ |
| Ia.109 | —SCH$_2$—CH$_2$—CH=CH$_2$ |
| Ia.110 | —SCH(CH$_3$)—CH=CH$_2$ |
| Ia.111 | —SCH$_2$—C≡CH |
| Ia.112 | —SCH(CH$_3$)—C≡CH |
| Ia.113 | —SCH$_2$—OCH$_3$ |
| Ia.114 | —SCH$_2$—CH$_2$—OCH$_3$ |
| Ia.115 | —SCH$_2$—CN |
| Ia.116 | —SCH$_2$—CH$_2$F |
| Ia.117 | —SCH$_2$—CF$_3$ |
| Ia.118 | —SCH$_2$—CH$_2$Cl |
| Ia.119 | —SCH$_2$—CO—OCH$_3$ |
| Ia.120 | —SCH$_2$—CO—OC$_2$H$_5$ |
| Ia.121 | —SCH$_2$—CO—N(CH$_3$)$_2$ |
| Ia.122 | —SCH$_2$—CH(=N—OCH$_3$) |
| Ia.123 | —SCH$_2$—CH(=N—OC$_2$H$_5$) |
| Ia.124 | —SCH$_2$—CH[=N—O(n-C$_3$H$_7$)] |
| Ia.125 | —SCH$_2$—CH[=N—OCH(CH$_3$)$_2$] |
| Ia.126 | —SCH$_2$—CH[=N—O(n-C$_4$H$_9$)] |

TABLE 1-continued

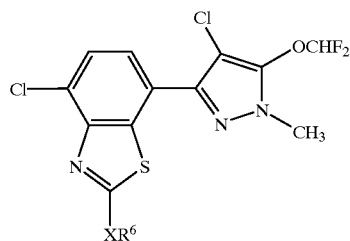

| No. | —XR⁶ |
|---|---|
| Ia.127 | —SCH₂—CH(=N—OCH₂—CH=CH₂) |
| Ia.128 | —S-cyclobutyl |
| Ia.129 | —S-cyclopentyl |
| Ia.130 | —S-cyclohexyl |
| Ia.131 | —S-phenyl |
| Ia.132 | —SCH₂-cyclobutyl |
| Ia.133 | —SCH₂-cyclopentyl |
| Ia.134 | —SCH₂-cyclohexyl |
| Ia.135 | —SCH₂-phenyl |
| Ia.136 | —CH₂—SCH₃ |
| Ia.137 | —SO—CH₃ |
| Ia.138 | —SO—C₂H₅ |
| Ia.139 | —SO—(n-C₃H₇) |
| Ia.140 | —SO—(n-C₄H₉) |
| Ia.141 | —SO—CH(CH₃)₂ |
| Ia.142 | —SO—CH₂—CH(CH₃)₂ |
| Ia.143 | —SO—CH(CH₃)—C₂H₅ |
| Ia.144 | —SO—C(CH₃)₃ |
| Ia.145 | —SO—CH₂—CH=CH₂ |
| Ia.146 | —SO—CH₂—CH=CH—CH₃ |
| Ia.147 | —SO—CH₂—CH₂—CH=CH₂ |
| Ia.148 | —SO—CH(CH₃)—CH=CH₂ |
| Ia.149 | —SO—CH₂—C≡CH |
| Ia.150 | —SO—CH(CH₃)—C≡CH |
| Ia.151 | —SO—CH₂—OCH₃ |
| Ia.152 | —SO—CH₂—CH₂—OCH₃ |
| Ia.153 | —SO—CH₂—CN |
| Ia.154 | —SO—CH₂—CH₂F |
| Ia.155 | —SO—CH₂—CF₃ |
| Ia.156 | —SO—CH₂—CH₂Cl |
| Ia.157 | —SO—CH₂—CO—OCH₃ |
| Ia.158 | —SO—CH₂—CO—OC₂H₅ |
| Ia.159 | —SO—CH₂—CO—N(CH₃)₂ |
| Ia.160 | —SO—CH₂—CH(=N—OCH₃) |
| Ia.161 | —SO—CH₂—CH(=N—OC₂H₅) |
| Ia.162 | —SO—CH₂—CH[=N—O(n-C₃H₇)] |
| Ia.163 | —SO—CH₂—CH[=N—OCH(CH₃)₂] |
| Ia.164 | —SO—CH₂—CH[=N—O(n-C₄H₉)] |
| Ia.165 | —SO—CH₂—CH(=N—OCH₂—CH=CH₂) |
| Ia.166 | —SO-cyclobutyl |
| Ia.167 | —SO-cyclopentyl |
| Ia.168 | —SO-cyclohexyl |
| Ia.169 | —SO-phenyl |
| Ia.170 | —SO—CH₂-cyclobutyl |
| Ia.171 | —SO—CH₂-cyclopentyl |
| Ia.172 | —SO—CH₂-cyclohexyl |
| Ia.173 | —SO—CH₂-phenyl |
| Ia.174 | —CH₂—SO—CH₃ |
| Ia.175 | —SO₂—CH₃ |
| Ia.176 | —SO₂—C₂H₅ |
| Ia.177 | —SO₂—(n-C₃H₇) |
| Ia.178 | —SO₂—(n-C₄H₉) |
| Ia.179 | —SO₂—CH(CH₃)₂ |
| Ia.180 | —SO₂—CH₂—CH(CH₃)₂ |
| Ia.181 | —SO₂—CH(CH₃)—C₂H₅ |
| Ia.182 | —SO₂—C(CH₃)₃ |
| Ia.183 | —SO₂—CH₂—CH=CH₂ |
| Ia.184 | —SO₂—CH₂—CH=CH—CH₃ |
| Ia.185 | —SO₂—CH₂—CH₂—CH=CH₂ |
| Ia.186 | —SO₂—CH(CH₃)—CH=CH₂ |
| Ia.187 | —SO₂—CH₂—C≡CH |
| Ia.188 | —SO₂—CH(CH₃)—C≡CH |
| Ia.189 | —SO₂—CH₂—OCH₃ |

TABLE 1-continued

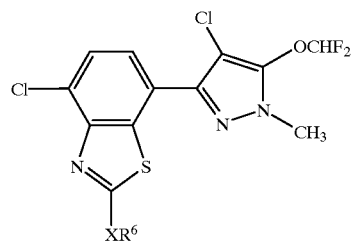

| No. | —XR⁶ |
|---|---|
| Ia.190 | —SO₂—CH₂—CH₂—OCH₃ |
| Ia.191 | —SO₂—CH₂—CN |
| Ia.192 | —SO₂—CH₂—CH₂F |
| Ia.193 | —SO₂—CH₂—CF₃ |
| Ia.194 | —SO₂—CH₂—CH₂Cl |
| Ia.195 | —SO₂—CH₂—CO—OCH₃ |
| Ia.196 | —SO₂—CH₂—CO—OC₂H₅ |
| Ia.197 | —SO₂—CH₂—CO—N(CH₃)₂ |
| Ia.198 | —SO₂—CH₂—CH(=N—OCH₃) |
| Ia.199 | —SO₂—CH₂—CH(=N—OC₂H₅) |
| Ia.200 | —SO₂—CH₂—CH[=N—O(n-C₃H₇)] |
| Ia.201 | —SO₂—CH₂—CH[=N—OCH(CH₃)₂] |
| Ia.202 | —SO₂—CH₂—CH[=N—O(n-C₄H₉)] |
| Ia.203 | —SO₂—CH₂—CH(=N—OCH₂—CH=CH₂) |
| Ia.204 | —SO₂-cyclobutyl |
| Ia.205 | —SO₂-cyclopentyl |
| Ia.206 | —SO₂-cyclohexyl |
| Ia.207 | —SO₂-phenyl |
| Ia.208 | —SO₂—CH₂-cyclobutyl |
| Ia.209 | —SO₂—CH₂-cyclopentyl |
| Ia.210 | —SO₂—CH₂-cyclohexyl |
| Ia.211 | —SO₂—CH₂-phenyl |
| Ia.212 | —CH₂—SO₂—CH₃ |
| Ia.213 | —CH₂—CH(Cl)—CO—OH |
| Ia.214 | —CH₂—CH(Cl)—CO—OCH₃ |
| Ia.215 | —CH₂—CH(Cl)—CO—OC₂H₅ |
| Ia.216 | —CH₂—CH(Cl)—CO—O(n-C₃H₇) |
| Ia.217 | —CH₂—CH(Cl)—CO—O(n-C₄H₉) |
| Ia.218 | —CH₂—CH(Cl)—CO—OCH(CH₃)₂ |
| Ia.219 | —CH₂—CH(Cl)—CO—OCH₂—CH(CH₃)₂ |
| Ia.220 | —CH₂—CH(Cl)—CO—OCH(CH₃)—C₂H₅ |
| Ia.221 | —CH₂—CH(Cl)—CO—OC(CH₃)₃ |
| Ia.222 | —CH₂—CH(Br)—CO—OH |
| Ia.223 | —CH₂—CH(Br)—CO—OCH₃ |
| Ia.224 | —CH₂—CH(Br)—CO—OC₂H₅ |
| Ia.225 | —CH₂—CH(Br)—CO—O(n-C₃H₇) |
| Ia.226 | —CH₂—CH(Br)—CO—O(n-C₄H₉) |
| Ia.227 | —CH₂—CH(Br)—CO—OCH(CH₃)₂ |
| Ia.228 | —CH₂—CH(Br)—CO—OCH₂—CH(CH₃)₂ |
| Ia.229 | —CH₂—CH(Br)—CO—OCH(CH₃)—C₂H₅ |
| Ia.230 | —CH₂—CH(Br)—CO—OC(CH₃)₃ |
| Ia.231 | —CH=CH—CO—OH |
| Ia.232 | —CH=CH—CO—OCH₃ |
| Ia.233 | —CH=CH—CO—OC₂H₅ |
| Ia.234 | —CH=CH—CO—O(n-C₃H₇) |
| Ia.235 | —CH=CH—CO—O(n-C₄H₉) |
| Ia.236 | —CH=CH—CO—OCH(CH₃)₂ |
| Ia.237 | —CH=CH—CO—OCH₂—CH(CH₃)₂ |
| Ia.238 | —CH=CH—CO—OCH(CH₃)—C₂H₅ |
| Ia.239 | —CH=CH—CO—OC(CH₃)₃ |
| Ia.240 | —CH=C(Cl)—CO—OH |
| Ia.241 | —CH=C(Cl)—CO—OCH₃ |
| Ia.242 | —CH=C(Cl)—CO—OC₂H₅ |
| Ia.243 | —CH=C(Cl)—CO—O(n-C₃H₇) |
| Ia.244 | —CH=C(Cl)—CO—O(n-C₄H₉) |
| Ia.245 | —CH=C(Cl)—CO—OCH(CH₃)₂ |
| Ia.246 | —CH=C(Cl)—CO—OCH₂—CH(CH₃)₂ |
| Ia.247 | —CH=C(Cl)—CO—OCH(CH₃)—C₂H₅ |
| Ia.248 | —CH=C(Cl)—CO—OC(CH₃)₃ |
| Ia.249 | —CH=C(Br)—CO—OH |
| Ia.250 | —CH=C(Br)—CO—OCH₃ |
| Ia.251 | —CH=C(Br)—CO—OC₂H₅ |
| Ia.252 | —CH=C(Br)—CO—O(n-C₃H₇) |

TABLE 1-continued

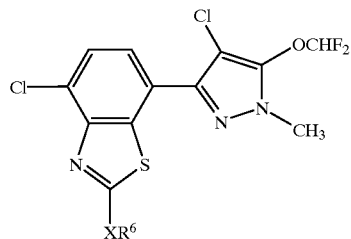

Ia

| No. | —XR⁶ |
|---|---|
| Ia.253 | —CH=C(Br)—CO—O(n-C₄H₉) |
| Ia.254 | —CH=C(Br)—CO—OCH(CH₃)₂ |
| Ia.255 | —CH=C(Br)—CO—OCH₂—CH(CH₃)₂ |
| Ia.256 | —CH=C(Br)—CO—OCH(CH₃)—C₂H₅ |
| Ia.257 | —CH=C(Br)—CO—OC(CH₃)₃ |
| Ia.258 | —CH₂—CH(Cl)—CO—NH₂ |
| Ia.259 | —CH₂—CH(Cl)—CO—NH—CH₃ |
| Ia.260 | —CH₂—CH(Cl)—CO—N(CH₃)₂ |
| Ia.261 | —CH₂—CH(Cl)—CO—NH—C₂H₅ |
| Ia.262 | —CH₂—CH(Cl)—CO—N(C₂H₅)₂ |
| Ia.263 | —CH₂—CH(Cl)—CO—NH—(n-C₃H₇) |
| Ia.264 | —CH₂—CH(Cl)—CO—N(n-C₃H₇)₂ |
| Ia.265 | —CH₂—CH(Cl)—CO—NH—(n-C₄H₉) |
| Ia.266 | —CH₂—CH(Cl)—CO—N(n-C₄H₉)₂ |
| Ia.267 | —CH₂—CH(Br)—CO—NH₂ |
| Ia.268 | —CH₂—CH(Br)—CO—NH—CH₃ |
| Ia.269 | —CH₂—CH(Br)—CO—N(CH₃)₂ |
| Ia.270 | —CH₂—CH(Br)—CO—NH—C₂H₅ |
| Ia.271 | —CH₂—CH(Br)—CO—N(C₂H₅)₂ |
| Ia.272 | —CH₂—CH(Br)—CO—NH—(n-C₃H₇) |
| Ia.273 | —CH₂—CH(Br)—CO—N(n-C₃H₇)₂ |
| Ia.274 | —CH₂—CH(Br)—CO—NH—(n-C₄H₉) |
| Ia.275 | —CH₂—CH(Br)—CO—N(n-C₄H₉)₂ |
| Ia.276 | —CH=CH—CO—NH₂ |
| Ia.277 | —CH=CH—CO—NH—CH₃ |
| Ia.278 | —CH=CH—CO—N(CH₃)₂ |
| Ia.279 | —CH=CH—CO—NH—C₂H₅ |
| Ia.280 | —CH=CH—CO—N(C₂H₅)₂ |
| Ia.281 | —CH=CH—CO—NH—(n-C₃H₇) |
| Ia.282 | —CH=CH—CO—N(n-C₃H₇)₂ |
| Ia.283 | —CH=CH—CO—NH—(n-C₄H₉) |
| Ia.284 | —CH=CH—CO—N(n-C₄H₉)₂ |
| Ia.285 | —CH=C(Cl)—CO—NH₂ |
| Ia.286 | —CH=C(Cl)—CO—NH—CH₃ |
| Ia.287 | —CH=C(Cl)—CO—N(CH₃)₂ |
| Ia.288 | —CH=C(Cl)—CO—NH—C₂H₅ |
| Ia.289 | —CH=C(Cl)—CO—N(C₂H₅)₂ |
| Ia.290 | —CH=C(Cl)—CO—NH—(n-C₃H₇) |
| Ia.291 | —CH=C(Cl)—CO—N(n-C₃H₇)₂ |
| Ia.292 | —CH=C(Cl)—CO—NH—(n-C₄H₉) |
| Ia.293 | —CH=C(Cl)—CO—N(n-C₄H₉)₂ |
| Ia.294 | —CH=C(Br)—CO—NH₂ |
| Ia.295 | —CH=C(Br)—CO—NH—CH₃ |
| Ia.296 | —CH=C(Br)—CO—NH(CH₃)₂ |
| Ia.297 | —CH=C(Br)—CO—NH—C₂H₅ |
| Ia.298 | —CH=C(Br)—CO—N(C₂H₅)₂ |
| Ia.299 | —CH=C(Br)—CO—NH—(n-C₃H₇) |
| Ia.300 | —CH=C(Br)—CO—N(n-C₃H₇)₂ |
| Ia.301 | —CH=C(Br)—CO—NH—(n-C₄H₉) |
| Ia.302 | —CH=C(Br)—CO—N(n-C₄H₉)₂ |
| Ia.303 | —CH(CH₃)—OCH₃ |
| Ia.304 | —CH₂Cl |
| Ia.305 | —CF₃ |
| Ia.306 | —CH₂OH |
| Ia.307 | —CH(CH₃)OH |
| Ia.308 | —CH₂—CH₂OH |
| Ia.309 | —O-phenyl |
| Ia.310 | —OCH₂-phenyl |
| Ia.311 | —OCH₂—CO—O(n-C₃H₇) |
| Ia.312 | —OCH₂—CO—OCH(CH₃)₂ |
| Ia.313 | —OCH₂—CO—O(n-C₄H₉) |
| Ia.314 | —OCH₂—CO—OCH₂—CH(CH₃)₂ |
| Ia.315 | —OCH₂—CO—OCH(CH₃)—C₂H₅ |

TABLE 1-continued

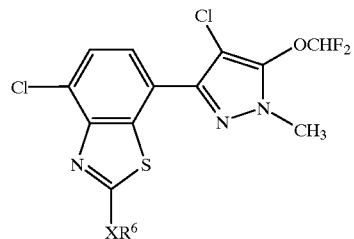

Ia

| No. | —XR⁶ |
|---|---|
| Ia.316 | —OCH₂—CO—OC(CH₃)₃ |
| Ia.317 | —O—CO—CH₃ |
| Ia.318 | —O—CO—C₂H₅ |
| Ia.319 | —O—CO—(n-C₃H₇) |
| Ia.320 | —O—CO—(n-C₄H₉) |
| Ia.321 | —OCH(CH₃)—CO—OCH₃ |
| Ia.322 | —OCH(CH₃)—CO—OC₂H₅ |
| Ia.323 | —OCH(CH₃)—CO—O(n-C₃H₇) |
| Ia.324 | —OCH(CH₃)—CO—OCH(CH₃)₂ |
| Ia.325 | —OCH(CH₃)—CO—O(n-C₄H₉) |
| Ia.326 | —OCH(CH₃)—CO—OCH₂—CH(CH₃)₂ |
| Ia.327 | —OCH(CH₃)—CO—OCH(CH₃)—C₂H₅ |
| Ia.328 | —OCH(CH₃)—CO—OC(CH₃)₃ |
| Ia.329 | —NH—CH₂—CH₂—CN |
| Ia.330 | —N(CH₂—CH₂—CN)₂ |
| Ia.331 | —NH—CH₂—CO—OCH₃ |
| Ia.332 | —N(CH₂—CO—OCH₃)₂ |
| Ia.333 | —NH—CH₂—CO—OC₂H₅ |
| Ia.334 | —N(CH₂—CO—OC₂H₅)₂ |
| Ia.335 | —N(CH₃)—C₂H₅ |
| Ia.336 | —N(CH₃)—(n-C₃H₇) |
| Ia.337 | —N(CH₃)-(n-C₄H₉) |
| Ia.338 | —N(CH₃)—CH(CH₃)₂ |
| Ia.339 | —N(CH₃)—CH₂—CH(CH₃)₂ |
| Ia.340 | —N(CH₃)—CH₂—CH=CH₂ |
| Ia.341 | —N(CH₃)—CH₂—C≡CH |
| Ia.342 | —N(CH₃)—CH₂—CH₂—CN |
| Ia.343 | —N(CH₃)—CH₂—CO—OCH₃ |
| Ia.344 | —N(CH₃)—CH₂—CO—OC₂H₅ |
| Ia.345 | —NH—CO—CH₃ |
| Ia.346 | —NH—CO—C₂H₅ |
| Ia.347 | —NH—CO—(n-C₃H₇) |
| Ia.348 | —NH—CO—(n-C₄H₉) |
| Ia.349 | —NH—SO₂—CH₃ |
| Ia.350 | —NH—SO₂—C₂H₅ |
| Ia.351 | —NH—SO₂—(n-C₃H₇) |
| Ia.352 | —NH—SO₂—(n-C₄H₉) |
| Ia.353 | —S-phenyl |
| Ia.354 | —SCH₂-phenyl |
| Ia.355 | —SCH₂—CO—O(n-C₃H₇) |
| Ia.356 | —SCH₂—CO—OCH(CH₃)₂ |
| Ia.357 | —SCH₂—CO—O(n-C₄H₉) |
| Ia.358 | —SCH₂—CO—OCH₂—CH(CH₃)₂ |
| Ia.359 | —SCH₂—CO—OCH(CH₃)—C₂H₅ |
| Ia.360 | —SCH₂—CO—OC(CH₃)₃ |
| Ia.361 | —S—CO—CH₃ |
| Ia.362 | —SCH(CH₃)—CO—OCH₃ |
| Ia.363 | —SCH(CH₃)—CO—OC₂H₅ |
| Ia.364 | —SCH(CH₃)—CO—O(n-C₃H₇) |
| Ia.365 | —SCH(CH₃)—CO—O(n-C₄H₉) |
| Ia.366 | —CH₂—PO(OCH₃)₂ |
| Ia.367 | —CH₂—PO(OC₂H₅)₂ |
| Ia.368 | —OCH₂—PO(OCH₃)₂ |
| Ia.369 | —OCH₂—PO(OC₂H₅)₂ |
| Ia.370 | —SCH₂—PO(OCH₃)₂ |
| Ia.371 | —SCH₂—PO(OC₂H₅)₂ |
| Ia.372 | —CH₂—CH(Cl)—PO(OCH₃)₂ |
| Ia.373 | —CH₂—CH(Cl)—PO(OC₂H₅)₂ |
| Ia.374 | —CH₂—CH(Br)—PO(OCH₃)₂ |
| Ia.375 | —CH₂—CH(Br)—PO(OC₂H₅)₂ |
| Ia.376 | —CH=CH—PO(OCH₃)₂ |
| Ia.377 | —CH=CH—PO(OC₂H₅)₂ |
| Ia.378 | —CH(CO—OCH₃)₂ |

TABLE 1-continued

Ia

| No. | —XR⁶ |
|---|---|
| Ia.379 | —CH(CO—OC₂H₅)₂ |
| Ia.380 | —CH(CO—OCH₃)[CO—OC(CH₃)₃] |
| Ia.381 | —CH(CO—OC₂H₅)[CO—OC(CH₃)₃] |
| Ia.382 | —CH(CN)—CO—OCH₃ |
| Ia.383 | —CH(CN)—CO—OC₂H₅ |
| Ia.384 | —CH(CN)—CO—OC(CH₃)₃ |

Furthermore, particular preference is given to the substituted pyrazol-3-ylbenzazoles of the formulae Ib to It and IA to IT, in particular to the compounds Ib.001 to Ib.384, which differ from the 10 corresponding compounds Ia.001 to Ia.384 only in that $R^4$ is chlorine:

Ib the compounds Ic.001 to Ic.384, which differ from the corresponding compounds Ia.001 to Ia.384 only in that $R^4$ is fluorine:

Ic the compounds Id.001 to Id.384, which differ from the corresponding compounds Ia.001 to Ia.384 only in that $R^2$ is trifluoromethyl:

Id the compounds Ie.001 to Ie.384, which differ from the corresponding compounds Ia.001 to Ia.384 only in that $R^2$ is trifluoromethyl and $R^4$ is chlorine:

Ie the compounds If.001 to If.384, which differ from the corresponding compounds Ia.001 to Ia.384 only in that $R^2$ is trifluoromethyl and $R^4$ is fluorine:

If the compounds Ig.001 to Ig.384, which differ from the corresponding compounds Ia.001 to Ia.384 only in that $R^2$ is methylsulfonyl:

Ig the compounds Ih.001 to Ih.384, which differ from the corresponding compounds Ia.001 to Ia.384 only in that $R^2$ is methylsulfonyl and $R^4$ is chlorine:

the compounds Ij.001 to Ij.384, which differ from the corresponding compounds Ia.001 to Ia.384 only in that $R^2$ is methylsulfonyl and $R^4$ is fluorine:

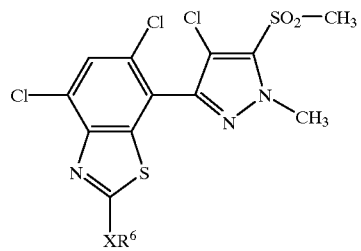

Ij the compounds Ik.001 to Ik.384, which differ from the corresponding compounds Ia.001 to Ia.384 only in that Z is a group —N=C($XR^6$)—O— which is bonded to α via the oxygen:

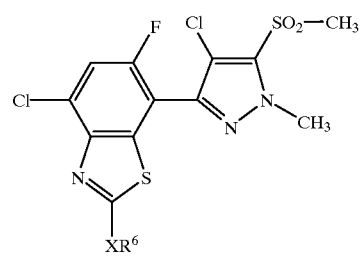

Ik the compounds Im.001 to Im.384, which differ from the corresponding compounds Ia.001 to Ia.384 in that $R^4$ chlorine and Z is a group -N=C($XR^6$)—O— which is bonded to α via the oxygen:

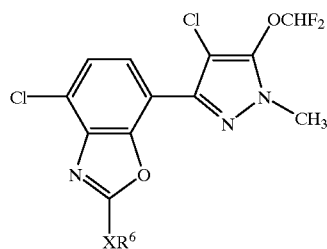

Im the compounds In.001 to In.384, which differ from the corresponding compounds Ia.001 to Ia.384 in that $R^4$ is fluorine and Z is a group —N=C($XR^6$)—O— which is bonded to α via the oxygen:

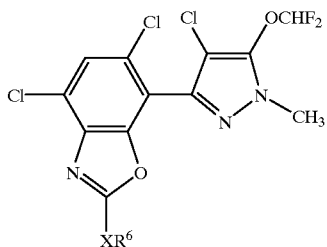

In the compounds Io.001 to Io.384, which differ from the corresponding compounds Ia.001 to Ia.384 in that $R^2$ is trifluoromethyl and Z is a group —N=C($XR^6$)—O— which is bonded to α via the oxygen:

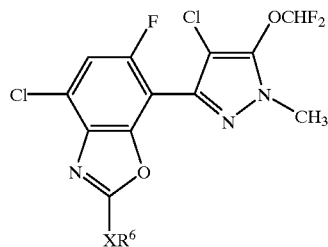

Io the compounds Ip.001 to Ip.384, which differ from the corresponding compounds Ia.001 to Ia.384 in that $R^2$ is trifluoromethyl and $R^4$ is chlorine and Z is a group —$NC_1$=C($XR^6$)—O— which is bonded to α via the oxygen:

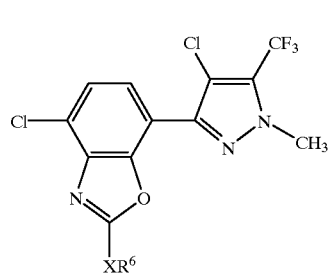

Ip the compounds Iq.001 to Iq.384, which differ from the corresponding compounds Ia.001 to Ia.384 in that $R^2$ is trifluoromethyl and $R^4$ is fluorine and Z is a group —N=C($XR^6$)—O— which is bonded to α via the oxygen:

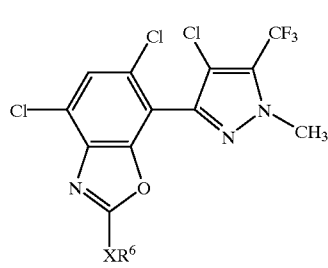

Iq the compounds Ir.001 to Ir.384, which differ from the corresponding compounds Ia.001 to Ia.384 in that $R^2$ is methylsulfonyl and Z is a group —N=C(XR$^6$)—O— which is bonded to α via the oxygen:

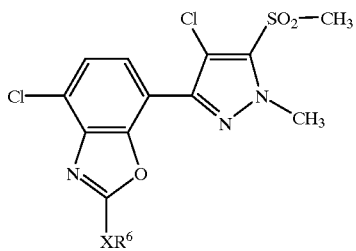

Ir the compounds Is.001 to Is.384, which differ from the corresponding compounds Ia.001 to Ia.384 in that R$^2$ is methylsulfonyl and R$^4$ is chlorine and Z is a group —N=C(XR$^6$)—O— which is bonded to α via the oxygen:

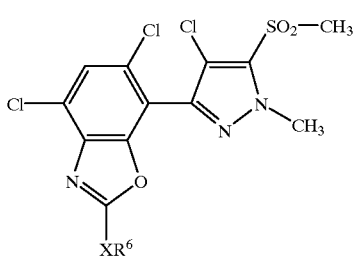

Is the compounds It.001 to It.384, which differ from the corresponding compounds Ia.001 to Ia.384 in that R$^2$ is methylsulfonyl and R$^4$ is fluorine and Z is a group —N=C(XR$^6$)—O— which is bonded to α via the oxygen:

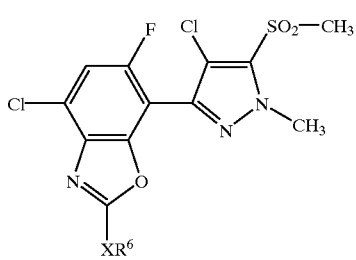

It the compounds IA.001 to IA.384, which differ from the corresponding compounds Ia.001 to Ia.384 only in that the group —N=C(XR$^6$)—S— is bonded to α via the nitrogen:

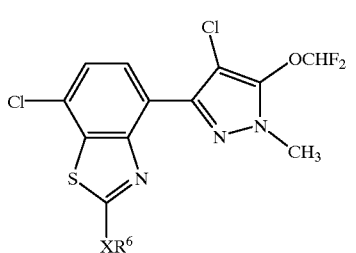

IA the compounds IB.001 to IB.384, which differ from the corresponding compounds Ia.001 to Ia.384 only in that R$^4$ is chlorine and the group —N=C(XR$^6$)—S— is bonded to α via the nitrogen:

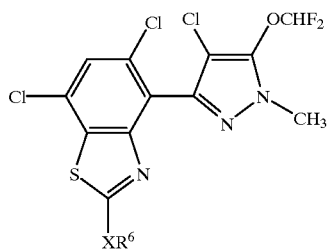

IB the compounds IC.001 to IC.384, which differ from the corresponding compounds Ia.001 to Ia.384 only in that R$^4$ is fluorine and the group —N=C(XR$^6$)—S— is bonded to α via the nitrogen:

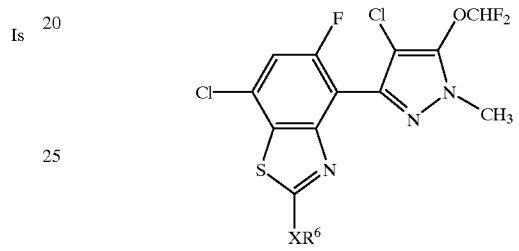

IC the compounds ID.001 to ID.384, which differ from the corresponding compounds Ia.001 to Ia.384 only in that R$^2$ is trifluoromethyl and the group —N—C(XR$^6$)—S— is bonded to α via the nitrogen:

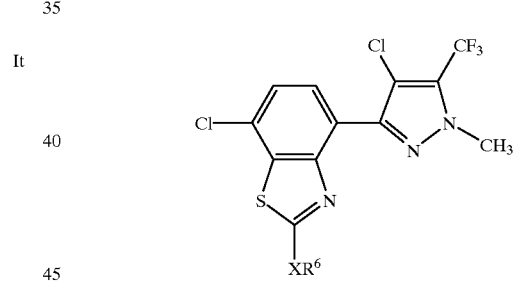

ID the compounds IE.001 to IE.384, which differ from the corresponding compounds Ia.001 to Ia.384 only in that R$^2$ is trifluoromethyl and R$^4$ is chlorine and the group —N=C(XR$^6$)—S— is bonded to α via the nitrogen:

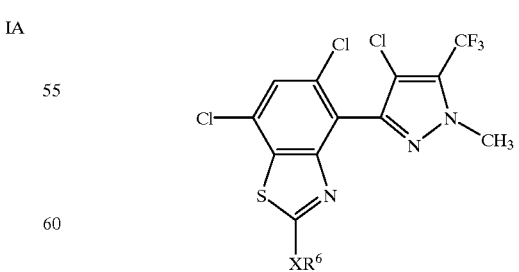

IE the compounds IF.001 to IF.384, which differ from the orresponding compounds Ia.001 to Ia.384 only in that R$^2$ is trifluoromethyl and R$^4$ is fluorine and the group —N=C(XR$^6$)—S— is bonded to α via the nitrogen:

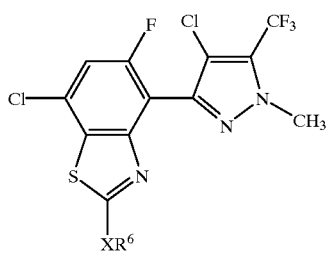

IF the compounds IG.001 to IG.384, which differ from the corresponding compounds Ia.001 to Ia.384 only in that $R^2$ is methylsulfonyl and the group —N=C(XR$^6$)—S— is bonded to α via the nitrogen:

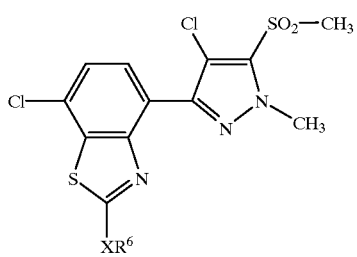

IG the compounds IH.001 to IH.384, which differ from the corresponding compounds Ia.001 to Ia.384 only in that $R^2$ is methylsulfonyl and $R^4$ is chlorine and the group —N=C(XR$^6$)—S— is bonded to α via the nitrogen:

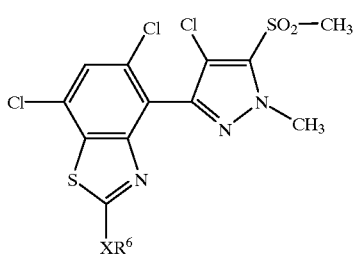

IH the compounds IJ.001 to IJ.384, which differ from the corresponding compounds Ia.001 to Ia.384 only in that $R^2$ is methylsulfonyl and $R^4$ is fluorine and the group —N=C(XR$^6$)—S— is bonded to α via the nitrogen:

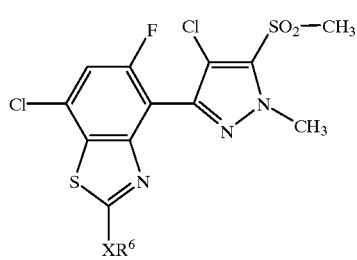

IJ the compounds IK.001 to IK.384, which differ from the corresponding compounds Ia.001 to Ia.384 only in that Z is a group —N=C(XR$^6$)—O— which is bonded to α via the nitrogen:

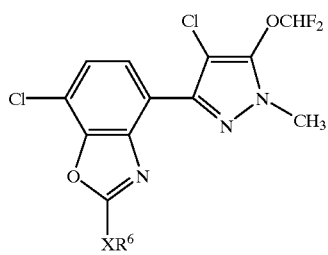

IK the compounds IM.001 to IM.384, which differ from the corresponding compounds Ia.001 to Ia.384 in that $R^4$ is chlorine and Z is a group —NC=C(XR$^6$)—O— which is bonded to α via the nitrogen:

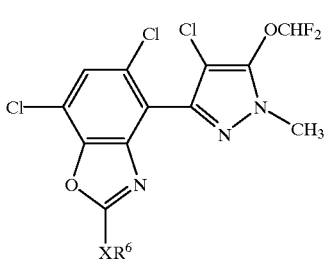

IM the compounds IN.001 to IN.384, which differ from the corresponding compounds Ia.001 to Ia.384 in that $R^4$ is fluorine and Z is a group —N=C(XR$^6$)—O— which is bonded to α via the nitrogen:

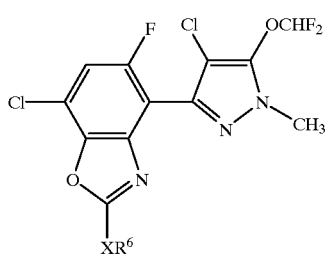

IN the compounds IO.001 to IO.384, which differ from the corresponding compounds Ia.001 to Ia.384 in that $R^2$ is trifluoromethyl and Z is a group —NC$_1$C(XR$^6$)—O— which is bonded to α via the nitrogen:

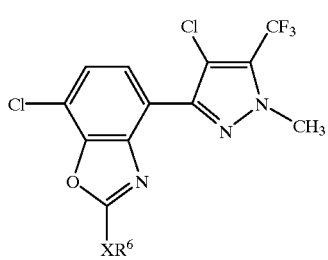

IO the compounds IP.001 to IP.384, which differ from the corresponding compounds Ia.001 to Ia.384 in that $R^2$ is trifluoromethyl and $R^4$ is chlorine and Z is a group —N=C(XR$^6$)—O— which is bonded to α via the nitrogen:

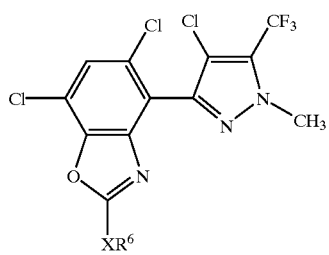

IP the compounds IQ.001 to IQ.384, which differ from the corresponding compounds Ia.001 to Ia.384 in that $R^2$ is trifluoromethyl and $R^4$ is fluorine and z is a group —N=C(XR$^6$)—O— which is bonded to α via the nitrogen:

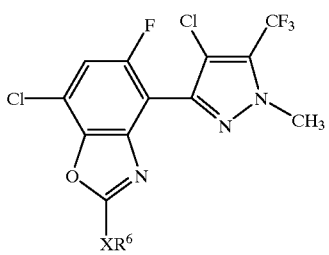

IQ the compounds IR.001 to IR.384, which differ from the corresponding compounds Ia.001 to Ia.384 in that $R^2$ is methylsulfonyl and Z is a group —N=C(XR$^6$)—O— which is bonded to α via the nitrogen:

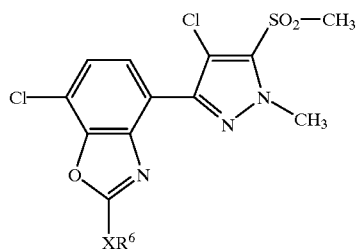

IR the compounds IS.001 to IS.384, which differ from the corresponding compounds Ia.001 to Ia.384 in that $R^2$ is methylsulfonyl and $R^4$ is chlorine and Z is a group —N=C(XR6)—O— which is bonded to α via the nitrogen:

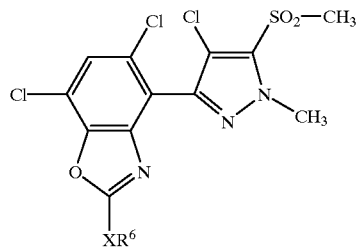

IS the compounds IT.001 to IT.384, which differ from the corresponding compounds Ia.001 to Ia.384 in that $R^2$ is methylsulfonyl and R4 is fluorine and Z is a group —N=C(XR$^6$)—O- which is bonded to α via the nitrogen:

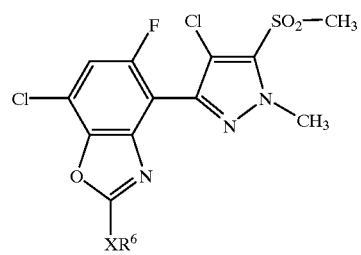

IT

The substituted pyrazol-3-ylbenzazoles of the formula I can be obtained in a variety of ways, in particular according to one of the following processes:

A) Reaction of an aminophenylpyrazole of the formula IIIa or IIIb with a halogen and ammonium thiocyanate or with an alkali metal thiocyanate or alkaline earth metal thiocyanate:

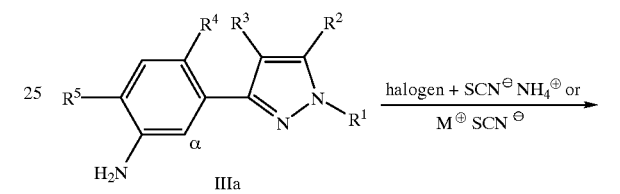

I {Z = —N=C(XR$^6$)—S— bonded to α via the sulfur

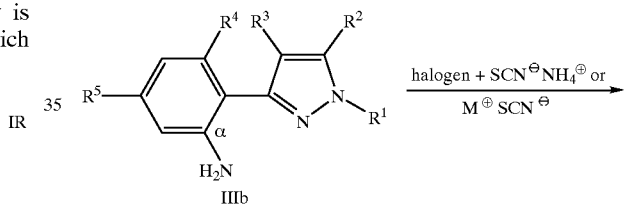

I {Z = —N=C(XR$^6$)—S— bonded to α via the nitrogen

M$^⊕$= an alkali metal ion or 1/2 alkaline earth metal ion

Preferred halogen is chlorine or bromine; amongst the alkali metal/alkaline earth metal thiocyanates, preference is given to sodium thiocyanate.

As a rule, the reaction is carried out in an inert solvent/diluent, for example in a hydrocarbon such as toluene and hexane, in a halogenated hydrocarbon such as dichloromethane, in an ether such as tetrahydrofuran, in an alcohol such as ethanol, in a carboxylic acid such as acetic acid, or in an aprotic solvent such as dimethylformamide, acetonitrile and methyl sulfoxide.

The reaction temperature is usually between the melting point and the boiling point of the reaction mixture, preferably from 0 to 150° C.

To obtain a very high yield of the product of value, halogen and ammonium thiocyanate or alkali metal/alkaline earth metal thiocyanate are employed in about equimolar amounts or in an excess of up to 5 times the molar amount, based on the amount of IIIa or IIIb.

A variant of the process comprises reacting the aminophenylpyrazole IIIa or IIIb initially with ammonium thiocyanate or an alkali metal thiocyanate or alkaline earth metal thiocyanate to give a thiourea IVa or IVb IVa

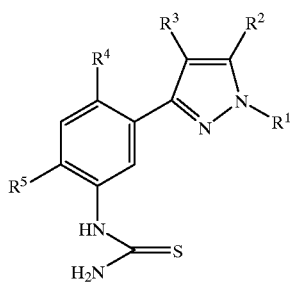

IVb

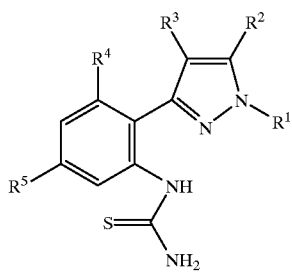

and subsequently converting IVa or IVb by treatment with halogen into I where Z=—N=C(XR$^6$)—S—.

B) Diazotization of an aminophenylpyrazole of the formula IIIa or IIIb, conversion of the respective diazonium salt into an azidophenylpyrazole of the formula Va or Vb and its reaction either B.1) with a carboxylic acid or B.2) initially with a sulfonic acid (to give VIa or VIb), hydrolysis of the resulting sulfonate to the aminophenol VIIa or VCIIb, and their conversion into I:

B.1)

IIIa $\xrightarrow{\text{1) diazot.}}_{\text{2) M}^\oplus\text{N}_3^\ominus}$

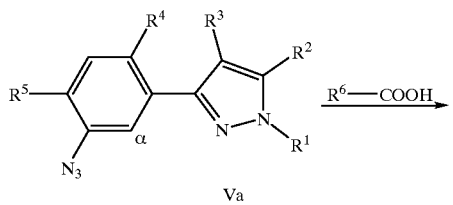

I { Z = —N=C(R$^6$)—O— bonded to α via oxygen }

IIIb $\xrightarrow{\text{1) diazot.}}_{\text{2) M}^\oplus\text{N}_3^\ominus}$

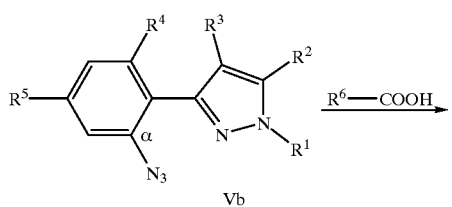

I { Z = —N=C(R$^6$)—O— bonded to α via nitrogen }

M⊕ is an alkali metal ion or ½ alkaline earth metal ion.

B.2)

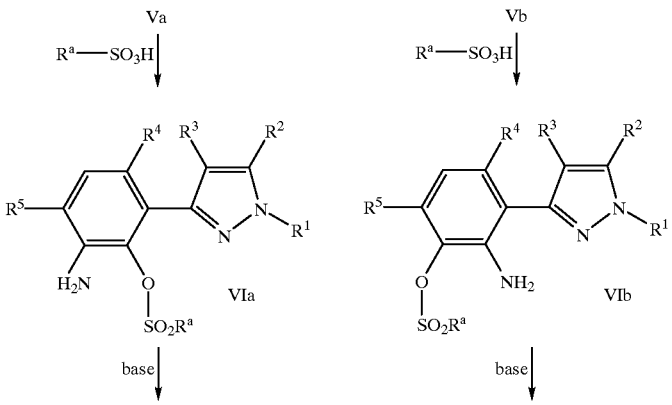

-continued

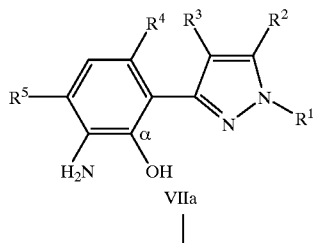
VIIa

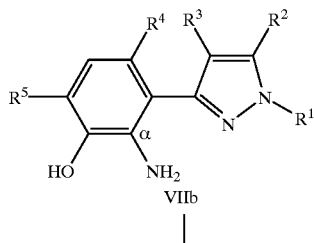
VIIb

I {Z = —N=C(XR⁶)—O— bonded to α  
via oxygen

I {Z = —N=C(XR⁶)—O— bonded to α  
via nitrogen

The details given for process C) also apply to the practice of the diazotization. The conversion in the aryl azides Va/Vb is preferably carried out by reaction of IIIa/IIIb with an alkali metal azide or alkaline earth metal azide such as sodium azide or by reaction with trimethylsilyl azide.

The reaction with a carboxylic acid mentioned under B.1) is carried out either in an inert solvent, for example in ether such as tetrahydrofuran and dioxane, an aprotic solvent such as dimethylformamide and acetonitrile, a hydrocarbon such as toluene and hexane, a halogenated hydrocarbon such as dichloromethane, or without solvent in an excess of carboxylic acid R⁶—COOH. In the last case, addition of a mineral acid such as phosphoric acid may be advantageous.

The reaction is preferably carried out at elevated temperature, for example at the boiling point of the reaction mixture.

The details given above for the reaction of Va/Vb with R⁶—COOCH also apply to the reaction of Va/Vb with a sulfonic acid Ra—SO₃H (where Ra is $C_1$–$C_4$-alkyl or $C_1$–$C_4$-haloalkyl, preferably methyl or trifluoromethyl) mentioned first under B.2).

The subsequent hydrolysis of the sulfonates VIa/VIb is preferably carried out by reaction with an aqueous base such as aqueous sodium hydroxide and aqueous potassium hydroxide, and, if desired, a solvent, for example an ether such as dioxane and tetrahydrofuran or an alcohol such as methanol and ethanol, may be added.

The subsequent reaction to give I is known per se and can be carried out in a very large variety of ways. The reader is referred to the details given in Houben-Weyl, Methoden der Organischen Chemie, Georg Thieme Verlag Stuttgart, Vol. E8a 1993, p. 1032 ff.

C) Diazotization of substituted pyrazol-3-ylbenzazoles of the formula I where XR⁶ is amino, and subsequent conversion of the diazonium salt into compounds I where —XR⁶=cyano or halogen {for the Sandmeyer reaction, cf. for example Houben-Weyl, Methoden der Organischen Chemie, Georg Thieme Verlag Stuttgart, Vol. 5/4, 4th edition, 1960, p. 438ff.}, —X—=sulfur {cf. for example Houben-Weyl, Methoden der Organischen Chemie, Georg Thieme Verlag Stuttgart, Vol. E11, 1984, p. 43 and 176}, —XR⁶=for example —CH₂—CH (halogen)-R⁸, —CH=CH—R⁸, —CH=C(halogen)-R⁸ {in general, these are products of a Meerwein arylation; cf. for example C. S. Rondestredt, Org. React. 11 1960, 189 and H. P. Doyle et al., J. Org. Chem. 42 (1977), 2431C₁}:

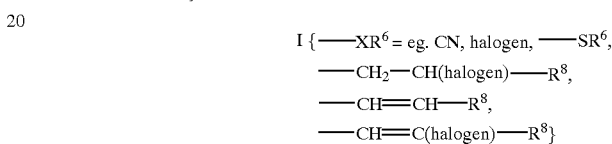

Generally, the diazonium salt is obtained in a conventional manner by reacting I where —XR⁶=amino in an aqueous acid solution, for example in hydrochloric acid, hydrobromic acid or sulfuric acid, with a nitrite such as sodium nitrite and potassium nitrite.

However, it is also possible to work under anhydrous conditions, for example in glacial acetic acid containing hydrogen chloride, in absolute alcohol, in dioxane or tetrahydrofuran, in acetonitrile or in acetone treating the starting material (I where —XR⁶=NH₂) with a nitrite such as tert-butyl nitrite and isopentyl nitrite.

The conversion of the thus-obtained diazonium salt into the corresponding compound I where —XR⁶=cyano, chlorine, bromine or iodine is particularly preferably carried out by treatment with a solution or suspension of a copper(I) salt such as copper(I) cyanide, chloride, bromide and i odide, or with an alkali metal salt solution.

Compounds I where —X—=sulfur are usually obtained by reacting the diazonium salt with a dialkyl disulf ide such as dimethyl disulfide and diethyl disulfide, or with, for example, diallyl disulfide or dibenzyl disulfide.

The Meerwein arylation usually comprises the reaction of the diazonium salts with alkenes (here H₂C=CH—R⁸) or alkynes (here HC≡C—R⁸). Preference is given to using an excess of the alkene or alkyne of up to 3000 mol %, based on the amount of the diazonium salt.

The reactions of the diazonium salt described above can be carried out, for example, in water, in aqueous hydrochloric acid or hydrobromic acid, in a ketone such as acetone, diethyl ketone and methyl ethyl ketone, in a nitrile such as acetonitrile, in an ether such as dioxane and tetrahydrofuran or in an alcohol such as methanol and ethanol.

If not stated otherwise for the individual reactions, the reaction temperatures are usually from (−30) to +50° C.

Preferably, all reaction partners are used in about stoichiometric amounts, but an excess of one or other component of up to about 3000 mol % may also be advantageous.

D) Oxidation of a substituted pyrazol-3-ylbenzazole I where X is sulfur to I where X=—SO— in a conventional manner (cf. for example Houben-Weyl, Methoden der Organischen Chemie, Georg Thieme Verlag Stuttgart, Vol. E 11/1, 1985, p. 702 ff, Vol. IX, 4th edition, 1955, p. 211):

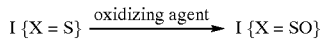

Suitable oxidizing agents are, for example, hydrogen peroxide, organic peroxides such as acetic peroxide, trifluoroacetic peroxide, m-chloroperbenzoic acid, tert-butyl hydroperoxide and tert-butyl hypochlorite, and inorganic compounds such as sodium metaiodate, chromic acid and nitric acid.

Depending on the oxidizing agent, the reaction is usually carried out in an organic acid such as acetic acid and trichloroacetic acid, in a chlorinated hydrocarbon such as methylene chloride, chloroform and 1,2-dichloroethane, in an aromatic hydrocarbon such as benzene, chlorobenzene and toluene or in a protic solvent such as methanol and ethanol. Mixtures of the solvents mentioned may also be suitable.

The reaction temperature is generally from (−30)° C. to the boiling point of the respective reaction mixture, the lower temperature range usually being preferred.

Starting material and oxidizing agent are advantageously employed in about stoichiometric amounts, but one or other component may also be used in excess.

E) Oxidation of a substituted pyrazol-3-ylbenzazole I where X is sulfur or —SO— to I where X=—SO$_2$—in a conventional manner (cf. for example Houben-Weyl, Methoden der Organischen Chemie, Georg Thieme Verlag Stuttgart, Vol. E 11/2, 1985, p. 1132 ff. and Vol. IX, 4th edition, 1955, p. 222 ff.):

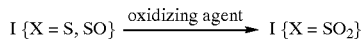

Suitable oxidizing agents are, for example, hydrogen peroxide, organic peroxides such as acetic peroxide, trifluoroacetic peroxide and m-chloroperbenzoic acid, furthermore inorganic oxidizing agents such as potassium permanganate. The presence of a catalyst, for example tungstate, may promote the course of the reaction.

As a rule, the reaction is carried out in an inert solvent, suitable solvents being, depending on the oxidizing agent, for example, organic acids such as acetic acid and propionic acid, chlorinated hydrocarbons such as methylene chloride, chloroform and 1,2-dichloroethane, aromatic hydrocarbons or halogenated hydrocarbons such as benzene, chlorobenzene and toluene, or water. Mixtures of the solvents mentioned may also be used.

Usually the reaction is carried out at from (−30)° C. to the boiling point of the respective reaction mixture, preferably at from 10° C. to the boiling point.

The starting material I where X=sulfur or SO and the oxidizing agent are advantageously employed in about stoichiometric amounts. However, to optimize the conversion of the starting material, an excess of oxidizing agent may be advantageous.

F) Reaction of a substituted pyrazol-3-ylbenzazole I where the group —XR$^6$ is chlorine, bromine, alkylsulfonyl or haloalkylsulfonyl in the presence of a base with an alcohol, mercaptan, amine or a CH-acidic compound (VIII):

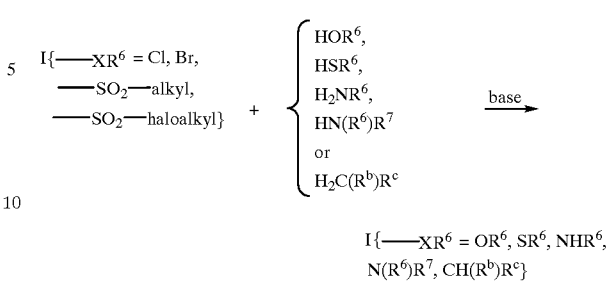

VIII $R^b$ and $R^c$ independently of one another are each cyano or ($C_1$–$C_4$-alkoxy)carbonyl.

The reaction is advantageously carried out in an inert solvent, for example in an ether such as diethyl ether, methyl tert-butyl ether, dimethoxyethane, diethylene glycol dimethyl ether, tetrahydrofuran and dioxane, a ketone such as acetone, diethyl ketone, ethyl methyl ketone and cyclohexanone, a dipolar aprotic solvent such as acetonitrile, dimethylformamide, N-methylpyrrolidone and dimethyl sulfoxide, a protic solvent such as methanol and ethanol, an aromatic hydrocarbon which may be halogenated, if desired, such as benzene, chlorobenzene and 1,2-dichlorobenzene, a heteroaromatic solvent such as pyridine and quinoline or in a mixture of such solvents. Preference is given to tetrahydrofuran, acetone, diethyl ketone and dimethylformamide.

Suitable bases are, for example, the hydroxides, hydrides, alkoxides, carbonates or bicarbonates of alkali metal and alkaline earth metal cations, tertiary aliphatic amines such as triethylamine, N-methylmorpholine and N-ethyl—N,N-diisopropylamine, bi- and tricyclic amines such as diazabicycloundecane (DBU) and diazabicyclooctane (DABCO), or aromatic nitrogen bases such as pyridine, 4-dimethylaminopyridine and quinoline. Combinations of different bases may also be suitable. Preferred bases are sodium hydride, sodium hydroxide, sodium carbonate, potassium carbonate, sodium methoxide, sodium ethoxide and potassium tert-butoxide.

The amines $H_2NR^6$ or $HN(R^6)R^7$ can serve as reaction partners and at the same time as base, in which case the amine should be present in at least twofold excess, based on the amount of starting material I. Of course, a larger excess of amine is also possible, up to about ten times the molar amount, based on the amount of I where —XR$^6$=Cl, Br, —SO$_2$-alkyl or —SO$_2$-haloalkyl.

The starting materials are usually employed in about stoichiometric amounts, but it may be advantageous to use an excess of one or other component with regard to the practice of the process or in order to achieve a very complete conversion of the starting material I {—XR$^6$=Cl, Br, —SO$_2$-alkyl, —SO$_2$-haloalkyl}.

The molar ratio of alcohol, mercaptan, amine or CH-acidic compound (VIII) to base is generally from 1:1 to 1:3.

The concentration of the starting materials in the solvent is usually from 0.1 to 5.0 mol/l.

The reaction can be carried out at from 0° C. to the reflux temperature of the respective reaction mixture.

G) Reaction of a substituted pyrazol-3-ylbenzazole I where —XR$^6$ is halogen with a ($C_1$–$C_6$-alkyl)-Grignard reagent:

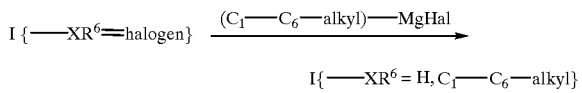

Here, Hal is chloride or bromide.

Generally, the reaction is carried out in an inert solvent/diluent, for example a hydrocarbon such as hexane and toluene, or an ether such as diethyl ether, tetrahydrofuran and dioxane.

If desired, a transition metal catalyst, in amounts of from 0.0001 to 10 mol %, may be added. Suitable transition metal catalysts are, for example, nickel and palladium catalysts such as nickel dichloride, bis(triphenylphosphine)nickel dichloride, [bis(1,2-diphenylphosphino)ethane]nickel dichloride, [bis(1,3-diphenylphosphino)propane]nickel dichloride, palladium dichloride, tetrakis(triphenylphosphine)palladium, bis(triphenylphosphine)palladium dichloride, [bis(1,2-diphenylphosphino)ethane]palladium dichloride, [bis(1,3-diphenylphosphino)propane]palladium dichloride and [bis(diphenylphospino)ferrocene]palladium dichloride, but also mixtures of palladium dichloride or nickel dichloride and phosphines such as triphenylphosphine, bis-1,2-(diphenylphosphino)ethane and bis-1,3-(diphenylphosphino)propane. Depending on how the reaction is carried out, compounds I where —$XR^6$= hydrogen or $C_1$–$C_6$-alkyl or corresponding mixtures of alkylated and non-alkylated compound I result which can, however, be separated in a customary manner.

Generally, the reaction is carried out at from (–100)° C. to the boiling point of the reaction mixture.

The amount of Grignard reagent is not critical; usually, ($C_1$–$C_6$-alkyl)-MgHal is employed in an approximately equimolar amount or in excess, up to about ten times the molar amount, based on the amount of I where —$XR^6$= halogen.

Unless stated otherwise, all the processes described above are advantageously carried out at atmospheric pressure or under the autogenous pressure of the reaction mixture in question.

The work-up of the reaction mixtures is usually carried out in a conventional manner. Unless stated otherwise in the processes described above, the products of value are obtained, for example, after the dilution of the reaction solution with water by filtration, crystallization or solvent extraction, or by removing the solvent, partitioning the residue in a mixture of water and a suitable organic solvent and work-up of the organic phase to afford the product.

The substituted pyrazol-3-ylbenzazoles I can be obtained as isomer mixtures in the preparation; however, if desired, these can be separated into largely pure isomers using customary methods such as crystallization or chromatography, including chromatography over an optically active adsorbent. Pure optically active isomers can be prepared advantageously from suitable optically active starting materials.

Agriculturally useful salts of the compounds I can be formed by reaction with a base of the corresponding cation, preferably an alkali metal hydroxide or hydride, or by reaction with an acid of the corresponding anion, preferably of hydrochloric acid, hydrobromic acid, sulfuric acid, phosphoric acid or nitric acid.

Salts of I where the metal ion is not an alkali metal ion can be prepared by cation exchange of the corresponding alkali metal salt in a conventional manner, similarly ammonium, phosphonium, sulfonium and sulfoxonium salts by means of ammonia, phosphonium, sulfonium or sulfoxonium hydroxides.

The compounds I and their agriculturally useful salts are suitable, both in the form of isomer mixtures and in the form of the pure isomers, as herbicides. The herbicidal compositions comprising I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Taking into account the diversity of application methods, the compounds I, or herbicidal compositions comprising them, can additionally be employed in a further number of crop plants for eliminating undesirable plants. Examples of suitable crops are the following:

Allium cepa, Ananas comosus, Arachis hypogaea, Asparagus officinalis, Beta vulgaris spec. altissima, Beta vulgaris spec. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spec., Manihot esculenta, Medicago sativa, Musa spec., Nicotiana tabacum (N.rustica), Olea europaea, Oryza sativa , Phaseolus lunatus, Phaseolus vulgaris, Picea abies, Pinus spec., Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera and Zea mays.

In addition, the compounds I may also be used in crops which tolerate the action of herbicides owing to breeding, including genetic engineering methods.

Moreover, the substituted pyrazol-3-ylbenzazoles I are also suitable for the desiccation and/or defoliation of plants.

As desiccants, they are suitable, in particular, for desiccating the aerial parts of crop plants such as potatoes, oilseed rape, sunflowers and soybeans. This allows completely mechanical harvesting of these important crop plants.

Also of economic interest is the facilitation of harvesting, which is made possible by dehiscence, or reduction of the adherence to the tree, both concentrated over a period of time, in citrus fruit, olives or other species and varieties of pomaceous fruit, stone fruit and nuts. The same mechanism, ie. promotion of the formation of abscission tissue between fruit or leaf and shoot of the plants, is also important for readily controllable defoliation of useful plants, in particular cotton.

Moreover, shortening the period within which the individual cotton plants mature results in improved fiber quality after harvesting.

The compounds I, or the compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for spreading, or granules, by means of spraying, atomizing, dusting, spreading or pouring. The use forms depend on the intended aims; in any case, they should guarantee a very fine distribution of the active compounds according to the invention.

Suitable inert auxiliaries are essentially: mineral oil fractions of medium to high boiling point, such as kerosene and diesel oil, furthermore coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, eg. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substances, either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or grinding the active compounds together with a solid carrier.

Granules, eg. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges. In general, the formulations comprise approximately from 0.001 to 98% by weight, preferably 0.01 to 95% by weight of at least one active compound I. The active compounds I are employed in a purity of from 90% to 100%, preferably 95% to 100% (according to the NMR spectrum).

The formulation examples which follow illustrate the preparation of such products:

I. 20 parts by weight of the compound No. Ic.001 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of the compound No. Ic.321 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of the active compound No. Ic.343 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV. 20 parts by weight of the active compound No. If.001 are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of the active compound No. Ic.099 are mixed with 97 parts by weight of finely divided kaolin. This gives a dust which comprises 3% by weight of active compound.

VI. 20 parts by weight of the active compound No. If.061 are mixed intimately with 2 parts by weight of calcium dodecylbenzenesulfonate, 8 parts by weight of fatty alcohol polyglycol ether, 2 parts by weight of the sodium salt of a phenol/urea$C_1$lformaldehyde condensate and 68 parts by weight of a paraffinic mineral oil. This gives a stable oily dispersion.

VII. 1 part by weight of the compound No. Ij.043 is dissolved in a mixture composed of 70 parts by weight of cyclohexanone, 20 parts by weight of ethoxylated isooctylphenol and 10 parts by weight of ethoxylated castor oil. The mixture can then be diluted with water to the desired concentration of active compound. This gives a stable emulsion concentrate.

VIII. 1 part by weight of the compound No. Iq.003 is dissolved in a mixture composed of 80 parts by weight of cyclohexane and 20 parts by weight of Wettol® EM 31 (=nonionic emulsifier based on ethoxylated castor oil; BASF AG). The mixture can then be diluted with water to the desired concentration of active compound. This gives a stable emulsion concentrate.

The active compounds I or the herbicidal compositions can be applied pre- or post-emergence. If the active compounds are less well tolerated by certain crop plants, application techniques may be used in which the herbicidal compositions are sprayed, with the aid of the spraying equipment, in such a way that they come into as little contact as possible, if any, with the leaves of the sensitive crop plants, while the active compounds reach the leaves of undesirable plants growing underneath, or the bare soil surface (post-directed, lay-by).

The rates of application of active compound I are from 0.001 to 3.0, preferably 0.01 to 1.0, kg/ha of active substance (a.s.), depending on the control target, the season, the target plants and the growth stage.

To widen the spectrum of action and to achieve synergistic effects, the substituted pyrazol-3-ylbenz(ox/othi)azoles I may be mixed with a large number of representatives of other herbicidal or growth-regulating active compound groups and then applied concomitantly. Suitable components for mixtures are, for example, 1,2,4-thiadiazoles, 1,3, 4-thiadiazoles, amides, aminophosphoric acid and its derivatives, aminotriazoles, anilides, aryloxy/ hetaryloxyalkanoic acids and their derivatives, benzoic acid and its derivatives, benzothiadiazinones, 2-(hetaroyl/aroyl)-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or else concomitantly in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

PREPARATION EXAMPLES

Example 1

2-Amino-4-chloro-7-(4-chloro-5-difluoromethoxy-1-methyl-1-pyrazol-3-yl)-6-fluorobenzothiazole (No. Ic.080)

29 g (0.36 mol) of sodium thiocyanate were added to a solution of 29.3 g (90 mmol) of 2-chloro-5-(4-chloro-5-difluoro-methoxy-1-methyl-1H-pyrazol-3-yl)-4-fluoroaniline in 500 ml of acetic acid. The reaction mixture was stirred for 10 minutes and 28.7 g (0.18 mol) of bromine were then added. Stirring was then continued for a further 16 hours. The mixture was then poured into 2 l of water. The resulting solid product of value was filtered off, washed with water and finally dried. Yield: quantitative;

$^1$H NMR (270 MHz; in CDCl$_3$): δ[ppm]=3.86 (s,3H), 5.44 (s,2H), 6.74 (t,1H), 7.24 (d,1H).

Example 2

4-Chloro-7-(4-chloro-5-difluoromethoxy-1-methyl-1H-pyrazol-3-yl)-6-fluoro-2-(methylthio)benzothiazole (No. Ic.099)

0.4 g (3.9 mmol) of dimethyl disulfide and 1.3 g (12.7 mmol) of tert-butyl nitrite were added to a solution of 0.5 g (1.3 mmol) of 2-amino-4-chloro-7-(4-chloro-5-difluoromethoxy-1-methyl-1H-pyrazol-3-yl)-6-fluorobenzothiazole in 50 ml of dichloromethane. The reaction mixture was stirred for 16 hours and then concentrated. The crude product was purified by silica gel chromatography (eluent: hexane/ethyl acetate=4:1). Yield: 0.3 g;

$^1$H NMR (270 MHz; in CDCl$_3$): δ[ppm]=2.81 (s,3H), 3.88 (s,3H), 6.75 (t,1H), 7.35 (d,1H).

Example 3

2-Bromo-4-chloro-7-(4-chloro-5-difluoromethoxy-1-methyl-1H-pyrazol-3-yl)-6-fluorobenzothiazole (No. Ic.041)

35.2 g (0.34 mol) of sodium bromide and 19.6 g (0.14 mol) of copper(I) bromide were initially added to a solution of 26.4 g (68 mmol) of 2-amino-4-chloro-7-(4-chloro-5-difluoromethoxy-1-methyl-1H-pyrazol-3-yl)-6-fluorobenzothiazole in 1 l of acetonitrile, and 9.2 g (89 mmol) of tert-butyl nitrite were then added dropwise. The reaction mixture was stirred for 16 hours and then admixed with 0.2 l of dilute hydrochloric acid. The solid fraction was subsequently filtered off and washed with 200 ml of ethyl acetate. Product of value which had remained in the aqueous phase was extracted with 200 ml of ethyl acetate. The combined organic phases were washed with water, dried over magnesium sulfate and finally concentrated. The crude product was purified by silica gel chromatography (eluent: ethyl acetate); yield: 17.3 g.

Example 4

2-Amino-7-(4-chloro-5-difluoromethoxy-1-methyl-1H-pyrazol-3-yl)-4,6-dichlorobenzothiazole (No. Ib.080)

4.4 g (13 mmol) of 5-(4-chloro-5-difluoromethoxy-1-methyl-1H-pyrazol-3-yl)-2,4-dichloroaniline, 4.2 g (52 mmol) of sodium thiocyanate and 4.1 g (26 mol) of bromine were reacted by the method of Example 1. Yield: quantitative.

Example 5

7-(4-Chloro-5-difluoromethoxy-1-methyl-1H-pyrazol-3-yl)-4,6-dichloro-2-(ethylthio)benzothiazole (No. Ib.100)

0.8 g (2 mmol) of 2-amino-7-(4-chloro-5-difluoromethoxy-1-methyl-1H-pyrazol-3-yl)-4,6-dichlorobenzothiazole, 0.7 g (6 mmol) of diethyl disulfide and 0.3 g (3 mmol) of tert-butyl nitrite were reacted by the method of Example 2. Yield: 0.2 g.

Example 6

2-Bromo-7-(4-chloro-5-difluoromethoxy-1-methyl-1H-pyrazol-3-yl)-4,6-dichlorobenzothiazole (No. Ib.041)

3.6 g (9 mmol) of 2-amino-7-(4-chloro-5-difluoromethoxy-1-methyl-1H-pyrazol-3-yl)-4,6-dichlorobenzothiazole, 4.6 g (45 mmol) of sodium bromide, 2.6 g (18 mmol) of copper(I) bromide and 1.2 g (12 mmol) of tert-butyl nitrite were reacted by the method of Example 3. Yield: 1.8 g.

Example 7

7-(4-Chloro-5-difluoromethoxy-1-methyl-1H-pyrazol-3-yl)-4,6-dichlorobenzothiazole (No. Ib.001)

3 ml of a 2 M solution of propylmagnesium chloride in diethyl ether (=6 mmol C$_3$H$_7$ MgCl) were added to a solution of 0.45 g (1 mmol) of 2-bromo-7-(4-chloro-5-difluoromethoxy-1-methyl-1H-pyrazol-3-yl)-4,6-dichlorobenzothiazole in 6 ml of diethyl ether. The mixture was stirred for 5 hours and then admixed with 10 ml of dilute hydrochloric acid. The organic phase was subsequently separated off, washed twice with water, then dried over magnesium sulfate and finally concentrated. The crude product was purified by silica gel chromatography (eluent: hexane/ethyl acetate 1:1). Yield: 0.3 g.

Example 8

2-Amino-4-chloro-7-(4-chloro-1-methyl-5-trifluoromethyl-1H-pyrazol-3-yl)-6-fluorobenzothiazole (No. If.080)

80 g (0.24 mol) of 2-chloro-5-(4-chloro-1-methyl-5-trifluoromethyl-1H-pyrazol-3-yl)-4-fluoroaniline, 79 g (0.98 mol) of sodium thiocyanate and 78 g (0.49 mol) of bromine were reacted by the method of Example 1. Yield: quantitative.

Example 9
4-Chloro-7-(4-chloro-1-methyl-5-trifluoromethyl-1H-pyrazol-3-yl)-6-fluoro-2-(methylthio)benzothiazole (No. If.099)

0.7 g (1.8 mmol) of 2-amino-4-chloro-7-(4-chloro-1-methyl-5-tri-fluoromethyl-1H-pyrazol-3-yl)-6-fluorobenzothiazole, 0.5 g (5.4 mmol) of dimethyl disulfide and 0.33 g (2.7 mmol) of tert-butyl nitrite were reacted by the method of Example 2. Yield: 0.3 g.

Example 10
2-Bromo-4-chloro-7-(4-chloro-1-methyl-5-trifluoromethyl-1H-pyrazol-3-yl)-6-fluorobenzothiazole (No. If.041)

73 g (0.12 mol) of 2-amino-4-chloro-7-(4-chloro-1-methyl-5-tri-fluoromethyl-1H-pyrazol-3-yl)-6-fluorobenzothiazole, 126 g (1.22 mmol [sic]) of sodium bromide, 35 g (0.24 mol) of copper(I) bromide and 16.3 g (0.16 mol) of tert-butyl nitrite were reacted by the method of Example 3. Yield: 18.2 g.

Example 11
N-(4-Chloro-7-(4-chloro-1-methyl-5-trifluoromethyl-1H-pyrazol-3-yl)-6-fluorobenzothiazol-2-yl)acetamide (No. If.345)

0.12 g (4.7 mmol) of sodium hydride and then 0.7 g (1.6 mmol) of 2-bromo-4-chloro-7-(4-chloro-1-methyl-5-trifluoromethyl-1H-pyrazol-3-yl)-6-fluorobenzothiazole were added to a solution of 0.38 g (6.4 mmol) of acetamide in 20 ml of tetrahydrofuran. The reaction mixture was subsequently stirred for 16 hours and then concentrated. The resulting crude product was purified by silica gel chromatography (eluent: hexane/ethyl acetate 4:1 and 1:1). Yield: 0.4 g.

Example 12
Methyl 3-(4-chloro-7-(4-chloro-5-difluoromethoxy-1-methyl-1H-pyrazol-3-yl)-6-fluorobenzothiazol-2-yl) acrylate (No. Ic.232)

1 g (3.1 mmol) of 2-amino-4-chloro-7-(4-chloro-5-difluoromethoxy-1-methyl-1H-pyrazol-3-yl)-6-fluorobenzothiazole, 5.5 g (64 mmol) of methyl acrylate, 0.45 g (3.4 mmol) of copper(II) chloride and 0.33 g (3.2 mmol) of tert-butyl nitrite were successively dissolved in 30 ml of acetonitrile. The reaction mixture was subsequently stirred for 16 hours and then admixed with 100 ml of dilute hydrochloric acid. The resulting product of value was then extracted with 200 ml of methyl tert-butyl ether. The combined organic phases were washed twice with water, dried over magnesium sulfate and finally concentrated. The crude product was purified by silica gel chromatography (eluent: hexane/ethyl acetate=4:1). Yield: 0.13 g.

Example 13
4-Chloro-7-(4-chloro-5-difluoromethoxy-1-methyl-1H-pyrazol-3-yl)-6-fluorobenzothiazole (No. Ic.001) and 4-chloro-7-(4-chloro-5-difluoromethoxy-1-methyl-1H-pyrazol-3-yl)-6-fluoro-2-methyl-benzothiazole (No. Ic.002)

2.9 ml of a 3 M solution of methylmagnesium chloride in tetrahydrofuran (=8,7 mmol $H_3CMgCl$) were added dropwise to a solution of 2 g (4.4 mmol) of 2-bromo-4-chloro-7-(4-chloro-5-difluoromethoxy-1-methyl-1H-pyrazol-3-yl)-6-fluorobenzothiazole and 0.15 g (0.22 mmol) of bis(triphenylphosphine)nickel dichloride in 20 ml of tetrahydrofuran which had been heated to reflux temperature. The reaction mixture was subsequently stirred for a further 12 hours at reflux temperature and then admixed with 40 ml of dilute hydrochloric acid. The resulting product was extracted from the aqueous phase using 100 ml of ethyl acetate. The combined organic phases were washed twice with water, dried over magnesium sulfate and then concentrated. The crude product was purified by silica gel chromatography (eluent: hexane/ethyl acetate=4:1). The two products of value were subsequently separated using silica gel MPLC (eluent: cyclohexane/ethyl acetate=20:1). Yield: 0.11 g (compound Ic.001) and 0.28 g (compound Ic.002).

Example 14
4-Chloro-7-(4-chloro-5-difluoromethoxy-1-methyl-1H-pyrazol-3-yl)-6-fluoro-2-propylbenzothiazole (No. Ic.004)

0.65 ml of a 2 M solution of propylmagnesium chloride in diethyl ether (=1,3 mmol $C_3H_7$ MgCl) was added dropwise to a solution of 0.4 g (0.9 mmol) of 2-bromo-4-chloro-7-(4-chloro-5-difluoromethoxy-1-methyl-1H-pyrazol-3-yl)-6-fluorobenzothiazole in 30 ml of diethyl ether. The reaction mixture was subsequently stirred for a further 16 hours and then admixed with 40 ml of dilute hydrochloric acid. The resulting product was extracted from the aqueous phase using 100 ml of ethyl acetate. The combined organic phases were dried over magnesium sulfate and then concentrated. The crude products were purified by silica gel chromatography (eluent:hexane/ethyl acetate=9:1). Yield: 0.1 g.

Example 15
4-Chloro-7-(4-chloro-5-difluoromethoxy-1-methyl-1H-pyrazol-3-yl)-6-fluoro-2-methoxybenzothiazole (No. Ic.042)

0.1 g (4.4 mmol) of sodium hydride were dissolved in 20 ml of methanol. After the evolution of gas had ceased, the solution was mixed with 0.7 g (1.6 mmol) of 2-bromo-4-chloro-7-(4-chloro-5-difluoromethoxy-1-methyl-1H-pyrazol-3-yl)-6-fluorobenzo-thiazole. The reaction mixture was subsequently stirred for 16 hours and then concentrated. Finally, the crude produce was purified by silica gel chromatography (eluent: hexane/ethyl acetate=1:1). Yield: 0.5 g.

Example 16
4-Chloro-7-(4-chloro-5-difluoromethoxy-1-methyl-1H-pyrazol-3-yl)-2-dimethylamino-6-fluorobenzothiazole (No. Ic.082)

A slow current of gaseous dimethylamine was introduced into a solution of 0.7 g (1.6 mmol) of 2-bromo-4-chloro-7-(4-chloro-5-difluoromethoxy-1-methyl-1H-pyrazol-3-yl)-6-fluorobenzothiazole in 50 ml of dimethylformamide of a temperature of 70–80° C. until the reaction had come to completion (about 30 minutes). The mixture was subsequently concentrated and the residue was admixed with 50 ml of water. The resulting product was extracted from the aqueous phase using 100 ml of ethyl acetate. The combined organic phases were washed twice with water, then dried over magnesium sulfate and finally concentrated. The crude product was purified by silica gel chromatography (eluent: hexane/ethyl acetate=4:1). Yield: 0.46 g.

Example 17
Methyl N-(4-chloro-7-(4-chloro-5-difluoromethoxy-1-methyl-1H-pyrazol-3-yl)-6-fluorobenzothiazole-2-yl) aminoacetate (No. Ic.343)

A solution of 0.7 g (1.6 mmol) of 2-bromo-4-chloro-7-(4-chloro-5-difluoromethoxy-1-methyl-1H-pyrazol-3-yl)-6-fluorobenzo-thiazole, 0.43 g (3.1 mmol) of potassium carbonate and 0.43 g (3.1 mmol) of sarcosine methyl ester hydrochloride in 30 ml of dimethylformamide was heated to 100° C. for 2 hours. The mixture was subsequently concentrated and the residue was then admixed with 50 ml of water. The resulting product was extracted from the aqueous phase using 100 ml of ethyl acetate. The combined organic phases were washed twice with water, dried over magnesium sulfate and finally concentrated. The crude product was purified by silica gel chromatography (eluent: hexane/ethyl acetate 4:1). Yield: 0.18 g.

Example 18

Methyl 2-(4-chloro-7-(4-chloro-5-difluoromethoxy-1-methyl-1H-pyrazol-3-yl)-6-fluorobenzothiazole-2-yloxy) propionate (No. Ic.321)

0.11 g (4.7 mmol) of sodium hydride were added to a solution of 0.65 g (6.2 nmol) of methyl 2-hydroxypropionate in 20 ml of tetrahydrofuran. After the evolution of gas had ceased, the mixture was admixed with 0.7 g (1.6 mmol) of 2-bromo-4-chloro-7-(4-chloro-5-difluoromethoxy-1-methyl-1H-pyrazol-3-yl)-6-fluoro-benzothiazole. The mixture was subsequently stirred for 3 days and then admixed with 50 ml of water. The resulting product was extracted from the aqueous phase using 100 ml of ethyl acetate. The combined organic phases were washed twice with water, dried over magnesium sulfate and finally concentrated. The crude product was purified by silica gel chromatography (eluent: hexane/ethyl acetate=4:1). Yield: 0.3 g.

Example 19

2-Amino-4-chloro-7-(4-chloro-1-methyl-5-methylsulfonyl-1H-pyrazol-3-yl)-6-fluorobenzothiazole (No. Ij.080)

7.5 g (21 mmol) of 2-chloro-5-(4-chloro-1-methyl-5-methyl-sulfonyl-1H-pyrazol-3-yl)-4-fluoroaniline, 6.9 g (85 mol) of sodium thiocyanate and 6.9 g (43 mmol) of bromine were reacted by the method of Example 1. Yield: quantitative.

Example 20

4-Chloro-7-(4-chloro-1-methyl-5-methylsulfonyl-1H-pyrazol-3-yl)-2-ethylthio-6-fluorobenzothiazole (No. Ij.100)

1 g (2.5 mmol) of 2-amino-4-chloro-7-(4-chloro-1-methyl-5-methyl-sulfonyl-1H-pyrazol-3-yl)-6-fluorobenzothiazole, 0.66 g (7.3 mol) of diethyl disulfide and 0.37 g (3.7 mmol) of tert-butyl nitrite were reacted by the method of Example 2. Yield: 0.4 g.

Example 21

2-Bromo-4-chloro-7-(4-chloro-1-methyl-5-methylsulfonyl-1H-pyrazol-3-yl)-6-fluorobenzothiazole (No. Ij.041)

6 g (14 mmol) of 2-amino-4-chloro-7-(4-chloro-1-methyl-5-methyl-sulfonyl-1H-pyrazol-3-yl-6-fluorobenzothiazole, 7.6 g (70 mmol) of sodium bromide, 4.2 g (30 mmol) of copper(I) bromide and 2.2 g (22 mmol) of tert-butyl nitrite were reacted by the method of Example 3. Yield: 3.6 g.

Example 22

Ethyl tert-butyl 2-(4-chloro-7-(4-chloro-5-difluoromethoxy-1-methyl-1H-pyrazol-3-yl)-6-fluorobenzothiazole-2-yl)malonate (No. Ic.381)

0.1 g (4.7 mmol) of sodium hydride were added to a solution of 0.9 g (5 mmol) of ethyl tert-butyl malonate in 10 ml of dimethylformamide. After the evolution of gas had ceased, the mixture was admixed with 1.5 g (3.3 mmol) of 2-bromo-4-chloro-7-(4-chloro-5-difluoromethoxy-1-methyl-1H-pyrazol-3-yl)-6-fluoro-benzothiazole. The reaction mixture was stirred for a further hour and then concentrated. The residue was admixed with 50 ml of water. The product of value was extracted from the aqueous phase using 100 ml of ethyl acetate. The extract was dried over magnesium sulfate and finally concentrated. Yield: 1 g.

Example 23

Ethyl 2-(4-chloro-7-(4-chlor-5-difluormethoxy-1-methyl-1H-pyrazol-3-yl)-6-fluorobenzothiazole-2-yl)acetate (No. Ic.021)

0.30 g (2 mmol) of trifluoromethanesulfonic acid was added to a solution of 1 g (1.8 mmol) of ethyl tert-butyl 2-(4-chloro-7-(4-chloro-5-difluoromethoxy-1-methyl-1H-pyrazol-3-yl)-6-fluoro-benzothiazole-2-yl)malonate in 10 ml of dichloromethane. The mixture was subsequently stirred for an hour and then concentrated. The residue was admixed with 10 ml of acetic acid. This mixture was subsequently heated under reflux for 8 hours. The reaction mixture was then concentrated and the residue was mixed with 50 ml of water. The product of value was extracted from the aqueous phase using 100 ml of ethyl acetate. The extract was washed with dilute aqueous sodium bicarbonate solution and water, dried over magnesium sulfate and finally concentrated. The crude product was purified by silica gel chromatography (eluent: hexane/ethyl acetate=4:1). Yield: 0.4 g.

In addition to the active compounds described above, further pyrazol-3-ylbenzazoles of the formula I which were prepared or are preparable in a similar manner are listed in Table 2 below:

TABLE 2

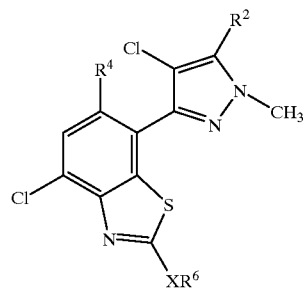

I {$R^1$ = $CH_3$; $R^3$,$R^5$ = Cl;
Z = —N=C($XR^6$)—S—
bonded to α via the sulfur}

| No. | $R^2$ | $R^4$ | $XR^6$ | M.p./$^1$H NMR [ppm]/MS [m/z] |
|---|---|---|---|---|
| Ib.001 | $OCHF_2$ | Cl | H | 3.89(s, 3H), 6.77(t, 1H), 7.71(s, 1H), 9.07 (s, 1H) |
| Ib.002 | $OCHF_2$ | Cl | $CH_3$ | 2.85(s, 3H), 3.88(s, 3H), 6.76(t, 1H), 7.63 (s, 1H) |
| Ib.041 | $OCHF_2$ | Cl | Br | 3.88(s, 3H), 6.74(t, 1H), 7.66(s, 1H) |
| Ib.080 | $OCHF_2$ | Cl | $NH_2$ | 3.82(s, 3H), 7.41(t, 1H), 7.60(s, 1H), 8.04 (s, 2H){in $(CD_3)_2SO$} |
| Ib.099 | $OCHF_2$ | Cl | $SCH_3$ | 105–110° C. |
| Ib.100 | $OCHF_2$ | Cl | $SC_2H_5$ | 76–77° C. |
| Ic.001 | $OCHF_2$ | F | H | 3.88(s, 3H), 6.76(t, 1H), 7.47(d, 1H), 9.06 (s, 1H) |
| Ic.002 | $OCHF_2$ | F | $CH_3$ | 108–110° C. |
| Ic.004 | $OCHF_2$ | F | n-$C_3H_7$ | 1.06(t, 3H), 1.90(sext., 2H), 3.10(t, 2H), 3.89(s, 3H), 6.76(t, 1H), 7.39(d, 1H) |
| Ic.021 | $OCHF_2$ | F | $CH_2$—CO—$OC_2H_5$ | 1.32(t, 3H), 4.10(s, 2H), 4.11(s, 3H), 4.26(q, 2H), 7.42(d, 1H) |
| Ic.041 | $OCHF_2$ | F | Br | 445 [M]$^+$, 366 [M-Br]$^+$ |
| Ic.042 | $OCHF_2$ | F | $OCH_3$ | 120° C. |
| Ic.054 | $OCHF_2$ | F | $OCH_2$—C≡CH | 117–118° C. |
| Ic.080 | $OCHF_2$ | F | $NH_2$ | 3.82(s, 3H), 7.41(t, 1H), 7.49(d, 1H), 7.89 (s, 2H){in $(CD_3)_2SO$} |
| Ic.082 | $OCHF_2$ | F | $N(CH_3)_2$ | 150° C. |
| Ic.099 | $OCHF_2$ | F | $SCH_3$ | 96–98° C. |
| Ic.232 | $OCHF_2$ | F | CH=CH—CO—$OCH_3$ | 158–160° C. |
| Ic.307 | $OCHF_2$ | F | $CH(CH_3)$—OH | 1.72(d, 3H), 3.11(s, 1H), 3.90(s, 3H), 5.29 (q, 1H), 6.76(t, 1H), 7.41(d, 1H) |
| Ic.321 | $OCHF_2$ | F | $OCH(CH_3)$—CO—$OCH_3$ | 1.69(d, 3H), 3.80(s, 3H), 3.86(s, 3H), 5.63 (q, 1H), 6.76(t, 1H), 7.25(d, 1H) |
| Ic.335 | $OCHF_2$ | F | $N(CH_3)$—$C_2H_5$ | 1.27(t, 3H), 3.19(s, 3H), 3.58(q, 2H), 3.87 (s, 3H), 6.74(t, 1H), 7.20(d, 1H) |
| Ic.340 | $OCHF_2$ | F | $N(CH_3)$—$CH_2$—CH=$CH_2$ | 3.15(s, 3H), 3.86(s, 3H), 4.14(d, 2H), 5.25 (d, 1H), 5.26(d, 1H), 5.84(m, 1H), 6.75 (t, 1H), 7.20(d, 1H) |
| Ic.341 | $OCHF_2$ | F | $N(CH_3)$—$CH_2$—C≡CH | 113° C. |
| Ic.343 | $OCHF_2$ | F | $N(CH_3)$—$CH_2$—CO—$OCH_3$ | 3.23(s, 3H), 3.78(s, 3H), 3.89(s, 3H), 4.41 (s, 2H), 6.74(t, 1H), 7.21(d, 1H) |
| Ic.381 | $OCHF_2$ | F | $CH(COOC_2H_5)CO$—$OC(CH_3)_3$ | sirup |
| If.001 | $CF_3$ | F | H | 4.13(s, 3H), 7.48(d, 1H), 9.07(s, 1H) |
| If.002 | $CF_3$ | F | $CH_3$ | 2.87(s, 3H), 4.11.(s, 3H), 7.40(d, 1H) |
| If.041 | $CF_3$ | F | Br | 4.12(s, 3H), 7.44(d, 1H) |
| If.042 | $CF_3$ | F | $OCH_3$ | 399 [M]$^+$ |
| If.043 | $CF_3$ | F | $OC_2H_5$ | 1.48(t, 3H), 4.10(s, 3H), 4.67(q, 2H), 7.30 (d, 1H) |
| If.054 | $CF_3$ | F | $OCH_2$—C≡CH | 2.63(t, 1H), 4.09(s, 3H), 5.24(d, 2H), 7.30 (d, 1H) |
| If.061 | $CF_3$ | F | $OCH_2$—CO—$OCH_3$ | 3.82(s, 3H), 4.10(s, 3H), 5.16(s, 2H), 7.31 (d, 1H) |
| If.080 | $CF_3$ | F | $NH_2$ | 4.11(s, 3H), 7.51(d, 1H), 7.93(s, 2H){in $(CD_3)_2SO$} |
| If.082 | $CF_3$ | F | $N(CH_3)_2$ | 3.21(s, 6H), 4.10(s, 3H), 7.22(d, 1H) |
| If.099 | $CF_3$ | F | $SCH_3$ | 2.81(s, 3H), 4.11(s, 3H), 7.35(d, 1H) |
| If.100 | $CF_3$ | F | $SC_2H_5$ | 1.51(t, 3H), 3.37(q, 2H), 4.10(s, 3H), 7.35 (d, 1H) |
| If.232 | $CF_3$ | F | CH=CH—CO—$OCH_3$ | 3.86(s, 3H), 4.12(s, 3H), 6.68(d, 1H), 7.47 (d, 1H), 7.91(d, 1H) |
| If.321 | $CF_3$ | F | $OCH(CH_3)$—CO—$OCH_3$ | 1.70(d, 3H), 3.80(s, 3H), 4.10(s, 3H), 5.63(q, 1H), 7.29(d, 1H) |
| If.335 | $CF_3$ | F | $N(CH_3)$—$CH_2$—$CH_3$ | 1.27(t, 3H), 3.19(s, 3H), 3.57(q, 2H), 4.10 |

TABLE 2-continued

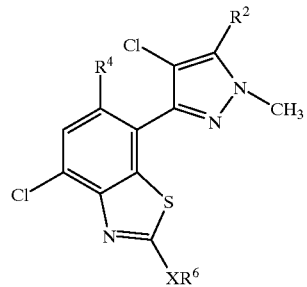

I {R¹ = CH₃; R³,R⁵ = Cl;
Z = —N=C(XR⁶)—S—
bonded to α via the sulfur}

| No. | R² | R⁴ | XR⁶ | M.p./¹H NMR [ppm]/MS [m/z] |
|---|---|---|---|---|
| If.340 | CF₃ | F | N(CH₃)—CH₂—CH=CH₂ | (s, 3H), 7.21(d, 1H) 3.17(s, 3H), 4.09(s, 3H), 4.15(d, 2H), 5.26 (d, 1H), 5.28(d, 1H), 5.85(m, 1H), 7.22 (d, 1H) |
| If.341 | CF₃ | F | N(CH₃)—CH₂—C≡CH | 126° C. |
| If.343 | CF₃ | F | N(CH₃)—CH₂—CO—OCH₃ | 3.22(s, 3H), 3.78(s, 3H), 4.10(s, 3H), 4.41 (s, 2H), 7.22(d, 1H) |
| If.345 | CF₃ | F | NH—CO—CH₃ | 2.31(s, 3H), 4.12(s, 1H), 7.40(d, 1H), 9.25 (s, 1H) |
| Ij.001 | SO₂—CH₃ | F | H | 379 [M]⁺ |
| Ij.041 | SO₂—CH₃ | F | Br | 3.36(s, 3H), 4.30(s, 3H), 7.45(d, 1H) |
| Ij.042 | SO₂—CH₃ | F | OCH₃ | 3.35(s, 3H), 4.25(s, 3H), 4.28.(s, 3H), 7.30 (d, 1H) |
| Ij.043 | SO₂—CH₃ | F | OC₂H₅ | 1.48(t, 3H), 3.34(s, 3H), 4.26(s, 3H), 4.68 (q, 2H), 7.29(d, 1H) |
| Ij.054 | SO₂—CH₃ | F | OCH₂—C≡CH | 2.67(t, 1H), 3.34(s, 3H), 4.27(s, 3H), 5.15 (d, 2H), 7.31(d, 1H) |
| Ij.082 | SO₂—CH₃ | F | N(CH₃)₂ | 3.22(s, 6H), 3.35(s, 3H), 4.29(s, 3H), 7.22 (d, 1H) |
| Ij.080 | SO₂—CH₃ | F | NH₂ | 3.54(s, 3H), 4.20(s, 3H), 7.51(d, 1H), 7.95 (s, 2H){in (CD₃)₂SO} |
| Ij.099 | SO₂—CH₃ | F | SCH₃ | 425 [M]⁺ |
| Ij.100 | SO₂—CH₃ | F | SC₂H₅ | 1.51(t, 3H), 3.34(s, 3H), 3.38(q, 2H), 4.18 (s, 3H), 7.35(d, 1H) |
| Ij.232 | SO₂—CH₃ | F | CH=CH—CO—OCH₃ | 3.36(s, 3H), 3.86(s, 3H), 4.31(s, 3H), 6.79 (d, 1H), 7.47(d, 1H), 7.90(d, 1H) |
| Ij.345 | SO₂—CH₃ | F | NH—CO—CH₃ | 2.31(s, 3H), 3.36(s, 3H), 4.30(s, 3H), 7.40 (d, 1H), 9.71(s, 1H) |

Example 24
4-Chloro-7-(4-chloro-1-methyl-5-trifluoromethyl-1H-pyrazol-3-yl)-2-ethyl-6-fluorobenzoxazole (No. Iq.003)

A solution of 0.5 g (1.4 mmol) of 2-chloro-5-(4-chloro-1-methyl-5-trifluoromethyl-1H-pyrazol-3-yl)-4-fluorophenyl azide in 100 ml of propionic acid was heated to reflux temperature for 20 hours and then concentrated. The residue was admixed with 100 ml of ethyl acetate. The organic phase was washed with saturated aqueous sodium bicarbonate solution, then dried over magnesium sulfate and finally concentrated. The crude product was purified by silica gel chromatography (eluent: hexane/ethyl acetate 15:1). Yield: 0.3 g; ¹H NMR (400 MHz; in CDCl₃): δ[ppm]= 1.44 (t,3H), 2.98 (q,2H), 4.12 (s,3H), 7.25 (d,1H).

Precursor:
2-Chloro-5-(4-chloro-1-methyl-5-trifluoromethyl-1H-pyrazol-3-yl)-4-fluorophenyl azide 0.46 g (4.5 mmol) of tert-butyl nitrite and 0.3 g (4.5 mmol) of sodium azide were added to a solution of 1 g (3 mmol) of 2-chloro-5-(4-chloro-1-methyl-5-trifluoromethyl-1H-pyrazol-3-yl)-4-fluoroaniline in 20 ml of trifluoroacetic acid. The mixture was subsequently stirred for 2 hours and then admixed with 50 ml of water. The resulting product was extracted from the aqueous phase using 100 ml of methyl tert-butyl ether. The extract was washed with 10% strength aqueous sodium hydroxide solution, then dried over magnesium sulfate and finally concentrated. The crude product was purified by silica gel chromatography (eluent: hexane/ethyl acetate=1:1). Yield: 0.7 g; ¹H NMR (400 MHz; in (CD₃)₂SO): δ[ppm]=4.10 (s,3H), 7.53 (d,1H), 7.77 (d,1H).

Use examples (herbicidal activity)

The herbicidal activity of the substituted pyrazol-3-ylbenzazoles was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active compounds, which had been suspended or emulsified in water, were applied directly after sowing by means of finely distributing nozzles. The containers were irrigated gently to promote germination and growth and subsequently covered with translucent plastic hoods until the plants had rooted. This cover causes uniform germination of the test plants, unless this has been adversely affected by the active compounds.

For the post-emergence treatment, the test plants were first grown to a height of 3 to 15 cm, depending on the plant habit, and only then treated with the active compounds which had been suspended or emulsified in water. The test plants were for this purpose either sown directly and grown in the same containers, or they were first grown separately as seedlings and transplanted into the test containers a few days prior to treatment. The rate of application for the post-emergence treatment was 31.2 or 15.6 g/ha of a.s. (active substance).

Depending on the species, the plants were kept at 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage, or normal course of growth.

The plants used in the greenhouse experiments belonged to the following species:

| Scientific name | Common name |
| --- | --- |
| Abutilon theophrasti | velvet leaf |
| Amaranthus retroflexus | redroot pigweed |
| Polygonum persicaria | ladysthumb |
| Solanum nigrum | black nightshade |
| Veronica subspecies | speedwell |

The compound Ic.099, applied post-emergence, showed a very good herbicidal activity against the abovementioned broad-leaved plants at rates of application of 31.2 and 15.6 g/ha a.s.

Use examples (desiccant/defoliant activity)

The test plants used were young cotton plants with 4 leaves (without cotyledons) which had been grown under greenhouse conditions (relative atmospheric humidity 50 to 70%; day/night temperature 27/20°C.).

The young cotton plants were subjected to foliar treatment to runoff point with aqueous preparations of the active compounds (with an addition of 0.15% by weight of the fatty alcohol alkoxide Plurafac® LF 700[1], based on the spray mixture). The amount of water applied was 1000 1/ha (converted). After 13 days, the number of leaves shed and the degree of defoliation in % were determined.

No leaves were shed in the untreated control plants.

[1] a low-foam, nonionic surfactant from BASF AG

We claim:

1. A substituted pyrazol-3-ylbenzazole of the formula I

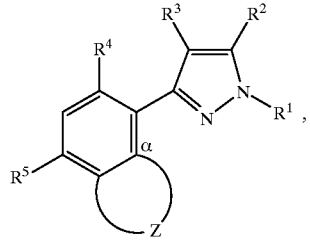

where:
$R^1$ is hydrogen, $C_1$–$C_4$-alkyl or $C_1$–$C_4$-haloalkyl;
$R^2$ is cyano, $C_1$–$C_4$-alkyl, $C_1$–$C_4$haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfinyl, $C_1$–$C_4$-haloalkylsulfinyl, $C_1$–$C_4$-alkylsulfonyl or $C_1$–$C_4$-haloalkylsulfonyl;

$R^3$ is hydrogen, halogen, cyano, nitro, $C_1$–$C_4$-alkyl or $C_1$–$C_4$-haloalkyl;

$R^4$ is hydrogen or halogen;

$R^5$ is hydrogen, halogen, cyano, $C_1$–$C_4$-alkyl, $C_1$–$C_4$-haloalkyl, $C_1$–$C_4$-alkoxy or $C_1$–$C_4$-haloalkoxy;

Z is a group —N=C($XR^6$)—O— or —N=C($XR^6$)—S— which is bonded to a by the nitrogen, oxygen or sulfur;

X is a chemical bond, oxygen, sulfur, —S(O)—, —$SO_2$—, —NH— or —N($R^7$)—;

$R^6$ is $C_1$–$C_6$-alkyl, $C_1$–$C_6$-haloalkyl, cyano-$C_1$–$C_4$-alkyl, hydroxy-$C_1$–$C_4$-alkyl, $C_3$–$C_6$-alkenyl, cyano-$C_3$–$C_6$-alkenyl, $C_3$–$C_6$-haloalkenyl, $C_3$–$C_6$-alkynyl, cyano-$C_3$–$C_6$-alkynyl, $C_3$–$C_6$-haloalkynyl, $C_1$–$C_4$-alkoxy-$C_1$–$C_4$-alkyl, $C_1$–$C_4$-haloalkoxy-$C_1$–$C_4$-alkyl, $C_3$–$C_4$-alkenyloxy-$C_1$–$C_4$-alkyl, $C_3$–$C_4$-alkynyloxy-$C_1$–$C_4$-alkyl, $C_3$–$C_8$-cloalkyloxy-$C_1$–$C_4$-alkyl, amino-$C_1$–$C_4$-alkyl, $C_1$–$C_4$-alkylamino-$C_1$–$C_4$-alkyl, di($C_1$–$C_4$-alkyl)amino-$C_1$–$C_4$-alkyl, $C_1$–$C_4$-alkylthio-$C_1$–$C_4$-alkyl, $C_1$–$C_4$-haloalkylthio-$C_1$–$C_4$-alkyl, $C_3$–$C_4$-alkenylthio-$C_1$–$C_4$-alkyl, $C_3$–$C_4$-alkynylthio-$C_1$–$C_4$-alkyl, $C_1$–$C_4$-alkylsulfinyl-$C_1$–$C_4$-alkyl, $C_1$–$C_4$-haloalkylsulfinyl-$C_1$–$C_4$-alkyl, $C_3$–$C_4$-alkenylsulfinyl-$C_1$–$C_4$-alkyl, $C_3$–$C_4$-alkynylsulfinyl-$C_1$–$C_4$-alkyl, $C_1$–$C_4$-alkylsulfonyl-$C_1$–$C_4$-alkyl, $C_1$–$C_4$-haloalkyl-sulfonyl-$C_1$–$C_4$-alkyl, $C_3$–$C_4$-alkenylsulfonyl-$C_1$–$C_4$-alkyl, $C_3$–$C_4$-alkynylsulfonyl-$C_1$–$C_4$-alkyl, hydroxycarbonyl-$C_1$–$C_4$-alkyl, ($C_1$–$C_4$-alkoxy)carbonyl-$C_1$–$C_4$-alkyl which is unsubstituted or substituted by a cyano or ($C_1$–$C_4$-alkoxy)carbonyl group, ($C_1$–$C_4$-alkylthio)carbonyl-$C_1$–$C_4$-alkyl, aminocarbonyl-$C_1$–$C_4$-alkyl, $C_1$–$C_4$-alkylamino-carbonyl-$C_1$–$C_4$-alkyl, di($C_1$–$C_4$-alkyl)aminocarbonyl-$C_1$–$C_4$-alkyl, di($C_1$–$C_4$-alkyl)phosphonyl-$C_1$–$C_4$-alkyl, ($C_1$–$C_4$-alkoxy)imino-$C_1$–$C_4$-alkyl, ($C_3$–$C_4$-alkenyloxy)imino-$C_1$–$C_4$-alkyl, $C_3$–$C_8$-cycloalkyl, $C_3$–$C_8$-cycloalkyl-$C_1$–$C_4$-alkyl, phenyl, phenyl-$C_1$–$C_4$-alkyl, 3- to 7-membered heterocyclyl or heterocyclyl-$C_1$–$C_4$-alkyl, ($C_1$–$C_4$-alkyl)carbonyl, ($C_1$–$C_4$-haloalkyl)carbonyl, ($C_1$–$C_4$-alkoxy)carbonyl, $C_1$–$C_4$-alkylsulfonyl, $C_1$–$C_4$-haloalkylsulfonyl, hydrogen, cyano, mercapto, amino, halogen, —$CH_2$—CH(halogen)-$R^8$, —CH=CH—$R^8$ or —CH=C(halogen)—$R^8$, where $R^8$ is hydroxycarbonyl, ($C_1$–$C_4$-alkoxy)ycarbonyl, ($C_1$–$C_4$-alkylthio)carbonyl, aminocarbonyl, $C_1$–$C_4$-alkylaminocarbonyl, di($C_1$–$C_4$-alkyl)aminocarbonyl or di($C_1$–$C_4$-alkyl)phosphonyl, with the provisos that if X is a oxygen, sulfur, —NH—, —N($R^7$)—, —S(O)— or —$SO_2$—, $R^6$ is not hydroaen, cyano, mercapto, amino, halogen, —$CH_2$—CH(haloaen)-$R^8$, —CH=CH—$R^8$ or —CH=C(halogen)-$R^8$, and if X is —S(O)— or —$SO_2$, $R^6$ is not ($C_1$–$C_4$-alkyl)carbonyl, $C_1$–$C_4$-haloalkyl)carbonyl, ($C_1$–$C_4$-alkoxy)carbonyl, $C_1$–$C_4$-alkylsulfonyl or $C_1$–$C_4$-haloalkylsulfonyl:

$R^7$ is $C_1$–$C_6$-alkyl, $C_1$–$C_6$-haloalkyl, cyano-$C_1$–$C_4$-alkyl, hydroxy-$C_1$–$C_4$-alkyl, $C_3$–$C_6$-alkenyl, cyano-$C_3$–$C_6$-alkenyl, $C_3$–$C_6$-haloalkenyl, $C_3$–$C_6$-alkynyl, cyano-$C_3$–$C_6$-alkynyl, $C_3$–$C_6$-haloalkynyl, $C_1$–$C_4$-alkoxy, $C_1$–$C_4$-alkyl, $C_1$–$C_4$-haloalkoxy-$C_1$–$C_4$-alkyl, $C_3$–$C_4$-alkenyloxy-$C_1$–$C_4$-alkyl, $C_3$–$C_4$-alkynyloxy-$C_1$–$C_4$-alkyl, $C_3$–$C_8$-cycloalkyloxy-$C_1$–$C_4$-alkyl, amino-$C_1$–$C_4$-alkyl, $C_1$–$C_4$-alkylamino-$C_1$–$C_4$-alkyl, di($C_1$–$C_4$-alkyl)amino-$C_1$–$C_{c4}$-alkyl, $C_1$–$C_4$-alkylthio-$C_1$–$C_4$-alkyl, $C_1$–$C_4$-haloalkylthio-$C_1$–$C_4$-alkyl, $C_3$–$C_4$-alkenylthio-$C_1$–$C_4$-alkyl, $C_3$–$C_4$-alkynylthio- $C_1$–$C_4$,-alkyl, $C_1$–$C_4$-alkylsulfinyl-$C_1$–$C_4$-alkyl, $C_1$–$C_{C4}$-haloalkylsulfinyl-$C_1$–$C_4$-alkyl, $C_3$–$C_4$-alkenyl-sulfinyl-$C_1$–$C_4$-alkyl, $C_3$–$C_1$-alkynylsulfinyl-$C_1$–$C_4$-alkyl, $C_1$–$C_4$-alkylsulfonyl-$C_1$–$C_4$-alkyl, $C_1$–$C_1$-haloalkyl- sulfonyl-$C_1$–$C_4$-alkyl, $C_3$–$C_4$-alkeny/sulfonyl-$C_1$–$C_4$-alkyl, $C_3$–$C_4$-alkynylsulfonyl-$C_1$–$C_4$-alkyl, hydroxycarbonyl-$C_1$–$C_4$-alkyl, ($C_1$–$C_4$-alkoxy)carbonyl-$C_1$–$C_4$-alkyl which is unsubstituted or substituted by a cyano or ($C_1$–$C_4$-alkoxy)carbonyl group, ($C_1$–$C_4$-alkylthio)carbonyl-$C_1$–$C_4$-alkyl, aminocarbonyl-$C_1$–$C_4$-alkyl, $C_1$–$C_4$-alklamino-carbonyl-$C_1$–$C_{C4}$-alkyl, di($C_1$–$C_4$-alkyl)aminocarbonyl-$C_1$–$C_4$-akyl, di($C_1$–$C_4$-alkyl)phosphonyl-$C_1$–$C_4$-alkl, ($C_1$–$C_4$-alkoyl)imino-$C_1$–$C_4$-alkyl, ($C_3$–$C_4$-alkenyloxy)imino-$C_1$–$C_4$-alkyl, $C_3$–$C_8$-cycloalkyl-$C_1$–$C_4$-alkyl; phenyl, phenyl-$C_1$–$C_4$-alkyl, 3- to 7-membered heterocyclyl or heterocyclyl-$C_1$–$C_4$-alkyl; where each cycloalkyl, phenyl and heterocyclyl ring in the definitions of $R^6$ and $R^7$ is unsubstituted or substituted by one to four substituents selected in each case from the group consisting of cyano, nitro, amino, hydroxyl, carboxyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsuffonyl, ($C_1$–$C_4$-alkoxy)carbonyl, ($C_1$–$C_4$-alkyl)carbonyl, ($C_1$–$C_4$-haloalkyl)carbonyl, ($C_1$–$C_4$-alkyl)carbonyloxy, ($C_1$–$C_4$-haloalkyl)carbonyloxy and di($C_1$–$C_4$-alkyl)amino; or $R^6$ and $R^7$together are a 1,3-propylene, tetramethylene, pentamethylene or ethyleneoxyethylene chain which is unsubstituted or substituted by one to four $C_1$–$C_4$-alkyl groups or one or two ($C_1$–$C_4$-alkoxy)carbonyl groups, or the agriculturally useful salts of these compounds.

2. A substituted pyrazol-3-ylbenzazole as claimed in claim 1, where each cycloalkyl and each heterocyclyl ring in the definitions of $R^6$ and $R^7$ contains a carbonyl or thiocarbonyl ring member.

3. A herbicidal composition comprising a herbicidally active amount of at least one substituted pyrazol-3-ylbenzazole of the formula I or an agriculturally useful salt of I, as claimed in claim 1, and at least one inert liquid or solid carrier.

4. A composition for the desiccation or defoliation of plants, comprising an amount of at least one substituted pyrazol-3-ylbenzazole of the formula I or an agriculturally useful salt of l, as claimed in claim 1, which acts as a desiccant, a defoliant, or both a desiccant and a defoliant, and at least one inert liquid or solid carrier.

5. A process for preparing herbicidally active compositions, which comprises mixing a herbicidally active amount of at least one substituted pyrazol-3-ylbenzazole of the formula I or an agriculturally useful salt of I, as claimed in claim 1, with at least one inert liquid or solid carrier.

6. A process for preparing compositions which act as desiccants or defoliants, which comprises mixing an amount of at least one substituted pyrazol-3-ylbenzazole of the formula I or an agriculturally useful salt of I, as claimed in claim 1, which acts as a desiccant, a defoliant, or both a desiccant and defoliant, with at least one inert liquid or solid carrier.

7. A method for controlling undesirable vegetation, which comprises applying a herbicidally active amount of at least one substituted pyrazol-3-ylbenzazole of the formula I or of an agriculturally useful salt of I, as claimed in claim 1, to plants, their habitat or on seeds.

8. A method for the desiccation or defoliation of plants, which comprises applying an amount of at least one substituted pyrazol-3-ylbenzazole of the formula I or of an agriculturally useful salt of I, as claimed in claim 1, which acts as a desiccant, a defoliant, or both a desiccant and a defoliant, to plants.

9. A method as claimed in claim 8, wherein cotton is treated.

10. A process for preparing a substituted pyrazol-3-ylbenzazole of the formula I as claimed in claim 1 where Z is —N=C(NH$_2$)—S—, which comprises reacting an aminophenylpyrazole of the formula IIIa or IIIb

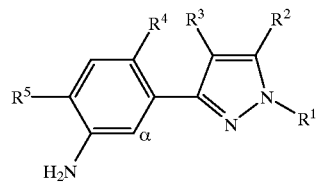

IIIa

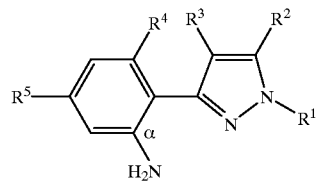

IIIb either with a halogen and amonium thiocyanate or an alkali metal thiocyanate or alkaline earth metal thiocyanate, or initially with ammonium thiocyanate or an alkali metal thiocyanate or alkaline earth metal thiocyanate and then with a halogen.

11. A process for preparing a substituted pyrazol-3-ylbenzazole of the formula I as claimed in claim 1 where $XR^6$ is halogen or cyano, which comprises diazotizing a substituted pyrazol-3-ylbenzazole I where $XR^6$ is amino and subsequently reacting the resulting diazonium salt with copper(I) halide or copper(I) cyanide.

12. A process for preparing a substituted pyrazol-3-ylbenzazole of the formula I as claimed in claim 1 where X is sulfur, which comprises diazotizing a substituted pyrazol-3-ylbenzazole I where $XR^6$ is amino and subsequently reacting the resulting diazonium salt with a dialkyl disulfide of the formula $R^6$S—$SR^6$.

13. A process for preparing a substituted pyrazol-3-ylbenzazole of the formula I as claimed in claim 1 where $XR^6$ is —CH$_2$—CH(Cl)—$R^8$, —CH$_2$—CH(Br)—$R^8$, —CH=CH—$R^8$, —CH=C(Cl)—$R^8$ or —CH=C(Br)—$R^8$, which comprises diazotizing a substituted pyrazol-3-ylbenzazole I where $XR^6$ is amino and subsequently reacting the resulting diazonium salt with an alkene of the formula H$_2$C=CH—$R^8$ or an alkyne of the formula HC≡C—R$_8$ and copper(I) chloride, copper(I) bromide, copper(II) chloride or copper(III) bromide.

14. A process for preparing a substituted pyrazol-3-ylbenzazole of the formula I as claimed in claim 1 where X is oxygen, sulfur, —NH— or —N($R^7$)— or where $XR^6$ is CH($R^b$)$R^c$ where $R^b$ and $R^c$ independently of one another are each cyano or ($C_1$–$C_4$-alkoxy)carbonyl, which comprises reacting a substituted pyrazol-3-ylbenzazole I where $XR^6$ is chlorine, bromine, —SO$_2$-alkyl or —SO$_2$-haloalkyl in the presence of a base with a nucleophile HO$R^6$, HS$R^6$, H$_2$N$R^6$, HN($R^6$)$R^7$ or H$_2$C($R^b$)$R^c$.

15. A process for preparing a substituted pyrazol-3-ylbenzazole of the formula I as claimed in claim 1 where $XR^8$ is $C_1$–$C_6$-alkyl, which comprises reacting a substituted pyrazol-3-ylbenzazole I where XR⁶ is halogen, with a (C₁–C₆-alkyl)-Grignard reagent.

16. A process for preparing a substituted pyrazol-3-ylbenzazole of the formula I as claimed in claim 1 where Z is —N=C(R⁶)—O—, which comprises diazotizing an aminophenylpyrazole of the formula IIIa or IIIb

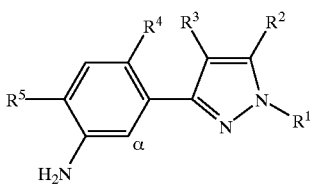

IIIa

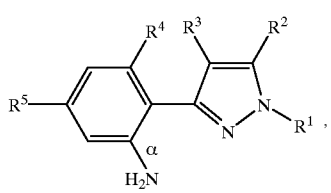

IIIb reacting the resulting diazonium salt with an alkali metal azide to give an azidophenylpyrazole of the formula Va or Vb

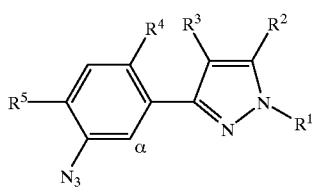

Va

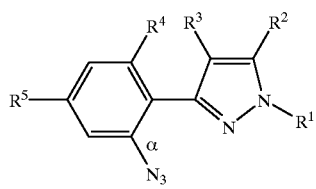

Vb and finally reacting this with a carboxylic acid of formula R⁶—COOH.

17. A substituted pyrazol-3ylbenzazole as claimed in claim 1, where $R^1$ is methyl, $R^2$ is difluoromethoxy, $R^3$ is halogen, $R^5$ is halogen and Z is —N=C(XR⁶)—O— or —N=C(XR⁶)—S— bonded to a by the oxygen or sulfur.

18. A substituted pyrazol-3-ylbenzazole as claimed in claim 1, where $R^1$ is $C_1$–$C_4$-alkyl.

19. A substituted pyrazol-3-ylbenzazole as claimed in claim 1, where $R^1$ is methyl.

20. A substituted pyrazol-3-ylbenzazole as claimed in claim 1, where $R^2$ is $C_1$–$C_4$-haloalkoxy.

21. A substituted pyrazol-3-ylbenzazole as claimed in claim 1, where $R^2$ is difluoromethoxy.

22. A substituted pyrazol-3-ylbenzazole as claimed in claim 1, where $R^3$ is halogen.

23. A substituted pyrazol3-ylbenzazole as claimed in claim 1, where $R^5$ is halogen.

24. A substituted pyrazol-3-ylbenzazole as claimed in claim 1, where Z is —N=C(XR⁶)—O— bonded to α by the oxygen.

25. A substituted pyrazol-3-ylbenzazole as claimed in claim 1, where $R^6$ is $C_1$–$C_6$-alkyl, $C_3$–$C_6$-alkenyl, $C_3$–$C_6$-alkynyl, $C_1$–$C_4$-alkoxy-$C_1$–$C_4$-alkyl, ($C_1$–$C_4$-alkoxy)carbonyl-$C_1$–$C_4$-alkyl, $C_3$–$C_8$-cycloalkyl, $C_3$–$C_8$-cycloalkyl-$C_1$–$C_4$-alkyl, phenyl or phenyl-$C_1$–$C_4$-alkyl.

26. A substituted pyrazol-3-ylbenzazole as claimed in claim 1, where $R^6$ is $C_1$–$C_6$-alkyl, $C_1$–$C_4$-alkoxy-$C_1$-alkyl or $C_3$–$C_8$-cycloalkyl.

27. A substitute pyrazol-3-ylbenzazole as claimed in claim 1, where X is a cemical bond.

* * * * *

UNITED STATES PATENT AND TRADEMARK OFFICE
CERTIFICATE OF CORRECTION

PATENT NO. : 6,232,470 B1
DATED : May 15, 2001
INVENTOR(S) : Zagar et al.

It is certified that error appears in the above-identified patent and that said Letters Patent is hereby corrected as shown below:

Column 55,
Line 65, "alkylsuffinyl" should be -- alkylsulfinyl --.

Column 56,
Line 7, "a" should be -- α --.
Line 18, "$C_3$-$C_8$-cloalkyloxy" should be -- $C_1$-$C_4$-cycloalkyloxy --.
Line 46, "alkoxy)ycarbonyl" should be -- alkoxy)carbonyl --.
Line 50, "hydroaen" should be -- hydrogen --.
Line 51, "(haloaen)" should be -- (halogen) --.
Line 65, "$C_1$-$C_{C4}$-alkyl" should be -- $C_1$-$C_4$-alkyl --.

Column 57,
Line 1, "$C_1$-$C_{4'}$-alkyl" should be -- $C_1$-$C_4$-alkyl --.
Line 2, "$C_1$-$C_{C4}$-haloalkylsulfinyl" should be -- $C_1$-$C_4$-haloalkylsulfinyl --.
Line 5, "haloalkyl- sulfonyl" should be -- haloalkyl-sulfonyl --.
Line 12, "$C_1$-$C_{C4}$-alkyl" should be -- $C_1$-$C_4$-alkyl --.
Line 14, "alkl" should be -- alkyl --.
Line 14, "alkoyl" should be -- alkoxy --.
Line 15, after "$C_1$-$C_4$-alkyl," insert -- $C_3$-$C_8$-cycloalkyl, --.
Line 25, "haloalkylsuffonyl" should be -- haloalkylsulfonyl --.
Line 33, after "compounds" insert -- | --.

Column 58,
Line 55, "(III)" should be -- (II) --.
Line 67, "$XR^8$" should be -- $XR^6$ --.

UNITED STATES PATENT AND TRADEMARK OFFICE
CERTIFICATE OF CORRECTION

PATENT NO. : 6,232,470 B1
DATED : May 15, 2001
INVENTOR(S) : Zagar et al.

It is certified that error appears in the above-identified patent and that said Letters Patent is hereby corrected as shown below:

Column 60,
Line 13, "3ylbenzazole" should be -- 3-ylbenzazole --.
Line 16, "a" should be -- α --.
Line 26, "pyrazol3" should be -- pyrazol-3 --.
Line 31, after "is" insert -- hydrogen, --.
Line 38, "substitute" should be -- substituted --.

Signed and Sealed this

First Day of October, 2002

Attest:

JAMES E. ROGAN
Attesting Officer     Director of the United States Patent and Trademark Office

UNITED STATES PATENT AND TRADEMARK OFFICE
CERTIFICATE OF CORRECTION

PATENT NO. : 6,232,470 B1
DATED : May 15, 2001
INVENTOR(S) : Zagar et al.

It is certified that error appears in the above-identified patent and that said Letters Patent is hereby corrected as shown below:

Column 56,
Lines 60-61, "$C_1$-$C_4$-alkoxy, $C_1$-$C_4$-alkyl" should be -- $C_1$-$C_4$-alkoxy-$C_1$-$C_4$-alkyl --.

Column 57,
Line 3, "$C_3$-$C_1$-alkynylsulfinyl" should be -- $C_3$-$C_4$-alkynylsulfinyl- --.
Line 5, "$C_1$-$C_1$-haloalkyl-sulfonyl-$C_1$-$C_4$-alkyl" should be
-- $C_1$-$C_4$ haloalkylsulfonyl-$C_1$-$C_4$-alkyl --.
Line 11, "$C_1$-$C_4$-alklamino-" should be -- $C_1$-$C_4$-alkylamino- --.
Line 13, "aminocarbonyl-$C_1$-$C_4$-akyl" should be -- aminocarbonyl-$C_1$-$C_4$-alkyl --.

Column 58,
Line 53, "HC≡C-$R_8$" should be -- HC≡C-$R^8$ --.

Column 60,
Line 36, "$R^6$ is $C_1C_6$-alkyl, $C_1$-$C_4$-alkoxy-$C_1$-alkyl or" should be -- $R^6$ is hydrogen, $C_1$-$C_6$-alkyl, $C_1$-$C_4$-alkoxy-$C_1$-$C_4$-alkyl or --.
Line 39, "cemical bond" should be -- chemical bond --.

Signed and Sealed this

Eighteenth Day of March, 2003

JAMES E. ROGAN
*Director of the United States Patent and Trademark Office*